(12) United States Patent
Basore et al.

(10) Patent No.: US 10,967,096 B2
(45) Date of Patent: *Apr. 6, 2021

(54) TISSUE SEALANT COMPOSITIONS, VASCULAR CLOSURE DEVICES, AND USES THEREOF

(71) Applicant: MediBeacon Inc., St. Louis, MO (US)

(72) Inventors: Bob O. Basore, Wildwood, MO (US); William L. Neumann, St. Louis, MO (US); Richard B. Dorshow, St. Louis, MO (US); Raghavan Rajagopalan, St. Peters, MO (US)

(73) Assignee: MediBeacon Inc., St. Louis, MO (US)

( * ) Notice: Subject to any disclaimer, the term of this patent is extended or adjusted under 35 U.S.C. 154(b) by 253 days.

This patent is subject to a terminal disclaimer.

(21) Appl. No.: 16/289,469

(22) Filed: Feb. 28, 2019

(65) Prior Publication Data
US 2019/0192727 A1 Jun. 27, 2019

Related U.S. Application Data

(62) Division of application No. 15/223,240, filed on Jul. 29, 2016, now Pat. No. 10,881,759, which is a
(Continued)

(51) Int. Cl.
*A61L 24/10* (2006.01)
*A61L 24/00* (2006.01)
*A61L 24/04* (2006.01)

(52) U.S. Cl.
CPC .......... *A61L 24/102* (2013.01); *A61L 24/001* (2013.01); *A61L 24/0015* (2013.01);
(Continued)

(58) Field of Classification Search
CPC .... A61L 24/011; A61L 24/106; A61L 24/102; A61L 24/0015; A61L 24/0042;
(Continued)

(56) References Cited

U.S. PATENT DOCUMENTS 4,298,598 A 11/1981 Schwarz et al.
4,377,572 A 3/1983 Schwarz et al.
(Continued)

FOREIGN PATENT DOCUMENTS

AU 75097/87 1/1988
EP 0592242 4/1994
(Continued)

OTHER PUBLICATIONS

Aryal et al. (2006), J. Mater. Chem. 16, 4642-48.
(Continued)

*Primary Examiner* — Jocelin C Tanner
(74) *Attorney, Agent, or Firm* — Armstrong Teasdale LLP

(57) ABSTRACT

The present invention provides tissue sealant compositions and vasculature closure devices useful for the optical detection of tissue seal and/or clot formation. Compositions and devices of the present invention comprise optical dyes which undergo an observable change as the compositions and/or devices are incorporated into a tissue seal and/or clot, for example a change in fluorescence quantum yield and/or a change in visual color including a change in emission and/or absorption wavelength. Tissue sealants and vasculature closure devices of the present invention are useful for visualizing seal and/or clot formation, for example, during or after surgical procedures, after catheter removal, etc. The present invention further provides methods for formation and optical detection of tissue seals or vasculature puncture closures as well as medical kits useful for the formation and optical detection of tissue seals or vasculature puncture closures.

20 Claims, 7 Drawing Sheets

Related U.S. Application Data division of application No. 13/266,161, filed as application No. PCT/US2010/032519 on Apr. 27, 2010, now Pat. No. 9,433,700.

(60) Provisional application No. 61/172,845, filed on Apr. 27, 2009.

(52) U.S. Cl.
CPC ......... *A61L 24/0042* (2013.01); *A61L 24/046* (2013.01); *A61L 24/106* (2013.01); *A61L 24/108* (2013.01); *A61L 2300/418* (2013.01); *A61L 2300/442* (2013.01); *A61L 2300/604* (2013.01); *A61L 2400/04* (2013.01); *A61L 2430/20* (2013.01); *A61L 2430/34* (2013.01)

(58) Field of Classification Search
CPC ................. A61L 24/046; A61L 24/108; A61L 2300/418; A61L 2300/442; A61L 2300/604; A61L 2400/04; A61L 2430/20; A61L 2430/34
See application file for complete search history.

(56) References Cited

U.S. PATENT DOCUMENTS

| | | |
|---|---|---|
| 4,427,650 A | 1/1984 | Stroetmann |
| 4,427,651 A | 1/1984 | Stroetmann |
| 4,511,478 A | 4/1985 | Nowinski et al. |
| 4,627,879 A | 12/1986 | Rose et al. |
| 4,714,457 A | 12/1987 | Alterbaum |
| 4,741,872 A | 5/1988 | DeLuca et al. |
| 4,826,945 A | 5/1989 | Cohn et al. |
| 4,852,568 A | 8/1989 | Kensey |
| 4,888,413 A | 12/1989 | Domb et al. |
| 4,890,612 A | 1/1990 | Kensey |
| 4,909,251 A | 3/1990 | Seelich |
| 4,928,603 A | 3/1990 | Rose et al. |
| 4,938,763 A | 7/1990 | Dunn et al. |
| 5,030,215 A | 7/1991 | Morse et al. |
| 5,100,992 A | 3/1992 | Cohn et al. |
| 5,160,745 A | 11/1992 | DeLuca et al. |
| 5,292,362 A | 3/1994 | Bass et al. |
| 5,318,782 A | 6/1994 | Weis-Fogh |
| 5,342,393 A | 8/1994 | Stack |
| 5,370,660 A | 12/1994 | Weinstein et al. |
| 5,410,016 A | 4/1995 | Hubbell et al. |
| 5,411,520 A | 5/1995 | Nash et al. |
| 5,527,864 A | 6/1996 | Suggs et al. |
| 5,585,007 A | 12/1996 | Antanavich et al. |
| 5,702,715 A | 12/1997 | Nikolaychik et al. |
| 5,827,265 A | 10/1998 | Glinsky et al. |
| 6,056,970 A | 5/2000 | Greenawalt et al. |
| 6,162,241 A | 12/2000 | Coury et al. |
| 6,180,085 B1 | 1/2001 | Achilefu et al. |
| 6,180,086 B1 | 1/2001 | Achilefu et al. |
| 6,180,087 B1 | 1/2001 | Achilefu et al. |
| 6,183,726 B1 | 2/2001 | Achilefu et al. |
| 6,190,641 B1 | 2/2001 | Achilefu et al. |
| 6,217,848 B1 | 4/2001 | Achilefu et al. |
| 6,228,344 B1 | 5/2001 | Dorshow et al. |
| 6,239,190 B1 | 5/2001 | Wilkinson et al. |
| 6,264,919 B1 | 7/2001 | Achilefu et al. |
| 6,264,920 B1 | 7/2001 | Achilefu et al. |
| 6,277,841 B1 | 8/2001 | Rajagopalan et al. |
| 6,280,703 B1 | 8/2001 | Combs et al. |
| 6,325,789 B1 | 12/2001 | Janzen et al. |
| 6,391,049 B1 | 5/2002 | McNally et al. |
| 6,395,257 B1 | 5/2002 | Achilefu et al. |
| 6,423,547 B1 | 7/2002 | Rajapopalan et al. |
| 6,461,871 B1 | 10/2002 | Kubista et al. |
| 6,492,494 B1 | 12/2002 | Cedarhold-Williams |
| 6,638,917 B1 | 10/2003 | Li et al. |
| 6,641,798 B2 | 11/2003 | Achilefu et al. |
| 6,656,451 B1 | 12/2003 | Achilefu et al. |
| 6,663,847 B1 | 12/2003 | Achilefu et al. |
| 6,669,926 B1 | 12/2003 | Achilefu et al. |
| 6,673,334 B1 | 1/2004 | Achilefu et al. |
| 6,685,730 B2 | 2/2004 | West et al. |
| 6,706,254 B2 | 3/2004 | Achilefu et al. |
| 6,716,413 B1 | 4/2004 | Achilefu et al. |
| 6,733,744 B1 | 5/2004 | Achilefu et al. |
| 6,761,878 B2 | 7/2004 | Achilefu et al. |
| 6,833,408 B2 | 12/2004 | Sehl et al. |
| 6,887,854 B2 | 5/2005 | Achilefu et al. |
| 6,939,532 B2 | 9/2005 | Achilefu et al. |
| 7,009,034 B2 | 3/2006 | Pathak et al. |
| 7,011,817 B2 | 3/2006 | Achilefu et al. |
| RE39,192 E | 7/2006 | MacPhee et al. |
| 7,073,510 B2 | 7/2006 | Redmond et al. |
| 7,077,839 B2 | 7/2006 | Hamblin et al. |
| 7,078,378 B1 | 7/2006 | Owen et al. |
| RE39,298 E | 9/2006 | MacPhee et al. |
| RE39,321 E | 10/2006 | MacPhee et al. |
| 7,128,896 B2 | 10/2006 | Achilefu et al. |
| 7,175,831 B2 | 2/2007 | Achilefu et al. |
| 7,198,778 B2 | 4/2007 | Achilefu et al. |
| 7,201,892 B2 | 4/2007 | Achilefu et al. |
| 7,230,088 B2 | 6/2007 | Rajagopalan et al. |
| 7,252,815 B2 | 8/2007 | Achilefu et al. |
| 7,297,325 B2 | 11/2007 | Achilefu et al. |
| 7,438,894 B2 | 10/2008 | Achilefu et al. |
| 7,468,177 B2 | 12/2008 | Achilefu et al. |
| 7,504,087 B2 | 3/2009 | Achilefu et al. |
| 7,510,700 B2 | 3/2009 | Achilefu et al. |
| 7,514,069 B2 | 4/2009 | Achilefu et al. |
| 7,556,797 B2 | 7/2009 | Achilefu et al. |
| 7,566,444 B2 | 7/2009 | Achilefu et al. |
| 7,608,244 B2 | 10/2009 | Achilefu et al. |
| 7,674,902 B2 | 3/2010 | Rajagopalan et al. |
| 7,758,861 B2 | 7/2010 | Rajagopalan et al. |
| 7,767,194 B2 | 8/2010 | Achilefu et al. |
| 7,790,144 B2 | 9/2010 | Achilefu et al. |
| 7,888,378 B2 | 2/2011 | Rajagopalan et al. |
| 2001/0047173 A1 | 11/2001 | Schlapfer et al. |
| 2002/0044909 A1 | 4/2002 | Achilefu et al. |
| 2002/0156117 A1 | 10/2002 | Achilefu et al. |
| 2003/0036538 A1 | 2/2003 | Rajagopalan et al. |
| 2003/0105299 A1 | 6/2003 | Achilefu et al. |
| 2003/0105300 A1 | 6/2003 | Achilefu et al. |
| 2003/0119985 A1* | 6/2003 | Sehl ................. A61L 27/24 525/54.1 |
| 2003/0143159 A1 | 7/2003 | Achilefu et al. |
| 2003/0152577 A1 | 8/2003 | Achilefu et al. |
| 2003/0158127 A1 | 8/2003 | Rajagopalan et al. |
| 2003/0165432 A1 | 9/2003 | Achilefu et al. |
| 2003/0185756 A1 | 10/2003 | Achilefu et al. |
| 2003/0202941 A1 | 10/2003 | Achilefu et al. |
| 2003/0236452 A1 | 12/2003 | Melker et al. |
| 2004/0044219 A1 | 3/2004 | Sandstrom et al. |
| 2004/0081622 A1 | 4/2004 | Achilefu et al. |
| 2004/0121011 A1 | 6/2004 | McKerracher |
| 2004/0132046 A1 | 7/2004 | Westman et al. |
| 2004/0141920 A1 | 7/2004 | Achilefu et al. |
| 2004/0180809 A1 | 9/2004 | Achilefu et al. |
| 2004/0202611 A1 | 10/2004 | Achilefu et al. |
| 2004/0202625 A1* | 10/2004 | Daniloff ................. A61L 27/50 424/63 |
| 2004/0213740 A1 | 10/2004 | Achilefu et al. |
| 2004/0220298 A1 | 11/2004 | Kozee et al. |
| 2004/0223913 A1 | 11/2004 | Achilefu et al. |
| 2004/0234454 A1 | 11/2004 | Achilefu et al. |
| 2004/0241095 A1 | 12/2004 | Achilefu et al. |
| 2004/0253182 A1 | 12/2004 | Achilefu et al. |
| 2005/0031542 A1 | 2/2005 | Achilefu et al. |
| 2005/0163715 A1 | 7/2005 | Achilefu et al. |
| 2005/0201939 A1 | 9/2005 | Achilefu et al. |
| 2005/0271592 A1 | 12/2005 | Achilefu et al. |
| 2005/0281741 A1 | 12/2005 | Achilefu et al. |
| 2006/0078536 A1 | 4/2006 | Kodokian et al. |
| 2006/0079599 A1 | 4/2006 | Arthur |
| 2006/0095102 A1 | 5/2006 | Perez |
| 2006/0148683 A1 | 7/2006 | McMurry et al. |

(56) References Cited

U.S. PATENT DOCUMENTS

| | | |
|---|---|---|
| 2006/0177457 A1 | 8/2006 | Rajagopalan et al. |
| 2007/0092450 A1 | 4/2007 | Achilefu et al. |
| 2007/0128115 A1 | 6/2007 | Achilefu et al. |
| 2007/0269368 A1 | 11/2007 | Achilefu et al. |
| 2007/0269373 A1 | 11/2007 | Achilefu et al. |
| 2008/0008655 A1 | 1/2008 | Achilefu et al. |
| 2008/0014602 A1 | 1/2008 | Nagano et al. |
| 2008/0056989 A1 | 3/2008 | Achilefu et al. |
| 2008/0060550 A1 | 3/2008 | MacDonald et al. |
| 2008/0139786 A1 | 6/2008 | Rajagopalan et al. |
| 2008/0233050 A1 | 9/2008 | Achilefu et al. |
| 2008/0275017 A1 | 11/2008 | Rajagopalan et al. |
| 2008/0281173 A1 | 11/2008 | Esenaliev et al. |
| 2008/0299038 A1 | 12/2008 | Rajagopalan et al. |
| 2008/0312539 A1 | 12/2008 | Dorshow et al. |
| 2009/0010851 A1 | 1/2009 | Rajagopalan et al. |
| 2009/0035363 A1 | 2/2009 | Rajagopalan et al. |
| 2009/0036502 A1 | 2/2009 | Rajagopalan et al. |
| 2009/0098073 A1* | 4/2009 | MacDonald ........ A61L 26/0066 424/63 |
| 2009/0198053 A1 | 8/2009 | Rajagopalan et al. |
| 2009/0263327 A1 | 10/2009 | Achilefu et al. |
| 2009/0304583 A1 | 12/2009 | Achilefu et al. |
| 2010/0010223 A1 | 1/2010 | Dorshow et al. |
| 2010/0021382 A1 | 1/2010 | Dorshow et al. |
| 2010/0022449 A1 | 1/2010 | Achilefu et al. |
| 2010/0105899 A1 | 4/2010 | Neumann et al. |
| 2010/0113756 A1 | 5/2010 | Rajagopalan et al. |
| 2010/0222547 A1 | 9/2010 | Rajagopalan et al. |
| 2010/0233091 A1 | 9/2010 | Neumann et al. |
| 2011/0130707 A1 | 6/2011 | Rajagopalan et al. |
| 2011/0177006 A1 | 7/2011 | Rajagopalan et al. |
| 2011/0177007 A1 | 7/2011 | Rajagopalan et al. |
| 2011/0196231 A1 | 8/2011 | Rajagopalan et al. |
| 2011/0257583 A2 | 10/2011 | Rajagopalan et al. |
| 2013/0116512 A1 | 5/2013 | Imran |
| 2015/0306486 A1 | 10/2015 | Logan et al. |
| 2016/0331862 A1* | 11/2016 | Basore ................ A61L 24/001 |

FOREIGN PATENT DOCUMENTS

| | | |
|---|---|---|
| JP | 199565 | 4/1989 |
| JP | 10191902 | 7/1998 |
| WO | 9104073 | 4/1991 |
| WO | 9522249 | 8/1995 |
| WO | 2007103250 | 9/2007 |
| WO | 2007149478 | 12/2007 |

OTHER PUBLICATIONS

Buxton et al. (2003), Circulation 108, 2737-42.
Dervan, P. et al. (2005), J. Am. Chem. Soc.127, 16685-16691.
DiBella et al. (1995), I Biol. Chem. 270, 163-169.
Egertsdotter et al. (2007), Biomed. Eng. 555.
Ellis-Behnke et al. (2006), PNAS 103(13), 5054-59.
Ellis-Behnke et al. (2006), Nanomedicine: Nanotechnology, Biology, and Medicine.
Fischer et al. (1996), Thrombosis Res. 81, 157-162.
Gerkens et al. (1999), Am. J. Cardiol. 83(12), 1658-63.
Goddard and Erikson (2009), "Bioconjusation techniques for microfluidic biosansors," Anal Bioanal Chem; DOI 10.1007/s00216-009-2731-y.
Growth Factors and Other Aspects of Wound Healing: Biological and Clinical Applications, Alan R. Liss, Inc. New York, NY, 303-29 (1988).
Hartgerink et al. (2001), Science 294, 1684-88.
Karges and Metzner (1996), Seminars in Thrombosis and Hemostasis 22, 427-436.
Lai et al. (1994), J. Biol Chem. 269, 24596-24601.
Lee et al. (2005), Nature Biotechnology 23, 1517-26.
Lewis et al. (1997), Biochemistry 36, 995-1002.
Lord et al. (1993), Blood Coagulation and Fibrinolysis 4, 55-59.
Nakayama, Yasuhide et al. (2007), "Heparin Bioconjugate with a Thermoresponsive Cationic Branched Polymer: A Novel Aqueous Antithrombogenic Coating Material," Langmuir, 23(15), 8206-8211.
Nygaard et al. (2001), Catheterization and Cardiovascular Interventions 52, 3-7.
Oh et al. (2008), "The development of microgels/nanogels for drug delivery applications," Prog. Polym. Sci. 33, 448-477.
Prunkard et al. (1996), Nature Biotechnology 14, 867-871.
Radosevich et al. (1997), "Fibrin Sealant: Scientific rationale, production methods, properties, and current clinical use," Vox Sang 72, 133-143.
Ruygrok et al. (2005), Catheterization and Cardiovascular Interventions 66, 185-191.
Shaunak et al. (2004), Nature Biotechnology 22(8), 977-84.
Sontjens et al. (2006), Biomacromolecules 7, 310-16.
Svanvik et al. (2000), Anal. Biochem. 281, 26-35.
Tian et al. (2006), Chem Med Chem 2(1), 129-36.
Yu, M. et al. (2005), J. Am. Chem. Soc. 127, 4130-4131.
International Search Report dated May 12, 2011, for International Application No. PCT/US2010/032519, 6 pages.
Written Opinion of the International Searching Authority dated Oct. 27, 2011, for International Application No. PCT/US2010/032519, 12 pages.
Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.
Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.
Dean et al., "Inulin, Diodone, Creatinine and Urea Clearances in Newborn Infants," J. Physiol., vol. 106, (1947), pp. 431-439.
Debreczeny et al., "Transdermal Optical Renal Function Monitoring in Humans: Development, Verification, and validation of a Prototype Device," Journal of Biomedical Optics, vol. 23, No. 5, (May 2018), pp. 057003-1-057003-9.
Friedman et al., "A comparison of the renal clearances of allantoin and inulin in man," Fed. Proc., vol. 7, No. 1 Pt 1, (1948), 1 page.
Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.
Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.
Nagpal et al., "Combined Fluorescein, Indocyanine angiography and Optical Coherent Tomography Using Spectralis," Rajasthan Journal of Ophthalmology, (2011), 8 pages.
Navar et al., "Distal Tubular Feedback in the Autoregulation of Single Nephron Glomerular Filtration Rate," J. Clin. Invest., vol. 53, (1974), pp. 516-525.
Nicholson et al., "Renal Function as Affected by Experimental Unilateral Kidney Lesions: I. Nephrosis Due to odium Rartrate," J. Exp. Med., vol. 68, (1938), pp. 439-456.
Pill et al., "Fluorescein-labeled Sinistrin as Marker of Glomerular Filtration Rate," European Journal of Medicinal Chemistry, vol. 40, (2005), pp. 1056-1061.
Poujeol et al., "Glomerular Filtration Rate and Microsphere Distributions in Single Nephron of Rat Kidney," Pflugers Arch., vol. 357, (1975), pp. 291-301.
Robson et al., "The Determination of the Renal Clearance of Inulin in Man," Q. J. Exp. Physiol., vol. 35, (1949), pp. 111-134.
Schock-Kusch et al., "Transcutaneous measurement of glomerular filtration rate using FITC-sinistrin in rats," Nephrol Dial Transplant, vol. 24, (2009), pp. 2997-3001.
Shannon et al., "The Renal Excretion of Inulin and Creatinine by the Anaesthetized Dog and the Pump-Lung-Kidney Preparation", J. Physiol., vol. 98, (1940), pp. 97-108.

(56) References Cited

OTHER PUBLICATIONS

Yu et al., "Rapid determination of renal filtration function using an optical ratiometric imaging approach," Am. J. Physiol. Renal. Physiol., vol. 292, (2007), pp. F1873-F1880.
International Search Report received for PCT Patent Application No. PCT/US2019/013784, dated May 7, 2019, 6 pages.
International Preliminary Report on Patentability received for PCT Patent Application No. PCT/US2019/013784, dated Jul. 30, 2020, 8 pages.

* cited by examiner

TISSUE SEALANT COMPOSITIONS, VASCULAR CLOSURE DEVICES, AND USES THEREOF

CROSS-REFERENCES TO RELATED APPLICATIONS

This application is a divisional of U.S. application Ser. No. 15/223,240, filed Jul. 29, 2016, which is a divisional of U.S. application Ser. No. 13/266,161 (issued as U.S. Pat. No. 9,433,700), filed Oct. 25, 2011, which is a 371 national phase entry of PCT/US2010/32519, filed Apr. 27, 2010, which claims the benefit of U.S. Provisional Application No. 61/172,845, filed Apr. 27, 2009, each of which are hereby incorporated by reference in their entirety.

BACKGROUND

The present invention generally relates to tissue sealant compositions and vascular closure devices incorporating optical dyes for use in medical procedures and methods, for example, for monitoring and enhancing hemostatic sealing of non-suture arterial closure devices.

Blood loss is a concern for trauma and wound treatment and more generally during and after many medical procedures. An important goal is facilitating hemostasis (e.g., arrest of bleeding), by the physiological properties of vasoconstriction or coagulation and/or by surgical means. Conventional techniques to control bleeding and repair wounds include electrocautery, application of pressure, suturing, and stapling.

Millions of interventional diagnostic procedures are performed annually worldwide. As an example, several million coronary angiograms are performed for diagnostic or other purposes. See, e.g., Ruygrok et al., Catheterization and Cardiovascular Interventions 66, 185-91, (2005). Femoral artery puncture provides vascular access for such catheter procedures in the majority of patients. Following removal of the catheter device, hemostasis is commonly achieved by a period of manual compression and prolonged immobilization. This often involves specialized nursing units, and can be a strain on hospital resources. It may also be a source of inconvenience and discomfort for the patient.

A number of studies have shown that simple manual compression (e.g., with a sandbag or other external compression device) may result in complications at or near the puncture site (e.g. in the groin region). See, e.g., Gerkens et al., Am. J. Cardiol. 83(12), 1658-63, (1999). Serious complications may result, including arterial pseudoaneurysms (with rupture), arteriovenous fistulae, acute arterial occlusion, and/or infection.

Suture mediated and non-suture mediated compositions, devices, and methods to facilitate wound or puncture treatment and hemostasis have been developed and employed over the past twenty years. Hemostatic agents and tissue sealants, in general, operate to stop bleeding by mechanically closing defects in tissue and/or by augmenting the mammalian coagulation cascade. These compositions and/or devices may operate as a form of mechanical barrier, plug, or patch to close the vessel or other puncture site and/or may supplement the natural hemostatic process. A number of non-suture mediated compositions and devices are in use or in clinical trials in the United States. Collagen plugs are exemplary of these compositions and devices, and are applied and held in place by a variety of different mechanisms. See, e.g., Nygaard et al., Catheterization and Cardiovascular Interventions 52, 3-7, (2001). Failures and complications from such compositions and devices are generally minor and may occur, for example, by improper placement of the plug.

As will be generally recognized from the foregoing, a need currently exists for tissue sealants and closure devices for biomedical applications. Specifically, tissue sealants and closure devices are needed that provide enhanced functionality for wound or puncture treatment and for establishing and maintaining hemostasis.

SUMMARY

The present invention provides compositions, therapeutic agents and devices, including tissue sealant compositions, vasculature closure devices and optical agents, useful for therapeutic procedures involving occlusion, closure, and/or treatment of an opening in biological tissue, including vasculature tissue such as blood vessel tissue. The compositions and methods of the invention, for example, enable effective in vivo administration and optical evaluation of tissue sealants and/or devices for closing an arterial puncture or vasculature access site. Tissue sealants and closure devices of the invention include an optical dye component enabling optically sensing, detecting and monitoring processes involved with occlusion and/or treatment of a vasculature opening, for example via tissue sealing, coagulation and/or clot formation processes. In some aspects, for example, tissue sealants and devices of the invention comprise an optical dye which undergoes an observable change as the sealant and/or device is immobilized and/or incorporated into a tissue seal, clot, fibrin network and/or synthetic polymer network, for example a observable change in luminescence, and/or fluorescence quantum yield and/or a change in visual color, including a change in emission and/or absorption wavelengths. In some aspects, tissue sealants and vasculature closure devices of the present invention are useful for visualizing a seal, clot, fibrin network formation and/or synthetic polymer network, for example, for treatment of a vasculature puncture or access site during or after surgical procedures, e.g., after catheter device removal, etc. The present invention further provides methods for formation and optical detection of tissue seals or vasculature puncture closures as well as medical kits useful for the formation and optical evaluation of tissue seals or vasculature closures.

In an aspect, the invention provides optically functional tissue sealants for visualizing, detecting and/or evaluating formation of a clot, fibrin network, synthetic polymer network or tissue seal. The invention provides a tissue sealant comprising an adhesive material that is activated to form a seal when contacted with a biological tissue; and an optical dye covalently bonded to or noncovalently associated with the adhesive material, wherein the optical dye exhibits a first optical condition prior to activation of the adhesive material and exhibits a second optical condition that is distinguishable from the first optical condition after activation of the adhesive material. In an embodiment, the optical dye is covalently bonded to the adhesive material of the tissue sealant. Tissue sealants of this aspect are useful for in vivo administration and/or treatment of a range of biological tissues, including vascular tissue, such as blood vessels including arteries, veins, arterioles, capillaries, and venules. Activation of the adhesive material component of the tissue sealant may be initiated in situ by natural processes, such as clotting and coagulation processes, or by application of an external stimulus. In some embodiments, the tissue sealant comprises a plurality of optic dyes bound to or noncovalently associated with the adhesive.

As used herein, "adhesive material" refers to a composition, or mixture of compositions, that at least partially forms a seal or other barrier in, or on, a biological tissue upon activation. In some embodiments, for example, an adhesive material of the invention forms a tissue seal, a fibrin network, synthetic polymer network, or a clot in, or on, an opening in a biological tissue upon activation, such as a wound site, vasculature access site, or vascular puncture. Adhesive materials in some tissue sealants are compositions that undergo polymerization and/or polymer cross linking reactions upon activation so as to form a seal or other barrier in, or on, a biological tissue upon activation. Adhesive materials in some tissue sealants are capable of adhering to, or otherwise binding to, biological tissues, such as vascular tissue, upon activation, for example, to facilitate formation and/or maintenance of a seal or other barrier in, or on, a biological tissue. In some embodiments, adhesive materials undergo associative interactions with each other and/or biological tissues upon activation, including covalent bonding, hydrogen bonding, dipole-dipole interactions and/or Van der Waals interactions, so as to form and/or maintain a seal or other barrier in, or on, a biological tissue. In some embodiments, activation of the adhesive material comprises formation of a tissue seal, a fibrin network, synthetic polymer network, a clot or other mechanical barrier by natural processes, such as by initiation a coagulation cascade in a subject, and/or by natural or non-natural processes involving polymer formation and/or cross linking reactions, including formation of a fibrin network or a synthetic polymer network. In some embodiments, for example, a tissue seal is formed in situ via formation of a synthetic polymer network by chemical reactions cross linking a polymer component(s) of the adhesive material and/or polymer formation reactions of a monomer component of the adhesive material. Activation in some embodiments refers to a process wherein the adhesive material undergoes polymer formation and/or cross linking reactions, thereby resulting in a clot or tissue seal, for example by natural coagulation processes or via in situ formation and/or cross linking of a synthetic polymer network. In some embodiments, activation of the adhesive material initiates physical and/or chemical changes in the optical dye component, thereby providing a change from a first optical condition to second an optical condition. In an embodiment, for example, activation of the adhesive material incorporates the optical dye into the tissue seal, fibrin network, synthetic polymer network or clot, thereby providing the change from the first optical condition to the second optical condition. In an embodiment, for example, activation of the adhesive material immobilizes the optical dye in the tissue seal, fibrin network, synthetic polymer network or clot, thereby providing the change from the first optical condition to the second optical condition. In an embodiment, for example, activation of the adhesive material rigidifies the optical dye, thereby providing a change from the first optical condition to the second optical condition. in the context of the present description, the term rigidifies refers to physical or chemical processes that reduce the extent of molecular motion (e.g., free rotation, vibration, etc.) available to the dye, for example by a process that at least partially binds the dye or holds the dye in a sterically constrained environment (e.g., at least partially binding the optical agent to a clot, collagen network or synthetic polymer network), such as reactions that tether or otherwise immobilize the optical dye.

In another aspect, the invention is directed to optically functional vasculature closure devices for optical visualization, assessment and/or evaluation during administration and use. The invention provides a vascular closure device comprising a plug for at least partially occluding an opening in a vasculature tissue; and an optical dye covalently bound to or noncovalently associated with the plug, wherein the optical dye exhibits a first optical condition when the plug is in a first state prior to occluding the opening in the vasculature tissue and exhibits a second optical condition that is distinguishable from the first optical condition when the plug is in a second state upon at least partially occluding the opening in the vasculature tissue. In an embodiment, the optical dye is covalently bound to the plug component of the closure device. In some embodiments, the closure device comprises a plurality of optic dyes covalently bound to or noncovalently associated with the plug. Closure devices of this aspect are useful for in vivo administration to and/or treatment of a range of tissues, including vascular tissue, such as blood vessels including arteries, veins, arterioles, capillaries, and venules. Activation of the plug component of the closure device so as to at least partially occlude an opening in a vasculature tissue may be initiated in situ by natural processes, such as clotting and coagulation processes, or by application of an external stimulus. In some embodiments, the vascular closure device further comprises one or more tissue sealant components, such as tissue sealants known in the art and optically functional tissue sealants described herein.

As used herein, partially occluding an opening in a vasculature tissue refers to administration of the closure device such that it provides an at least partial mechanical barrier to a vasculature opening. At least partially occluding a vasculature opening may be achieved via a range of clinical techniques that involve contacting vasculature tissue with a closure device of the present invention, for example, via physical contact, implantation, insertion or application of the closure device with or into an arterial puncture, vasculature access site or wound. Occluding a vasculature opening via administration of a closure device may optionally involve formation of a fibrin network, synthetic polymer network, clot or tissue seal, for example by natural coagulation processes or via in situ formation and/or cross linking of a synthetic polymer network. In an embodiment of this aspect, occluding the opening in the vasculature tissue incorporates the optical dye into a tissue seal, fibrin network, synthetic polymer network or clot formed upon administration of the closure device, thereby providing a change from the first optical condition to the second optical condition. In an embodiment of this aspect, occluding the opening in the vasculature tissue immobilizes the optical dye, for example in a tissue seal, fibrin network, synthetic polymer network or clot formed upon administration of the closure device, thereby providing a change from the first optical condition to the second optical condition. In an embodiment of this aspect, occluding the opening in the vasculature tissue rigidifies the optical dye, thereby providing a change from the first optical condition to the second optical condition.

Optical dyes in the present tissue sealants and closure devices may exhibit a range of optical conditions that are distinguishable upon activation of the adhesive material or at least partial occlusion of a vasculature opening. In some tissue sealants and closure devices, the first and second optical conditions of the optical dye refer to first and second states of an optical property that undergoes a change upon activation of the adhesive material or at least partial occlusion of a vasculature opening. As used herein, distinguishable first and second optical conditions refers to optical states and/or properties for which a change upon activation of adhesive material or at least partial occlusion of a vasculature opening can be sensed, detected and/or measured, for example, visually or using an optical detection system, such as an optical imaging system or other optical sensor or probe (e.g., a photomultiplier tube, photodiode, photodiode array, charge coupled device, phosphorescent screen, CMOS detector, etc.). Preferably for some applications of the present invention, optical condition refers generally to one or more optical properties or parameters relating to luminescence, for example fluorescence, phosphorescence, chemiluminescence, and/or optoacoustics. In an embodiment, the first and second optical conditions of the optical dye refer to absorbance, fluorescence, color, reflectance, scattering or an optoacoustic condition. In an embodiment, for example, the first and second optical conditions of the optical dye refer to first and second states of an optical property selected from the group consisting of fluorescence quantum yield, fluorescence excitation wavelength, distribution of fluorescence excitation wavelengths, emission wavelength, distribution of emission wavelengths, absorption maxima, distribution of absorption wavelengths and Stokes shift. In some of the present tissue sealants and closure devices, for example, the optical dye undergoes an observable change in the color and/or intensities of fluorescence observed upon optical excitation after activation of the adhesive material or at least partial occlusion of a vasculature opening. This change in color or intensity of fluorescence, for example, can be used to identify or evaluate the condition, physical dimensions, degree of coverage, extent of activation, and location of the tissue sealant or closure device relative to an arterial puncture, vasculature access site or wound. This aspect of the present invention provides enhanced functionality for administration of tissue sealants and closure devices, and provides a useful means of optically monitoring and assessing the real time effectiveness of a tissue sealant or closure device during and after administration and/or the physical dimensions or completeness of the tissue seal or blockage.

In an embodiment, the first optical condition of the optical dye is a first fluorescence quantum yield prior to activation of the adhesive material or at least partial occlusion of a vasculature opening, and the second optical condition of the optical dye is a second fluorescence quantum yield after activation of the adhesive material or at least partial occlusion of a vasculature opening, wherein the second fluorescence quantum yield is different from the first fluorescence quantum yield. In a tissue sealant, for example, the first fluorescence quantum yield of the optical dye is substantially equal to 0, such as a quantum yield less than 0.01 or optionally less than 0.001, or optionally less than 0.0001, and the second fluorescence quantum yield is greater than or equal to 0.01, or optionally greater than or equal to 0.1. In an embodiment of this aspect, for example, the optical dye substantially does not measurably fluoresce (e.g., a fluorescence intensity not detectable visually by the eye or in some embodiments a fluorescence intensity not detectable using an optical sensor or imaging device) when exposed to excitation light of a particular wavelength prior to activation of the adhesive material or at least partial occlusion of a vasculature opening, but the optical dye emits measurable fluoresce (e.g., a fluorescence intensity detectable visually by the eye or in some embodiments a fluorescence intensity detectable using an optical sensor or imaging device) upon excitation after the adhesive material has been activated or upon at least partial occlusion of a vasculature opening, for example by coagulation, clot formation, formation of a tissue seal, administration of a closure device, etc. Alternatively, the invention includes systems wherein the optical dye fluoresces when exposed to light of a particular wavelength prior to activation of the adhesive material or at least partial occlusion of a vasculature opening, but the optical dye does not measurably fluoresce after the adhesive material has been activated or upon at least partial occlusion of a vasculature opening, for example by coagulation, clot formation, formation of a tissue seal, administration of a closure device, etc. In an embodiment, the second fluorescence quantum yield is greater than the first fluorescence quantum yield by a factor of 1.5, optionally for some embodiments by a factor of 10, optionally for some embodiments by a factor of 100, and optionally for some embodiments by a factor of 1000. In an embodiment, the second fluorescence quantum yield is less than the first fluorescence quantum yield by a factor of 1.5, optionally for some embodiments by a factor of 10, optionally for some embodiments by a factor of 100, and optionally for some embodiments by a factor of 1000.

In an embodiment, the first optical condition of the optical dye is a first emission wavelength or distribution of emission wavelengths prior to activation of the adhesive material or occlusion of the vasculature opening and the second optical condition of the optical dye is a second emission wavelength or distribution of emission wavelengths after activation of the adhesive material or occlusion of the vasculature opening, wherein the second emission wavelength or distribution of emission wavelengths is different from the first emission wavelength or distribution of emission wavelengths. In a tissue sealant or closure device, for example, the second emission wavelength is greater than the first emission wavelength by at least 5 nanometers, optionally at least 10 nanometers, optionally by at least 20 nanometers, or wherein at least a portion of the second distribution of emission wavelengths is greater than at least a portion of the first distribution of emission wavelengths by at least 5 nanometers, optionally at least 10 nanometers, optionally by at least 20 nanometers. In a tissue sealant or closure device, for example, the second emission wavelength is less than the first emission wavelength by at least 5 nanometers, optionally at least 10 nanometers, optionally by at least 20 nanometers, or wherein at least a portion of the second distribution of emission wavelengths is less than at least a portion of the first distribution of emission wavelengths by at least 5 nanometers, optionally at least 10 nanometers, optionally by at least 20 nanometers.

In an embodiment, the first optical condition of the optical dye is a first absorption wavelength corresponding to an absorption maximum in the visible or near infrared regions of the electromagnetic spectrum prior to activation of the adhesive material and the second optical condition of the optical dye is a second absorption wavelength corresponding to an absorption maximum in the visible or near infrared regions of the electromagnetic spectrum after activation of the adhesive material, wherein the second absorption wavelength is different from the first absorption wavelength. In an embodiment, the second absorption wavelength is greater than the first absorption wavelength by at least 10 nanometers, optionally for some embodiments by at least 20 nanometers and optionally for some embodiments by at least 40 nanometers. In an embodiment, the second absorption wavelength is less than the first absorption wavelength by at least 10 nanometers, optionally for some embodiments by at least 20 nanometers and optionally for some embodiments by at least 40 nanometers.

In an embodiment, the optical dye exhibits an optoacoustic property that undergoes a change from a first condition to a second condition upon activation of the adhesive material or occlusion of the vasculature opening. In an embodiment, for example, an optical dye of the tissue sealant or closure device emits ultrasound upon exposure to light prior to prior to activation of the adhesive material or at least partial occlusion of a vasculature opening, but loses this optoacoustic property after activation of the adhesive material or at least partial occlusion of a vasculature opening. In an embodiment, for example, an optical dye of the tissue sealant or closure device does not emit ultrasound upon exposure to light prior to prior to activation of the adhesive material or at least partial occlusion of a vasculature opening, but emits ultrasound upon exposure to light after activation of the tissue sealant or at least partial occlusion of a vasculature opening.

The adhesive materials useful in tissue sealants of the present invention are generally designed to be activated to form a seal at least when in physical contact with biological tissue, for example resulting in formation of a tissue seal clot, fibrin network or synthetic polymer network. Optionally, adhesive materials can under go activation when contacted with one or more initiators (e.g., chemical reagents that initiate or promote activation) or when exposed to an external stimulus, such as electromagnetic radiation, heat, chemical initiators, etc. Adhesive materials in some embodiments comprise one or more of collagen, denatured collagen (i.e., gelatin), oxidized cellulose, fibrin, fibrinogen, fibronectin, prothrombin, thrombin, thromboplastin, factor V, factor X, factor XIII, a source of calcium ions, a coagulation factor, a platelet factor, a coagulation activator, a platelet activator, a vasoconstrictor, a fibrinolysis inhibitor, a crosslinker, a glycosaminoglycan, a polysaccharide, a growth factor, or one or more natural and synthetic polymers, such as ionically, covalently, or hydrogen-bond crosslinked polymers. Polymers for adhesive materials include biopolymers and synthetic polymer such as chitin, chitosan, alginate, pectin, carboxymethylcellulose, and poloxamers such as Pluronic™, surfactants a polycyanoacrylate or monomers thereof, a polyethylene glycol polymer or monomers thereof, a succinimide-derivatized polyethylene glycol or monomers thereof, a thiol-derivatized polyethylene glycol or monomers thereof, a polyisocyanate or monomers thereof, a polyacrylate or monomers thereof, a polyamine or monomers thereof, a polyamide or monomers thereof, a polyurethane or monomers thereof, or any combination thereof. In an embodiment, the adhesive material is collagen, denatured collagen (i.e., gelatin), oxidized cellulose, fibrin, or fibrinogen. Adhesive materials of tissue sealants of the present invention may be covalently bonded to or noncovalently associated with a plurality of optical dyes having the same or different compositions.

The plug component of the present closure devices is generally designed to form an at least partial mechanical barrier when administered to the site of an opening in a vasculature tissue (e.g., physically contacted with the biological tissue), for example resulting in closure a vasculature opening. Optionally, closure devices, including plug components thereof, can optionally undergo activation via natural processes, such as upon physical contact with vasculature tissue, and/or upon exposure to external stimulus, such as exposure to one or more initiators, electromagnetic radiation, one or more chemical initiators, or heat, for example resulting in formation of a tissue seal, clot, fibrin network or synthetic polymer network. Plugs of closure devices in the present closure devices may comprise one or more of: collagen, fibrin, fibrinogen, fibronectin, prothrombin, thrombin, thromboplastin, factor V, factor X, factor XIII, a source of calcium ions, a coagulation factor, a platelet factor, a coagulation activator, a platelet activator, a vasoconstrictor, a fibrinolysis inhibitor, a crosslinker, a glycosaminoglycan, a polysaccharide, a cyanoacrylate, a growth factor, a dendrimer, a nanoparticle, or any combination thereof. Plugs of closure devices of the present invention may be covalently bonded to or noncovalently associated with a plurality of optical dyes having the same of different compositions. Optionally, closure devices of the present invention may comprise a tissue sealant component, for example to facilitate occlusion of a vasculature opening, such as an arterial puncture, vasculature access site or wound.

In an embodiment, the optical dye is covalently bound to the adhesive material or plug, for example via one or more covalent bonds linking the optical dye and the adhesive material or plug. Alternatively, the invention provides tissue sealants and closure devices wherein the optical dye is not covalently bound to the adhesive material or plug. For example, the invention provides tissue sealants and closure devices wherein the optical dye is in physical contact with, but not covalently bound to, the adhesive material or plug. The invention provides tissue sealants and closure devices wherein the optical dye is mixed with, but not covalently bound to, the adhesive material or plug, for example compositions wherein the optical dye is uniformly mixed with, but not covalently bound to, the adhesive material or plug.

Selection of the composition optical dye component is important in the present tissue sealants and closure devices, as this component determines, at least in part, the nature and extent of the change in optical condition observed upon activation of the adhesive material or occlusion of the opening in the vasculature tissue. In an embodiment, the optical dye of the tissue sealant or closure device is a molecule or a functional group corresponding to a pyrazine, a thiazole, a phenylxanthene, a phenothiazine, a phenoselenazine, a cyanine, an indocyanine, a squaraine, a dipyrrolo pyrimidone, an anthraquinone, a tetracene, a quinoline, an acridine, an acridone, a phenanthridine, an azo dye, a rhodamine, a phenoxazine, an azulene, an azaazulene, a triphenyl methane dye, an indole, a benzoindole, an indocarbocyanine, a Nile Red dye, a thionin dye, an isosulfan blue dye or a benzoindocarbocyanine. As used throughout the present description, the expression "a group corresponding to" an indicated species expressly includes a group (including a monovalent or divalent group), for example an aromatic fluorophore or heterocyclic aromatic fluorophore, of the species or group of species provided in a covalently bonded configuration, optionally with one or more substituents, such as electron donating groups and/or electron withdrawing groups. Optical dyes particularly attractive for some applications include pyrazine-containing dyes, thionin dyes and thiazole-containing dyes. In an embodiment, the present invention provides a tissue sealant or closure device wherein the optical dye is non-covalently associated with, and not covalently bound to, the adhesive material or plug. Alternatively, the present invention includes tissue sealants or closure devices wherein the optical dye is covalently bound to the adhesive material or plug, for example via one or more connecting groups.

In an embodiment, a tissue sealant or closure device of the present invention comprises a pyrazine-containing optical dye. In an embodiment, for example, the invention provides a tissue sealant or closure device wherein the optical dye has the formula:

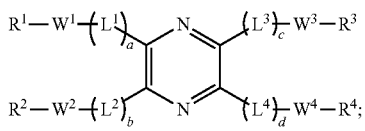
(FX1)

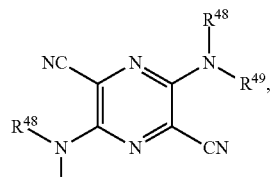
(FX2)

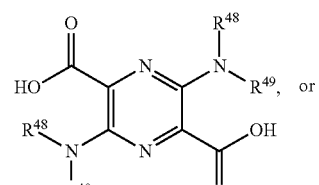
(FX3)

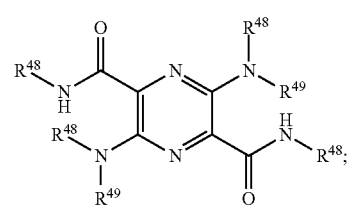
(FX4)

wherein each of $L^1$, $L^2$, $L^3$, and $L^4$, if present, is independently $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, or phenylene;

each of $W^1$, $W^2$, $W^3$, and $W^4$ is independently a single bond, —$(CH_2)_n$—, —$(HCCH)_n$—, —$(CH_2CH_2O)_r$—, —$(CHOH)_s$—, —O—, —S—, —SO—, —$SO_2$—, —$SO_3$—, —$OSO_2$—, —$NR^{13}$—CO—, —COO—, —OCO—, —OCOO—, —$CONR^{14}$—, —$NR^{15}CO$—, —$OCONR^{16}$—, —$NR^{17}COO$—, —$NR^{18}CONR^{19}$—, —$NR^{20}CSNR^{21}$—, —$(CH_2)_mO(CH_2)_n$—, —$(CH_2)_mS(CH_2)_n$—, —$(CH_2)_mSO(CH_2)_n$—, —$(CH_2)_m SO_2(CH_2)_n$—, —$(CH_2)_mSO_3(CH_2)_n$—, —$(CH_2)_mOSO_2(CH_2)_n$—, —$(CH_2)_mNR^{22}(CH_2)_n$—, —$(CH_2)_mCO(CH_2)_n$—, —$(CH_2)_mCOO(CH_2)_n$—, —$(CH_2)_mOCO(CH_2)_n$—, —$(CH_2)_mOCOO(CH_2)_n$—, —$(CH_2)_mCONR^{23}(CH_2)_n$—, —$(CH_2)_mNR^{24}CO(CH_2)_n$—, —$(CH_2)_mOCONR^{25}(CH_2)_n$—, —$(CH_2)_mNR^{26}COO(CH_2)_n$—, —$(CH_2)_mNR^{27}CONR^{28}(CH_2)_n$—, —$(CH_2)_mNR^{29}CSNR^{30}(CH_2)_n$—, —$(CH_2)_mO(CH_2)_nNR^{31}CO(CH_2)_n$—, —$(CH_2)_mCO(CH_2)_n(CH_2OCH_2)_q(CH_2)_nNR^{32}(CH_2)_nNR^{33}CO(CH_2)_n$—, or —$(CH_2)_mCO(CH_2)_nNR^{34}CO(CH_2)_n$—;

each of $R^1$, $R^2$, $R^3$, and $R^4$ is independently a hydrogen, —$OCF_3$, $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, —$CO_2R^{40}$, —$SOR^{41}$, —$OSR^{42}$, —$SO_2OR^{43}$, —$CH_2(CH_2OCH_2)_rCH_2OH$, —$PO_3R^{44}R^{45}$, —$OR^{46}$, —$SR^{47}$, —$NR^{48}R^{49}$, —$NR^{50}COR^{51}$, —CN, —$CONR^{52}R^{53}$, —$COR^{54}$, —$NO_2$, —$SO_2R^{55}$, —$PO_3R^{56}R^{57}$, —$SO_2NR^{58}R^{59}$, —$CH_2(CHOH)_rR^{60}$, or —$(CH_2CH_2O)_sR^{61}$;

each of r and a is independently an integer selected from the range of 1 to 100;

each of n, m and q is independently an integer selected from the range of 0 to 10;

each of a, b, c and d is independently 0 or 1; and each of $R^{13}$-$R^{34}$ is independently hydrogen, $C_1$-$C_{20}$ alkyl, $C_1$-$C_{20}$ cycloalkyl, $C_5$-$C_{20}$ aryl, $C_5$-$C_{20}$ heteroaryl, or $C_1$-$C_{20}$ acyl;

each of $R^{40}$-$R^{61}$ is independently hydrogen or $C_1$-$C_{10}$ alkyl. In an embodiment, a tissue sealant or closure device of the invention has an optical dye being of formula (FX1), wherein each of $R^1$-$R^4$ is independently hydrogen, $C_1$-$C_{10}$ alkyl or $C_3$-$C_{10}$ cycloalkyl, optionally wherein each of $R^1$-$R^4$ is independently hydrogen or $C_1$-$C_{10}$ alkyl, and optionally wherein each of $R^1$-$R^4$ is hydrogen. In an embodiment, a tissue sealant or closure device of the invention has an optical dye being of formula (FX1), wherein each of a, b, c, and d is equal to 0 (i.e., $L^1$-$L^4$ is not present), and optionally at least one of, and optionally all of, $W^1$-$W^4$ is a single bond. In an embodiment, for example, the invention provides a tissue sealant or closure device wherein the optical dye has the formula:

wherein $R^{48}$ and $R^{49}$ are as provided in the description of formula (FX1). In an embodiment, a tissue sealant or closure device of the invention has an optical dye being of formula (FX2)-(FX4), wherein each of $R^{48}$ and $R^{49}$ is independently hydrogen, $C_1$-$C_{10}$ alkyl or $C_3$-$C_{10}$ cycloalkyl, optionally wherein each of $R^{48}$ and $R^{49}$ is independently hydrogen or $C_1$-$C_5$ alkyl, and optionally wherein each of $R^{48}$ and $R^{49}$ is hydrogen.

In an embodiment, a tissue sealant or closure device of the present invention comprises a pyrazine-containing optical dye having an extended π-system. In an embodiment, for example, the invention provides a tissue sealant or closure device wherein the optical dye has the formula:

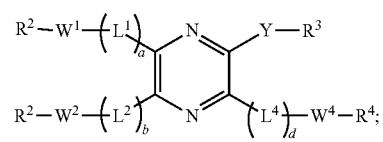
(FX5)

wherein

Y is —Ar—, —$C(R^{65})$=$C(R^{66})$—Ar—, —C≡C—Ar—, —N=N—Ar—, —CO—Ar—, —$N(R^{67})$—Ar—, —O—Ar—, —S—Ar—, —SO—Ar—, —$SO_2$—Ar—, —$C(R^{68})$=$C(R^{69})$—, or —C≡C—;

each of $L^1$, $L^2$, and $L^4$, if present, is independently $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, or phenylene;

each of $W^1$, $W^2$, and $W^4$ is independently a single bond, —$(CH_2)_n$—, —$(HCCH)_n$—, —$(CH_2CH_2O)_r$—, —$(CHOH)_s$—, —O—, —S—, —SO—, —$SO_2$—, —$SO_3$—, —$OSO_2$—, —$NR^{13}$—, —CO—, —COO—, —OCO—, —OCOO—, —$CONR^{14}$—, —$NR^{16}CO$—, —$OCONR^{16}$—, —$NR^{17}COO$—, —$NR^{18}CONR^{19}$—, —$NR^{20}CSNR^{21}$—, —$(CH_2)_mO(CH_2)_n$—, —$(CH_2)_mS(CH_2)_n$—, —$(CH_2)_mSO(CH_2)_n$—, —$(CH_2)_m SO_2(CH_2)_n$—, —(CH$_2$)$_m$SO$_3$(CH$_2$)$_n$—, —(CH$_2$)$_m$OSO$_2$(CH$_2$)$_n$—, —(CH$_2$)$_m$NR$^{22}$(CH$_2$)$_n$—, —(CH$_2$)$_m$CO(CH$_2$)$_n$—, —(CH$_2$)$_m$COO(CH$_2$)$_n$—, —(CH$_2$)$_m$OCO(CH$_2$)$_n$—, —(CH$_2$)$_m$OCOO(CH$_2$)$_n$—, —(CH$_2$)$_m$CONR$^{23}$(CH$_2$)$_n$—, —(CH$_2$)$_m$NR$^{24}$CO(CH$_2$)$_n$—, —(CH$_2$)$_m$OCONR$^{25}$(CH$_2$)$_n$—, —(CH$_2$)$_m$NR$^{26}$COO(CH$_2$)$_n$—, —(CH$_2$)$_m$NR$^{27}$CONR$^{28}$(CH$_2$)$_n$—, —(CH$_2$)$_m$NR$^{29}$CSNR$^{30}$(CH$_2$)$_n$—, —(CH$_2$)$_m$O(CH$_2$)$_n$NR$^{31}$CO(CH$_2$)$_n$—, —(CH$_2$)$_m$CO(CH$_2$)$_n$(CH$_2$OCH$_2$)$_q$(CH$_2$)$_n$NR$^{32}$(CH$_2$)$_n$NR$^{33}$ CO(CH$_2$)$_n$—, or —(CH$_2$)$_m$CO(CH$_2$)$_n$NR$^{34}$CO(CH$_2$)$_n$—;

each of R$^1$-R$^4$ and R$^{65}$-R$^{69}$ is independently a hydrogen, —OCF$_3$, C$_1$-C$_{20}$ alkyl, C$_3$-C$_{20}$ cycloalkyl, C$_5$-C$_{30}$ aryl, C$_5$-C$_{30}$ heteroaryl, C$_1$-C$_{20}$ acyl, C$_2$-C$_{20}$ alkenyl, C$_3$-C$_{20}$ cycloalkenyl, C$_2$-C$_{20}$ alkynyl, C$_5$-C$_{20}$ alkylaryl, C$_1$-C$_6$ alkoxycarbonyl, halo, halomethyl, dihalomethyl, trihalomethyl, —CO$_2$R$^{40}$, —SOR$^{41}$, —OSR$^{42}$, —SO$_2$OR$^{43}$, —CH$_2$(CH$_2$OCH$_2$)$_r$CH$_2$OH, —PO$_3$R$^{44}$R$^{45}$, —OR$^{46}$, —SR$^{47}$, —NR$^{48}$R$^{49}$, —NR$^{50}$COR$^{51}$, —CN, —CONR$^{52}$R$^{53}$, —COR$^{54}$, —NO$_2$, —SO$_2$R$^{55}$, —PO$_3$R$^{56}$R$^{57}$, —SO$_2$NR$^{58}$R$^{59}$, —CH$_2$(CHOH)$_r$R$^{60}$, or —(CH$_2$CH$_2$O)$_s$R$^{61}$;

Ar is a group corresponding to benzene, phenyl benzene, pyridine, pyrimidine, pyrazine, pyridazine, pyrrole, pyrazole, imidazole, oxazole, thiophene, thiazole, triazine, indole, triazole, furan, or thiadiazole;

each of r and s is independently an integer selected from the range of 1 to 100;

each of n, m and q is independently an integer selected from the range of 0 to 10;

each of a, b and d is independently 0 or 1; and each of R$^{13}$-R$^{34}$ is independently hydrogen, C$_1$-C$_{20}$ alkyl, C$_1$-C$_{20}$ cycloalkyl, C$_5$-C$_{20}$ aryl, C$_5$-C$_{20}$ heteroaryl, or C$_1$-C$_{20}$ acyl; and each of R$^{40}$-R$^{61}$ is independently hydrogen or C$_1$-C$_{10}$ alkyl. In an embodiment, a tissue sealant or closure device of the invention has an optical dye being of formula (FX5), wherein each of R$^1$-R$^3$ and R$^{65}$-R$^{69}$ is independently hydrogen, C$_1$-C$_{10}$ alkyl or C$_3$-C$_{10}$ cycloalkyl, optionally hydrogen or C$_1$-C$_5$ alkyl, and optionally hydrogen, in an embodiment, a tissue sealant or closure device of the invention has an optical dye being of formula (FX5), wherein each of a, b, and d is equal to 0 (i.e., L$^1$, L$^2$ and L$^4$ is not present), and optionally at least one of, and optionally all of, W$^1$, W$^2$ and W$^4$ is a single bond.

In an embodiment, a tissue sealant or closure device of the present invention comprises a thiazole-containing optical dye. In an embodiment, for example, the invention provides a tissue sealant or closure device wherein the optical dye has the formula:

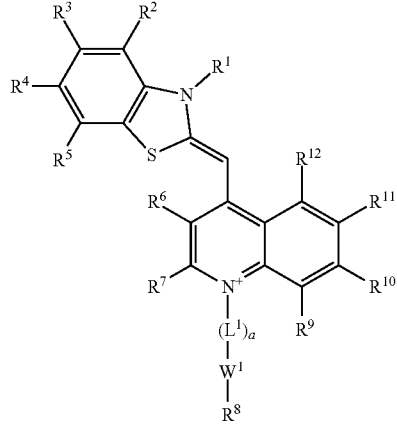

(FX6)

wherein L$^1$, if present, is independently C$_1$-C$_{20}$ alkylene, C$_3$-C$_{20}$ cycloalkylene, C$_2$-C$_{20}$ alkenylene, C$_3$-C$_{20}$ cycloalkenylene, C$_2$-C$_{20}$ alkynylene, ethenylene, ethynylene, or phenylene;

W$^1$ is a single bond, —(CH$_2$)$_n$—, —(HCCH)$_n$—, —(CH$_2$CH$_2$O)$_r$—, —(CHOH)$_s$—, —O—, —S—, —SO—, —SO$_2$—, —OSO$_2$—, —NR$^{13}$—, —CO—, —COO—, —OCO—, —OCOO—, —CONR$^{14}$—, —NR$^{15}$CO—, —OCONR$^{16}$—, —NR$^{17}$COO—, —NR$^{18}$CONR$^{19}$—, —NR$^{20}$CSNR$^{21}$—, —(CH$_2$)$_m$O(CH$_2$)$_n$—, —(CH$_2$)$_m$S (CH$_2$)$_n$—, —(CH$_2$)$_m$SO(CH$_2$)$_n$—, —(CH$_2$)$_m$SO$_2$(C$_{Hhd\,2}$)$_n$—, —(CH$_2$)$_m$SO$_3$(CH$_2$)$_n$—, —(CH$_2$)$_m$OSO$_2$(CH$_2$)$_n$—, —(CH$_2$)$_m$NR$^{22}$(CH$_2$)$_n$—, —(CH$_2$)$_m$CO(CH$_2$)$_n$—, —(CH$_2$)$_m$COO(CF$_{12}$)$_n$—, —(CH$_2$)$_m$OCO(CH$_2$)$_n$—, —(CH$_2$)$_m$OCOO(CH$_2$)$_n$—, —(CH$_2$)$_m$CONR$^{23}$(CH$_2$)$_n$—, —(CH$_2$)$_m$NR$^{24}$CO(CH$_2$)$_n$—, —(CH$_2$)$_m$OCONR$^{25}$(CH$_2$)$_n$—, —(CH$_2$)$_m$NR$^{26}$COO(CH$_2$)$_n$—, —(CH$_2$)$_m$NR$^{27}$CONR$^{28}$(CH$_2$)$_n$—, —(CH$_2$)$_m$NR$^{29}$CSNR$^{30}$(CH$_2$)$_n$—, —(CH$_2$)$_m$O(CH$_2$)$_n$NR$^{31}$CO(CH$_2$)$_n$—, —(CH$_2$)$_m$CO(CH$_2$)$_n$(CH$_2$OCH$_2$)$_q$(CH$_2$)$_n$NR$^{32}$(CH$_2$)$_n$NR$^{33}$CO(CH$_2$)$_n$—, or —(CH$_2$)$_m$CO(CH$_2$)$_n$NR$^{34}$CO(CH$_2$)$_n$—;

each of R$^1$-R$^{12}$ is independently a hydrogen, —OCF$_3$, C$_1$-C$_{20}$ alkyl, C$_3$-C$_{20}$ cycloalkyl, C$_5$-C$_{30}$ aryl, C$_5$-C$_{30}$ heteroaryl, C$_1$-C$_{20}$ acyl, C$_2$-C$_{20}$ alkenyl, C$_3$-C$_{20}$ cycloalkenyl, C$_2$-C$_{20}$ alkynyl, C$_5$-C$_{20}$ alkylaryl, C$_1$-C$_6$ alkoxycarbonyl, halo, halomethyl, dihalomethyl, trihalomethyl, —CO$_2$R$^{40}$, —SOR$^{41}$, —OSR$^{42}$, —SO$_2$OR$^{43}$, —CH$_2$(CH$_2$OCH$_2$)$_r$CH$_2$OH, —PO$_3$R$^{44}$R$^{45}$, —OR$^{46}$, —SR$^{47}$, —NR$^{48}$R$^{49}$, —NR$^{50}$COR$^{51}$, —CN, —CONR$^{52}$R$^{53}$, —COR$^{54}$, —NO$_2$, —SO$_2$R$^{55}$, —PO$_3$R$^{56}$R$^{57}$, —SO$_2$NR$^{55}$R$^{59}$, —CH$_2$(CHOH)$_r$R$^{60}$, or —(CH$_2$CH$_2$O)$_s$R$^{61}$;

each of r and s is independently an integer selected from the range of 1 to 100;

each of n, m and q is independently an integer selected from the range of 0 to 10;

a is 0 or 1;

each of R$^{13}$-R$^{34}$ is independently hydrogen, C$_1$-C$_{20}$ alkyl, C$_1$-C$_{20}$ cycloalkyl, C$_5$-C$_{20}$ aryl, C$_5$-C$_{20}$ heteroaryl, or C$_1$-C$_{20}$ acyl;

each of R$^{40}$-R$^{61}$ is independently hydrogen or C$_1$-C$_{10}$ alkyl. In an embodiment, a tissue sealant or closure device of the invention has an optical dye being of formula (FX6), wherein each of R$^1$-R$^{12}$ is independently hydrogen, C$_1$-C$_{10}$ alkyl or C$_3$-C$_{10}$ cycloalkyl, optionally wherein each of R$^1$-R$^{12}$ is independently hydrogen or C$_1$-C$_5$ alkyl, and optionally wherein each of R$^1$-R$^{12}$ is hydrogen. In an embodiment, a tissue sealant or closure device of the invention has an optical dye being of formula (FX6), wherein a is equal to 0 (i.e., L$^1$ is not present), and optionally W$^1$ is a single bond.

In an embodiment, the invention provides a tissue sealant or closure device wherein the optical dye is a thiazole-containing optical dye having the formula:

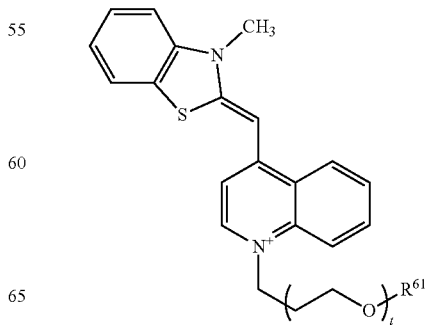

(FX7)

or

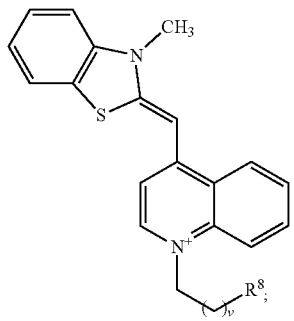

(FX8)

wherein each of t and v is independently selected from the range of 1 to 20, wherein $R^{61}$ and $R^8$ are as provided in the description of formula (FX6). In an embodiment, a sealant or closure device of the invention has an optical dye having formula (FX7) or (FX8) wherein each of t and v is independently selected from the range of 1 to 10, optionally 1 to 5.

The present invention includes tissue sealants and closure devices wherein the optical dye is covalently linked to an adhesive material component or plug component via a connecting group. In an embodiment, for example, a tissue sealant or closure device of the invention has the formula:

DYE—Z—T     (FX9);

wherein DYE is the optical dye, T is the adhesive material or the plug, and Z is a connecting group covalently linking the optical dye and the adhesive material or covalently linking the optical dye and the plug. In an embodiment, a plurality of optical dyes are covalently linked to the adhesive material or plug via a plurality of connecting groups. For example the present invention includes tissue sealants and closure devices having the formula

[DYE—Z—]$_u$---T;     (FX10)

wherein each DYE is independently an optical dye, T is the adhesive material or the plug, and each Z is independently a connecting group covalently linking the optical dye and the adhesive material or covalently linking the optical dye and the plug; and u is an integer selected over the range of 1 to 1,000,000, optionally the range of 1 to 100,000, optionally the range of 1 to 10,000, optionally the range of 1 to 1,000, optionally the range of 1 to 100. In Formula (FX10), u represents the number of Z-DYE components (shown in brackets) independently linked to the adhesive material or plug. The dashed line in formula (FX10) represents independent bonds linking T to Z-DYE components. Formula (FX10) is further clarified by reference to FIG. 4 which shows an example of a tissue sealant or closure device configuration wherein a plurality of optical dyes (DYE$^1$, DYE$^2$, DYE$^3$ . . . DYE$^u$) are independently linked to the adhesive material or plug (T) component via a plurality of connecting groups ($Z^1$, $Z^2$, $Z^3$, . . . $Z^u$). The number of independent DYE-Z groups coupled to T in tissue sealants and closure devices having formula (FX10) is selected on the basis of the desire therapeutic outcome, specific clinical application, and therapeutic objectives, the composition of the DYE, adhesive material and/or plug components and the synthetic approach for linking DYE, Z, and T components.

In an embodiment, the tissue sealant or closure device has the formula (FX9) or (FX10), and the optical dye (i.e., DYE) comprises a group corresponding to pyrazine, a thiazole, a phenylxanthene, a phenothiazine, a phenoselenazine, a cyanine, an indocyanine, a squaraine, a dipyrrolo pyrimidone, an anthraquinone, a tetracene, a quinoline, an acridine, an acridone, a phenanthridine, an azo dye, a rhodamine, a phenoxazine, an azulene, an azaazulene, a triphenyl methane dye, an indole, a benzoindole, an indocarbocyanine, a Nile Red dye, a thionin dye, an isosulfan blue dye or a benzo-indocarbocyanine. In an embodiment, the tissue sealant or closure device has the formula (FX9) or (FX10), and the optical dye is a pyrazine-containing dye or thiazole-containing dye.

In an embodiment, the invention provides a tissue sealant or closure device comprising a pyrazine-containing optical dye covalently bound to an adhesive material or plug. In an embodiment, for example, the optical dye and adhesive material or plug are covalently linked and have the formula:

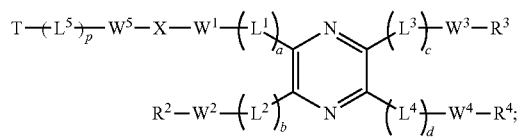

(FX11)

wherein T is the adhesive material or the plug;
X is a synthetic polymer, biopolymer, or —(CH$_2$)$_z$—, wherein one or more CH$_2$ groups of X may be replaced by NH, O, S, a carbonyl (C═O), or a sulfonyl (S═O or O═S═O); two adjacent CH$_2$ groups may be replaced by —CH═CH— or —C≡C—, wherein z is independently an integer selected from the range of 1 to 100;
each of L$^1$, L$^2$, L$^3$, L$^4$ and L$^5$, if present, is independently C$_1$-C$_{10}$ alkylene, C$_3$-C$_{10}$ cycloalkylene, C$_2$-C$_{10}$ alkenylene, C$_3$-C$_{10}$ cycloalkenylene, C$_2$-C$_{10}$ alkynylene, ethenylene, ethynylene, or phenylene;
each of W$^1$, W$^2$, W$^3$, W$^4$ and W$^5$ is independently a single bond, —(CH$_2$)$_n$—, —(HCCH)$_n$—, —(CH$_2$CH$_2$O)$_r$—, —(CHOH)$_s$—, —O—, —S—, —SO—, —SO$_2$—, —SO$_3$—, —OSO$_2$—, —NR$^{13}$—, —CO—, —COO—, —OCO—, —OCOO—, —CONR$^{14}$—, —NR$^{15}$CO—, —OCONR$^{16}$—, —NR$^{17}$COO—, —NR$^{18}$CONR$^{19}$—, —NR$^{20}$CSNR$^{21}$—, —(CH$_2$)$_m$O(CH$_2$)$_n$—, —(CH$_2$)$_m$S (CH$_2$)$_n$—, —(CH$_2$)$_m$SO(CH$_2$)$_n$—, —(CH$_2$)$_m$ SO$_2$(CH$_2$)$_n$—, -(CH$_2$)SO$_3$(CH$_2$)$_n$—, —(CH$_2$)$_m$OSO$_2$(CH$_2$)$_n$—, —(CH$_2$)$_m$NR$^{22}$(CH$_2$)$_n$—, —(CH$_2$)$_m$CO(CH$_2$)$_n$—, —(CH$_2$)$_m$COO(CH$_2$)$_n$—, —(CH$_2$)$_m$OCO(CH$_2$)$_n$—, —(CH$_2$)$_m$OCOO(C$_1$-12)$_n$—, —(CH$_2$)$_m$CONR$^{23}$(CH$_2$)$_n$—, —(CH$_2$)$_m$NR$^{24}$CO(CH$_2$)$_n$—, —(CH$_2$)$_m$OCONR$^{25}$ (CH$_2$)$_n$—, —(CH$_2$)$_m$NR$^{26}$COO(CH$_2$)$_n$—, —(CH$_2$)$_m$ NR$^{27}$CONR$^{28}$(CH$_2$)$_n$—, —(CH$_2$)$_m$NR$^{29}$CSNR$^{30}$(CH$_2$)$_n$—, —(CH$_2$)$_m$O(CH$_2$)$_n$NR$^{31}$CO(CH$_2$)$_n$—, —(CH$_2$)$_m$CO(CH$_2$)$_n$ (CH$_2$OCH$_2$)$_q$(CH$_2$)$_n$NR$^{32}$(CH$_2$)$_n$NR$^{33}$CO(CH$_2$)$_n$—, or —(CH$_2$)$_m$CO(CH$_2$)$_n$NR$^{34}$CO(CH$_2$)$_n$—
each of R$^2$, R$^3$, and R$^4$ is independently a hydrogen, —OCF$_3$, C$_1$-C$_{20}$ alkyl, C$_3$-C$_{20}$ cycloalkyl, C$_5$-C$_{30}$ aryl, C$_5$-C$_{30}$ heteroaryl, C$_1$-C$_{20}$ acyl, C$_2$-C$_{20}$ alkenyl, C$_3$-C$_{20}$ cycloalkenyl, C$_2$-C$_{20}$ alkynyl, C$_5$-C$_{20}$ alkylaryl, C$_1$-C$_6$ alkoxycarbonyl, halo, halomethyl, dihalomethyl, trihalomethyl, —CO$_2$R$^{40}$, —SOR$^{41}$, —OSR$^{42}$, —SO$_2$OR$^{43}$, —CH$_2$ (CH$_2$OCH$_2$)$_b$CH$_2$OH, —PO$_3$R$^{44}$R$^{45}$, —OR$^{46}$, —SR$^{47}$, —NR$_{48}$R$^{49}$, —NR$^{50}$COR$^{51}$, —CN, —CONR$^{52}$R$^{53}$, —COR$^{54}$, —NO$_2$, —SO$_2$R$^{55}$, —PO$_3$R$^{55}$R$^{57}$, —SO$_2$NR$^{58}$R$^{59}$, —CH$_2$(CHOH)$_r$R$^{60}$, or —CH$_2$CH$_2$O)$_s$R$^{61}$;

each of r and s is independently an integer selected from the range of 1 to 100;

each of n, m and q is independently an integer selected from the range of 0 to 10;

each of a, b, c, d and p is independently 0 or 1; and each of R$^{13}$-R$^{34}$ is independently hydrogen, C$_1$-C$_{20}$ alkyl, C$_1$-C$_{20}$ cycloalkyl, C$_5$-C$_{20}$ aryl, C$_5$-C$_{20}$ heteroaryl, or C$_1$-C$_{20}$ acyl;

each of R$^{40}$-R$^{61}$ is independently hydrogen or C$_1$-C$_{10}$ alkyl. The adhesive material or plug (as represented by T) shown in formula (FX11) may be linked to a plurality of optical dye components via the linking configuration shown in formula (FX11). In an embodiment, for example, the tissue sealant or closure device has formula (FX11) wherein the adhesive material or plug is independently linked to 1 to 100,000 optical dye components via independent connecting groups. In an embodiment, a tissue sealant or closure device of the invention has an optical dye being of formula (FX11), wherein each of R$^2$-R$^4$ is independently hydrogen, C$_1$-C$_{10}$ alkyl or C$_3$-C$_{10}$ cycloalkyl, optionally wherein each of R$^2$-R$^4$ is independently hydrogen or C$_1$-C$_5$ alkyl, and optionally wherein each of R$^2$-R$^4$ is hydrogen. In an embodiment, a tissue sealant or closure device of the invention has an optical dye being of formula (FX11), wherein each of a, b, c, p and d is equal to 0 (i.e., L$^1$-L$^5$ is not present), and optionally at least one of, and optionally all of, W$^1$-W$^5$ is a single bond.

In an embodiment, for example, the optical dye and adhesive material or plug are covalently linked and have the formula:

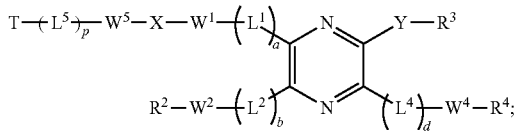

(FX12)

wherein T is the adhesive material or the plug;

X is a synthetic polymer, biopolymer, or —(CH$_2$)$_z$—, wherein one or more CH$_2$ groups of X may be replaced by NH, O, S, a carbonyl (C=O), or a sulfonyl (S=O or O=S=O); two adjacent CH$_2$ groups may be replaced by —CH=CH— or —C≡C—, wherein z is independently an integer selected from the range of 1 to 100;

each of L$^1$, L$^2$, L$^4$, and L$^5$, if present, is independently C$_1$-C$_{10}$ alkylene, C$_3$-C$_{10}$ cycloalkylene, C$_2$-C$_{10}$ alkenylene, C$_3$-C$_{10}$ cycloalkenylene, C$_2$-C$_{10}$ alkynylene, ethenylene, ethynylene, or phenylene;

each of W$^1$, W$^2$, W$^4$, and W$^5$ is independently a single bond, —(CH$_2$)$_n$—, —(HCCH)$_n$—, —(CH$_2$CH$_2$O)$_r$—, —(CHOH)$_s$—, —O—, —S—, —SO—, —SO$_2$—, —SO$_3$—, —OSO$_2$—, —NR$^{13}$—, —CO—, —COO—, —OCO—, —OCOO—, —CONR$^{14}$—, —NR$^{15}$CO—, —OCONR$^{16}$—, —NR$^{17}$COO—, —NR$^{18}$CONR$^{19}$—, —NR$^{20}$CSNR$^{21}$—, —(CH$_2$)$_m$O(CH$_2$)$_n$—, —(CH$_2$)$_m$S(CH$_2$)$_n$—, —(CH$_2$)$_m$SO(CH$_2$)$_m$—, —(CH$_2$)$_m$SO$_2$(CH$_2$)$_n$—, —(CH$_2$)$_m$SO$_3$(CH$_2$)$_n$—, —(CH$_2$)$_m$OSO$_2$(CH$_2$)$_n$—, —(CH$_2$)$_m$NR$^{22}$(CH$_2$)$_n$—, —(CH$_2$)$_m$CO(CH$_2$)$_n$—, —(CH$_2$)$_m$COO(CH$_2$)$_n$—, —(CH$_2$)$_m$OCO(CH$_2$)$_n$—, —(CH$_2$)$_m$OCOO(CH$_2$)$_n$—, —(CH$_2$)$_m$CONR$^{23}$(CH$_2$)$_n$—, —(CH$_2$)$_m$NR$^{24}$CO(CH$_2$)$_n$—, —(CH$_2$)$_m$OCONR$^{25}$(CH$_2$)$_n$—, —(CH$_2$)$_m$NR$^{26}$COO(CH$_2$)$_n$—, —(CH$_2$)$_m$NR$^{27}$CONR$^{28}$(CH$_2$)$_n$—, —(CH$_2$)$_m$NR$^{29}$CSNR$^{30}$(CH$_2$)$_n$—, —(CH$_2$)$_m$O(CH$_2$)$_n$NR$^{31}$CO(CH$_2$)$_n$—, —(CH$_2$)$_m$CO(CH$_2$)$_n$(CH$_2$OCH$_2$)$_q$(CH$_2$)$_n$NR$^{33}$CO(CH$_2$)$_n$—, or —(CH$_2$)$_m$CO(CH$_2$)$_n$NR$^{34}$CO(CH$_2$)$_n$—;

each of R$^2$-R$^4$ and R$^{65}$ R$^{69}$ is independently a hydrogen, —OCF$_3$, C$_1$-C$_{20}$ alkyl, C$_3$-C$_{20}$ cycloalkyl, C$_5$-C$_{30}$ aryl, C$_5$-C$_{30}$ heteroaryl, C$_1$-C$_{20}$ acyl, C$_2$-C$_{20}$ alkenyl, C$_3$-C$_{20}$ cycloalkenyl, C$_2$-C$_{20}$ alkynyl, C$_5$-C$_{20}$ alkylaryl, C$_1$-C$_6$ alkoxycarbonyl, halo, halomethyl, dihalomethyl, trihalomethyl, —CO$_2$R$^{40}$—SOR$^{41}$, —OSR$^{42}$, —SO$_2$OR$^{43}$, —CH$_2$(CH$_2$OCH$_2$)$_b$CH$_2$OH, —PO$_3$R$^{44}$R$^{45}$, —SR$^{47}$, —NR$^{48}$R$^{49}$, —NR$^{50}$COR$^{51}$, —CN, —CONR$^{52}$R$^{53}$, —COR$^{54}$, —NO$_2$, —SO$_2$R$^{55}$, —PO$_3$R$^{56}$R$^{57}$, —SO$_2$NR$^{58}$R$^{59}$, —CH$_2$(CHOH)$_r$R$^{60}$, or —(CH$_2$CH$_2$O)$_s$R$^{61}$;

each of r and s is independently an integer selected from the range of 1 to 100;

each of n, m and q is independently an integer selected from the range of 0 to 10;

each of a, b, d and p is independently 0 or 1; and each of R$^{13}$-R$^{34}$ is independently hydrogen, C$_1$-C$_{20}$ alkyl, C$_1$-C$_{20}$ cycloalkyl, C$_5$-C$_{20}$ aryl, C$_5$-C$_{20}$ heteroaryl, or C$_1$-C$_{20}$ acyl;

each of R$^{40}$-R$^{61}$ is independently hydrogen or C$_1$-C$_{10}$ alkyl.

Y is —Ar—, —C(R$^{66}$)=C(R$^{66}$)—Ar—, —C≡C—Ar—, —N=N—Ar—, —CO—Ar—, —N(R$^{67}$)—Ar—, —O—Ar—, —S—Ar—, —SO—Ar—, —SO$_2$—Ar—, —C(R$^{68}$)=C(R$^{69}$)—, or —C≡C—; and Ar is a group corresponding to benzene, phenyl benzene, pyridine, pyrimidine, pyrazine, pyridazine, pyrrole, pyrazole, imidazole, oxazole, thiophene, thiazole, triazine, indole, triazole, furan, or thiadiazole. The adhesive material or plug (as represented by T) shown in formula (FX12) may be linked to a plurality of optical dye components via the linking configuration shown in formula (FX12). In an embodiment, for example, the tissue sealant or closure device has formula (FX12) wherein the adhesive material or plug (T) is independently linked to 1 to 100,000 optical dye components (DYE) via independent connecting groups.

In an embodiment, the invention provides a tissue sealant or closure device comprising a thiazole-containing optical dye covalently bound to an adhesive material or plug. In an embodiment, for example, the optical dye and adhesive material or plug are covalently linked and have the formula

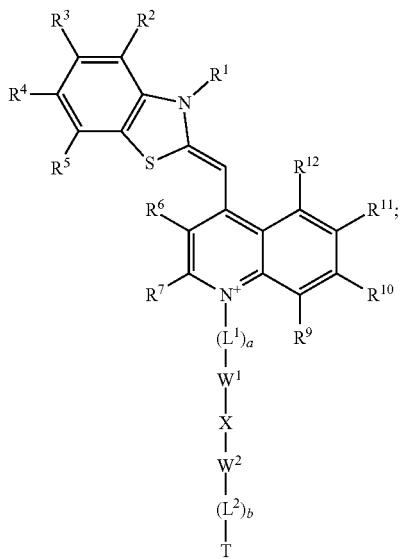

(FX13)

wherein T is the adhesive material or the plug;

X is a synthetic polymer, biopolymer, or —(CH$_2$)$_z$—, wherein one or more CH$_2$ groups of X may be replaced by NH, O, S, a carbonyl (C=O), or a sulfonyl (S=O or O=S=O); two adjacent CH$_2$ groups may be replaced by —CH=CH— or —C≡C—, wherein z is independently an integer selected from the range of 1 to 100;

wherein each of L$^1$ and L$^2$, if present, is independently C$_1$-C$_{20}$ alkylene, C$_3$-C$_{20}$ cycloalkylene, C$_2$-C$_{20}$ alkenylene, C$_3$-C$_{20}$ cycloalkenylene, C$_2$-C$_{20}$ alkynylene, ethenylene, ethynylene, or phenylene;

W$^1$ and W$^2$ are independently a single bond, —(CH$_2$)$_n$—, —(HCCH)$_n$—, —(CH$_2$CH$_2$O)$_r$—, —(CHOH)$_s$—, —O—, —S—, —SO—, —SO$_2$—, —SO$_3$—, —OSO$_2$—, —NR$^{13}$—, —CO—, —COO-, -000—, —OCOO—, —CONR$^{14}$—, —NR$^{15}$CO—, —OCONR$^{16}$—, —NR$^{17}$COO—, —NR$^{18}$CONR$^{19}$—, —NR$^{20}$CSNR$^{21}$—, —(CH$_2$)$_m$O(CH$_2$)$_n$—, —(CH$_2$)$_m$S(CH$_2$)$_n$—, —(CH$_2$)$_m$SO (CH$_2$)$_n$—, —(CH$_2$)$_m$ SO$_2$(CH$_2$)$_n$—, —(CH$_2$)$_m$SO$_3$(CH$_2$)$_n$—, —(CH$_2$)$_n$OSO$_2$(CH$_2$)$_n$—, —(CH$_2$)$_m$NR$^{22}$(CH$_2$)$_n$—, —(CH$_2$)$_m$CO(CH$_2$)$_n$—, —(CH$_2$)$_m$COO(CH$_2$)$_n$—, —(CH$_2$)$_m$OCO(CH$_2$)$_n$—, —(CH$_2$)$_m$OCOO(CH$_2$)$_n$—, —(CH$_2$)$_m$CONR$^{23}$(CH$_2$)$_n$—, —(CH$_2$)$_m$NR$^{24}$CO(CH$_2$)$_n$—, —(CH$_2$)$_m$OCONR$^{25}$(CH$_2$)$_n$—, —(CH$_2$)$_m$NR$^{26}$COO (CH$_2$)$_n$—, —(CH$_2$)$_m$NR$^{27}$CONR$^{28}$(CH$_2$)$_n$—, —(CH$_2$)$_m$ NR$^{29}$CSNR$^{30}$(CH$_2$)$_n$—, —(CH$_2$)$_m$O(CH$_2$)$_n$NR$^{31}$CO (CH$_2$)$_n$—, —(CH$_2$)$_m$CO(CH$_2$)$_q$(CH$_2$OCH$_2$)$_n$NR$^{32}$ (CH$_2$)$_n$NR$^{32}$(CH$_2$)$_n$NR$^{33}$CO(CH$_2$)$_n$—, or —(CH$_2$)$_m$CO (CH$_2$)$_n$NR$^{34}$CO(CH$_2$)$_n$—, each of R$^1$-R$^7$ and R$^9$-R$^{12}$ is independently a hydrogen, —OCF$_3$, C$_1$-C$_{20}$ alkyl, C$_3$-C$_{20}$ cycloalkyl, C$_5$-C$_{30}$ aryl, C$_5$-C$_{30}$ heteroaryl, C$_1$-C$_{20}$ acyl, C$_2$-C$_0$ alkenyl, C$_3$-C$_{20}$ cycloalkenyl, C$_2$-C$_{20}$ alkynyl, C$_5$-C$_{20}$ alkylaryl, C$_1$-C$_6$ alkoxycarbonyl, halo, halomethyl, dihalomethyl, trihalomethyl, —CO$_2$R$^{40}$, —SOR$^{41}$, —OSR$^{42}$, —SO$_2$OR$^{43}$, —CH$_2$ (CH$_2$OCH$_2$)$_b$CH$_2$OH, —PO$_3$R$^{44}$R$^{45}$, —OR$^{46}$, —SR$^{47}$, —NR$^{48}$R$^{49}$, —NR$^{50}$COR$^{51}$, —CN, —CONR$^{52}$R$^{53}$, —COR$^{54}$, —NO$_2$, —SO$_2$R$^{55}$, —PO$_3$R$^{56}$R$^{57}$, —SO$_2$NR$^{58}$R$^{59}$, —CH$_2$(CHOH)$_r$R$^{60}$, or —(CH$_2$ CH$_2$O)$_s$R$^{61}$;

each of r and s is independently an integer selected from the range of 1 to 100;

each of n, m and q is independently an integer selected from the range of 0 to 10;

each of a and b is independently 0 or 1;

each of R$^{13}$-R$^{34}$ is independently hydrogen, C$_1$-C$_{20}$ alkyl, C$_1$-C$_{20}$ cycloalkyl, C$_5$-C$_{20}$ aryl, C$_5$-C$_{20}$ heteroaryl, or C$_1$-C$_{20}$ acyl;

each of R$^{40}$-R$^{61}$ is independently hydrogen or C$_1$-C$_{10}$ alkyl. The adhesive material or plug (as represented by T) shown in formula (FX13) may be linked to a plurality of optical dye components via the linking configuration shown in formula (FX13). In an embodiment, for example, the tissue sealant or closure device has formula (FX13) wherein the adhesive material or plug (T) is independently linked to 1 to 100,000 optical dye components (DYE) via independent connecting groups.

In certain embodiments, selection of the composition of the connecting group linking the optical dye and adhesive material or plug is beneficial for establishing the optical, mechanical and/or chemical properties of the present tissue sealants and closure devices. Connecting groups of some embodiments, for example, are multifunctional, for example, providing a covalent linkage between the optical dye and adhesive material or plug components, and also providing targeting or molecular recognition functionality. In some embodiments for example, the connecting group has an affinity to fibrin, collagen and/or a synthetic polymer network. In some embodiments for example, the connecting group binds to fibrin, collagen and/or a synthetic polymer network. In some embodiments for example, the connecting group is a targeting moiety for directing the optical dye into a tissue seal, fibrin network, synthetic polymer network, vasculature closure or clot. In an embodiment, the tissue sealant or closure device has a formula of (FX9)-(FX13), and Z or X is a C$_1$-C$_{100}$ alkylene, a C$_3$-C$_{100}$ cycloalkylene C$_2$-C$_{100}$ alkenylene, C$_3$-C$_{100}$ cycloalkenylene, C$_2$-C$_{100}$ alkynylene or C$_5$-C$_{100}$ arylene. In an embodiment, the tissue sealant or closure device has a formula of (FX9)-(FX13), and Z or X is a polypeptide group, an oligonucleotide group, a polysaccharide group, or a peptidomimetic group. In an embodiment, the tissue sealant or closure device has a formula of (FX9)-(FX13), and Z or X is collagen group or a collagen mimetic polypeptide group. In an embodiment, the tissue sealant or closure device has a formula of ((FX9)-(FX13), and Z or X is a synthetic polymer group. In an embodiment, the tissue sealant or closure device has a formula of (FX9)-(FX13), and Z or X is a group corresponding to a polymer, such as a group corresponding to poly (ethylene glycol), a polyurethane, a polyamine, a succinimide-derivatized poly(ethylene glycol), a thiol-derivatized poly(ethylene glycol), a polyisocyanate, a polycyanoacrylate, a polyacrylate, a polyamine, a polyalkylene oxide, a polyglycerol, or a polyamide. In an embodiment, the tissue sealant or closure device has a formula of (FX9)-(FX13), and X or Z is —(CH$_2$CH$_2$O)$_m$—, wherein m is selected from the range of 1 to 100.

The present invention includes tissue sealants for biomedical applications, including procedures for treating a wound, vasculature access site, puncture or other opening in vascular tissue, comprising purified stereoisomers (e.g., enantiomers and diastereomers), salts (including quarternary salts), and/or ionic forms (e.g., protonated and deprotonated forms) of the compounds of any of formula (FX1)-(FX13), and mixtures thereof. As will be understood by those having general skill in the art, acidic functional groups and basic functional groups of the compounds of any of formula (FX1)-(FX13) may be in protonated or deprotonated states depending on the molecular environment (e.g., pH, ionic strength, composition, etc.), for example during synthesis, formulation and/or administration.

Reference to a, b, c, d, and/or p equal to 1 in the context of the compounds of formulas (FX1)-(FX13) refers to compounds of the invention wherein $L^1$, $L^2$, $L^3$, $L^4$, and/or $L^5$, independently and respectively, is present in the compound. Reference to a, b, c, d, and/or p equal to 0 in the context of formula (FX1)-(FX13) refers to embodiments wherein $L^1$, $L^2$, $L^3$, $L^4$, and/or $L^5$, independently and respectively, is not present in the compound. In an embodiment, a tissue sealant or closure device of the invention has an optical dye being of any of formula (FX1)-(FX13), wherein each of $R^{13}$-$R^{34}$ is independently hydrogen, $C_1$-$C_{10}$ alkyl or $C_3$-$C_{10}$ cycloalkyl, optionally wherein each of $R^{13}$-$R^{34}$ is independently hydrogen or $C_1$-$C_5$ alkyl, and optionally wherein each of $R^{13}$-$R^{34}$ is hydrogen. In an embodiment, a tissue sealant or closure device of the invention has an optical dye being of any of formula (FX1)-(FX13), wherein each of $R^{40}$-$R^{61}$ is independently hydrogen or $C_1$-$C_5$ alkyl, and optionally wherein each of $R^{40}$-$R^{61}$ is hydrogen. In an embodiment, a tissue sealant or closure device of the invention has an optical dye being of any of formula (FX1)-(FX13), wherein each of a, b, c, d, and p is 0, and optionally wherein each of $W^1$-$W^5$ is a single bond. In an embodiment, a tissue sealant or closure device of the invention has an optical dye being of any of formula (FX1)-(FX13), wherein each of $W^1$-$W^5$ is independently a single bond, —O—, —S—, —SO—, —$SO_2$—, —$SO_3$—, —$OSO_2$—, —$NR^{13}$—, —CO—, —COO—, —OCO—, —OCOO—, —$CONR^{14}$—, —$NR^{15}CO$—, —$OCONR^{16}$—, —$NR^{17}COO$—, —$NR^{16}CONR^{19}$—, or —$NR^{20}CSNR^{121}$—. In an embodiment, a tissue sealant or closure device of the invention has an optical dye being of any of formula (FX1)-(FX13), wherein at least one of $R^1$-$R^{12}$ is $C_1$-$C_5$ alkyl, —$OR^{46}$, —$SR^{47}$, —$NR^{48}R^{49}$, or —$NR^{50}COR^{51}$. In an embodiment, a tissue sealant or closure device of the invention has an optical dye being of any of formula (FX1)-(FX13), wherein at least one of $R^1$-$R^{12}$ is —CN, halo, —$CO_2R^{40}$, —$COR^{54}$, —$NO_2$, —$SO_2R^{55}$, or —$SO_2NR^{58}R^{59}$. In an embodiment, a tissue sealant or closure device of the invention has an optical dye being of any of formula (FX1)-(FX13), wherein at least one of $R^1$-$R^{12}$ is $C_1$-$C_6$ alkyl, —$OR^{46}$, —$SR^{47}$, —$NR^{48}R^{49}$, or —$NR^{50}COR^{51}$ and wherein at least one of $R^1$-$R^{12}$ is —CN, halo, —$CO_2R^{40}$, —$COR^{54}$, —$NO_2$, —$SO_2R^{55}$, or —$SO_2NR^{58}R^{59}$. In an embodiment, a tissue sealant or closure device of the invention has an optical dye being of any of formula (FX1)-(FX13), wherein each of $R^{65}$-$R^{69}$ is independently hydrogen, $C_1$-$C_{10}$ alkyl or $C_3$-$C_{10}$ cycloalkyl, optionally wherein each of $R^{65}$-$R^{69}$ is independently hydrogen or $C_1$-$C_5$ alkyl, and optionally wherein each of $R_{65}$-$R^{69}$ is hydrogen.

Tissue sealants and devices of the present invention may be used for a range of clinical applications, including surgical procedures, for in vivo administration and use of a tissue sealant or closure device, and/or for monitoring and visualization processes including tissue seal formation and closure of a vascular opening. The tissue sealants and devices of the present invention may be provided in various formulations and forms depending on the clinical application of interest, including administration of therapeutically effective dosage and/or form of the tissue sealant or closure device. The present invention provides methods of using tissue sealants and closure devices for treatment of a range of conditions and disorders, including the treatment and/or closure of a vasculature puncture, access site and/or wound.

In an embodiment, for example, the invention provides a tissue sealant for use in a medical procedure to form a seal in a biological tissue, wherein the procedure comprises: (i) administering to a subject a therapeutically effective amount of a tissue sealant of the present invention to the biological tissue; (ii) activating the adhesive material of the tissue sealant, thereby forming the seal in the biological tissue; and (iii) exposing the tissue sealant administered to the subject to electromagnetic radiation. In an embodiment, for example, the invention provides a closure device for use in a medical procedure to at least partially occlude an opening in a vasculature tissue, wherein the procedure comprises: (I) administering to a subject a closure device of the present invention to the opening in the vasculature tissue, thereby at least partially occluding the opening in the vasculature tissue; and (ii) exposing the closure device administered to the subject to electromagnetic radiation. In an embodiment, for example, the invention provides a tissue sealant for use in a procedure for the treatment of a vasculature puncture, wherein the procedure comprises: (i) administering to a subject a therapeutically effective amount of a tissue sealant of the present invention to the vasculature puncture; (ii) activating the adhesive material of the tissue sealant, thereby forming the seal at least partially covering the vasculature puncture; and (iii) exposing the tissue sealant administered to the subject to electromagnetic radiation. In an embodiment, for example, the invention provides a closure device for use in a procedure for the treatment of a vasculature puncture, wherein the procedure comprises: (i) administering to a subject a closure device of the present invention to the vasculature puncture, thereby at least partially occluding the opening in the vasculature; and (ii) exposing the closure device administered to the subject to electromagnetic radiation. In an embodiment, the tissue sealant or closure device is exposed to electromagnetic radiation having wavelengths selected over a range of 350 nanometers to 1300 nanometers, optionally wavelengths over the range of 400 nanometers to 900 nanometers. In an embodiment, the method further comprises detecting electromagnetic radiation from the tissue sealant or closure device, such as detecting fluorescence, scattered light or reflected tight from the tissue sealant or closure device. In an embodiment, the method further comprises optically filtering electromagnetic radiation from the tissue sealant or closure device, for example, in a manner preventing or minimizing detection of light having wavelengths corresponding to the electromagnetic radiation provided to the tissue sealant or closure device in the exposure step.

Methods of the present invention optionally include a number of additional steps. In an embodiment, for example, a method of the invention further comprises exciting emission from the tissue sealant or the closure device. In an embodiment, for example, a method of the invention further comprises detecting electromagnetic radiation reflected, scattered or emitted by the tissue sealant or the closure device, such as detecting fluorescence from the tissue sealant or the closure device. In an embodiment, for example, a method of the invention further comprises the step of detecting a change from the first optical condition of the optical dye to the second optical condition of the optical dye. In an embodiment, the a method of the invention further comprises detecting a change in an optical condition of the optical dye. In an embodiment, the a method of the invention further comprises: (i) observing a first optical condition, (ii) observing a second optical condition that is distinguishable from the first optical condition, thereby detecting a change in an optical condition of the optical dye. The invention includes methods wherein the change in optical condition is detected visually and methods wherein the change is optical condition is detected using an optical detector, such as an imaging system. In an embodiment, the a method of the invention further comprises evaluating a tissue seal or vasculature closure by assessing emission from the tissue sealant or closure device.

In an embodiment, for example, a method of the invention comprises activating the adhesive material or plug by physically contacting the biological tissue, for example, wherein activation involves chemical reactions of natural clotting agents and factors. In an embodiment, for example, a method of the invention comprises activating the adhesive material or plug by exposing the adhesive material or plug to electromagnetic radiation, for example to initiate polymerization and/or polymer cross linking reactions. In an embodiment, for example, a method of the invention comprises activating the adhesive material or plug by exposing the adhesive material or plug to heat, for example to initiate polymerization and/or polymer cross linking reactions. In an embodiment, for example, a method of the invention comprises activating the adhesive material or plug by exposing the adhesive material or plug to one or more chemical initiators, for example to initiate polymerization and/or polymer cross linking reactions. In an embodiment, a method of the invention further comprising initiating polymerization reactions involving the adhesive material or plug, for example so as to result in a polymer network. In an embodiment, the method further comprising initiating cross linking reactions involving the adhesive material or plug, for example so as to result in a polymer network.

In an embodiment, for example, a method of the invention further comprises detecting a change in the wavelength of emission or a distribution of wavelengths of the emission from the tissue sealant or the closure device after activation of the adhesive material or at least partial occlusion of the vasculature opening by the plug. In an embodiment, the detected change in a wavelength of the emission or distribution of wavelengths of the emission from the tissue sealant or the closure device is greater than or equal to 5 nanometers or optionally greater than or equal to 10 nanometers, or optionally greater than or equal to 20 nanometers. In an embodiment, the wavelength of the emission from the tissue sealant or the closure device increases after activation of the adhesive material or at least partial occlusion of the vasculature opening by the plug. In an embodiment, the wavelength of the emission from the tissue sealant or the closure device decreases after activation of the adhesive material or at least partial occlusion of the vasculature opening by the plug.

In an embodiment, for example, a method of the invention further comprises detecting a change in an absorption maximum in the visible or near infrared regions of the electromagnetic spectrum of the tissue sealant or the closure device after activation of the adhesive material or at least partial occlusion of the vasculature opening by the plug. In an embodiment, the detected change in the absorption maximum in the visible or near infrared regions of the electromagnetic spectrum of the tissue sealant or the closure device is greater than or equal to 5 nanometers, or optionally greater than or equal to 10 nanometers or optionally greater than or equal to 20 nanometers. In an embodiment, the absorption maximum of the tissue sealant or the closure device increases after activation of the adhesive material or at least partial occlusion of the vasculature opening by the plug. In an embodiment, the absorption maximum of the tissue sealant or the closure device decreases after activation of the adhesive material or at least partial occlusion of the vasculature opening by the plug. In an embodiment, a method of the invention further comprises detecting a change in the color of the tissue sealant or the closure device.

In an embodiment, the invention provides a method wherein activating the tissue sealant or at least partially occluding the opening forms a tissue seal, a fibrin network, synthetic polymer network or a clot, for example, at the site of an opening, puncture or wound in vascular tissue. In an embodiment, the invention provides a method wherein activating the tissue sealant or at least partially occluding the vasculature opening initiates a coagulation cascade, for example, at the site of an opening, puncture or wound in vascular tissue. In an embodiment, activating the tissue sealant or at least partially occluding the vasculature opening incorporates the optical dye in a tissue seal, fibrin network, synthetic polymer network or clot, for example, at the site of an opening, puncture or wound in vascular tissue. In an embodiment, the invention provides a method wherein the tissue sealant or at least partially occluding the vasculature opening immobilizes the optical dye in a tissue seal, fibrin network, synthetic polymer network or clot, for example, at the site of an opening, puncture or wound in vascular tissue. In an embodiment, the invention provides a method wherein activating the tissue sealant or at least partially occluding the vasculature opening rigidifies the optical dye, for example, at the site of an opening, puncture or wound in vascular tissue.

In an embodiment, the invention provides a pharmaceutical composition comprising a tissue sealant or closure device as described herein; and one or more pharmaceutically acceptable excipients. In an embodiment, the invention provides a pharmaceutical composition comprising the tissue sealant or closure device as described herein; and one or more additional therapeutic agents or diagnostic agents.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

Various features discussed below in relation to one or more of the exemplary embodiments may be incorporated into any of the above-described aspects of the present invention alone or in any combination. Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

BRIEF DESCRIPTION OF THE FIGURES

FIG. 3A shows the vasculature closure device prior to administration to a vasculature opening and FIG. 3B shows the vasculature closure device upon administration to a vasculature opening.

STATEMENTS REGARDING CHEMICAL COMPOUNDS AND NOMENCLATURE

Figure 1:
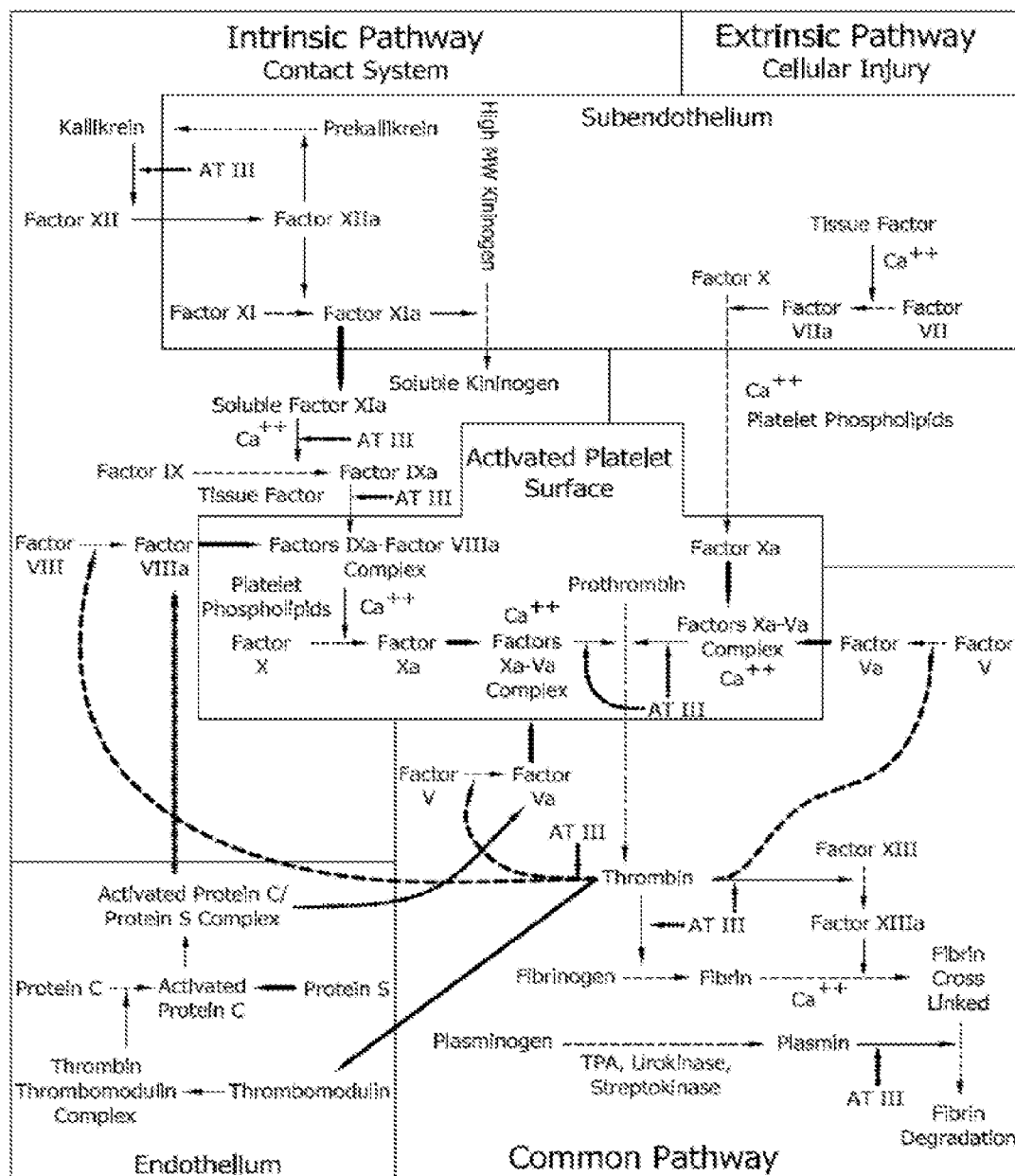
FIG. 1 is a flow chart showing the coagulation cascade and the various components and factors involved therewith. In the flow chart, AT III is antithrombin III, $Ca^{++}$ is calcium ions, and TPA is tissue plasminogen activator.

In an embodiment, a composition or compound of the invention is isolated or purified. In an embodiment, an isolated or purified compound is at least partially isolated or purified as would be understood in the art. In an embodiment, the composition or compound of the invention has a chemical purity of 95%, optionally for some applications 99%, optionally for some applications 99.9%, optionally for some applications 99.99%, and optionally for some applications 99.999%.

Many of the molecules disclosed herein contain one or more ionizable groups. Ionizable groups include groups from which a proton can be removed (e.g., —COOH) or added (e.g., amines) and groups which can be quaternized (e.g., amines). All possible ionic forms of such molecules, and salts thereof, are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As is customary and well known in the art, hydrogen atoms in formulas (FX1)-FX21) are not always explicitly shown, for example, hydrogen atoms bonded to the carbon atoms of aromatic, heteroaromatic, and alicyclic rings are not always explicitly shown in formulas (FX1)-(FX21). The structures provided herein, for example in the context of the description of formulas (FX1)-(FX21), are intended to convey to one of reasonable skill in the art the chemical composition of compounds of the methods and compositions of the invention, and as will be understood by one of skill in the art, the structures provided do not indicate the specific positions of atoms and bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. Compounds of the invention may have substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as attaching and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorphore, aromatic antenna, dye and/or imaging groups. Compounds of the invention include substituted and/or unsubstituted $C_3$-$C_{30}$ arylene, $C_3$-$C_{20}$ arylene, $C_3$-$C_{70}$ arylene and $C_1$-$C_5$ arylene groups.

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorphore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the invention include substituted and/or unsubstituted $C_2$-$C_{20}$ alkenylene, $C_2$-$C_{10}$ alkenylene and $C_2$-$C_5$ alkenylene groups.

As used herein, the terms "cylcoalkenylene" and "cylcoalkenylene group" are used synonymously and refer to a divalent group derived from a cylcoalkenyl group as defined herein. The invention includes compounds having one or more cylcoalkenylene groups. Cycloalkenylene groups in some compounds function as attaching and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups.

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as attaching and/or spacer groups. Compounds of the invention include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br), iodo (—I) or astato (—At) groups.

The term "heterocyclic" refers to ring structures containing at least one other kind of atom, in addition to carbon, in the ring. Examples of such atoms include nitrogen, oxygen and sulfur. Examples of heterocyclic rings include, but are not limited to, pyrrolidinyl, piperidyl, imidazolidinyl, tetrahydrofuryl, tetrahydrothienyi, fury!, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic" refers to a ring that is not an aromatic ring. Alicyclic rings include both carbocyclic and heterocyclic rings.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspatlic acid and glutamic acid. As used herein, reference to "a side chain residue of a natural Ⅱ-amino acid" specifically includes the side chains of the above-referenced amino acids.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O—$.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenylgroups can also carry alkyl groups. Cycloalkenylgroups can include bicyclic and tricyclic alkenyl groups. Alkenyl groups are optionally substituted. Substituted alkenyl groups include among others those which are substituted with alkyl or aryl groups, which groups in turn can be optionally substituted, Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6- or 7-member aromatic and/or heterocyclic aromatic rings. The term heteroalyl specifically refers to aryl groups having at least one 5-, 6- or 7-member heterocyclic aromatic rings. Aryl groups can contain one or more fused aromatic and heteroaromatic rings or a combination of one or more aromatic or heteroaromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups and/or electron withdrawing groups provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As to any of the groups described herein which contain one or more substituents, it is understood that such groups do not contain any substitution or substitution patterns which are sterically impractical and/or synthetically nonfeasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

DETAILED DESCRIPTION

The following definitions and methods are provided to better define the invention and to guide those of ordinary skill in the art in the practice of the invention.

Referring to the drawings, like numerals indicate like elements and the same number appearing in more than one drawing refers to the same element. Unless otherwise noted, the terms and phrases used herein have their art-recognized meaning, which can be found by reference to standard texts, journal references and contexts known to those skilled in the relevant art.

The term "amino acid" comprises naturally occurring amino acids as well as non-naturally occurring amino acids, including amino acid analogs and derivatives. One skilled in the art will recognize that reference herein to an amino acid includes, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids.

As used herein, the term "polymer" refers to a molecule comprising a plurality of repeating chemical groups, typically referred to as monomers. For some embodiments, polymers are characterized by high molecular masses and high average molecular masses, such as a molecular mass or average molecular mass selected over the range of 200 Daltons to 50000 Daltons, or for some applications 500 Daltons to 10000 Daltons, or for some applications 500 Daltons to 5000 Daltons. Useful polymers include organic polymers, biopolymers and synthetic polymers. Polymers may comprise monomers having the same chemical composition or may comprise a plurality of monomers having different chemical compositions, such as a copolymer including a block copolymer. For some embodiments, the term "biopolymer" refers to biologically active, biologically synthesized and/or naturally occurring polymers. Examples of biopolymers include proteins, peptides, glycopeptides, glycoproteins, polynucleotides, DNA, RNA, carbohydrates, and polysaccharides. For some embodiments, the term "synthetic polymer" refers to polymers which are not naturally occurring and/or are generated by chemical synthesis. For some embodiments, the term "crosslinked polymer" refers to polymer molecules having portions covalently bonded to other portions of the same or neighboring polymer molecules; in some embodiments, a partially crosslinked polymer refers to a polymer in which further covalent bonds can be formed between portions of polymer molecules.

The term "polymer network" refers to a plurality of polymer molecules covalently linked to and/or non-covalently associated with one another to form a collection of polymer molecules. In some embodiments, polymer networks incorporate and/or immobilize other materials, for example cells or dye molecules. In some embodiments, a clot, fibrin network or tissue seal comprises a polymer network.

The term "nucleic acid" as used herein generally refers to a molecule or strand of DNA, RNA, or derivatives or analogs thereof including one or more nucieobases. Nucleobases comprise purine or pyrimidine bases typically found in DNA or RNA (e.g., adenine, guanine, thymine, cytosine, and/or uracil). The term "nucleic acid" also comprises oligonucleotides and polynucleotides. Nucleic acids may be single-stranded molecules, or they may be double-, triple- or quadruple-stranded molecules that may comprise one or more complementary strands of a particular molecule. "Nucleic acid" includes artificial nucleic acids including peptide nucleic acids, morpholino nucleic acids, glycol nucleic acids and threose nucleic acids. Artificial nucleic acids may be capable of nucleic acid hybridization.

As used herein, "sequence" means the linear order in which monomers occur in a polymer, the order of amino acids in a polypeptide or the order of nucleotides in a polynucleotide, for example.

The terms "peptide" and "polypeptide" are used synonymously in the present description, and refer to a class of compounds comprising of amino acid residues chemically bonded together by amide bonds (or peptide bonds), regardless of length, functionality, environment, or associated molecule(s). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides comprising 2 to 100 amino acid units, optionally for some embodiments 2 to 50 amino acid units and, optionally for some embodiments 2 to 20 amino acid units can be used as a connecting group in the invention, for example, where the polypepetide preferentially binds to proteins, peptides or other biomolecules expressed, or otherwise generated by, a target tissue, such as a tumor, precancerous tissue, site of inflammation or other lesion. Typically, the polypeptide is at least four amino acid residues in length and can range up to a full-length protein.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

As used herein, "polynucleotide" and "oligonucleotide" are used interchangeably and refer to a class of compounds composed of nucleic acid residues chemically bonded together. The invention provides optical agents having an oligonucleotide or polynucleotide connecting group which comprises a plurality of nucleic acid residues, such as DNA or RNA residues, and/or modified nucleic acid residues that preferentially binds to proteins, peptides or other biomolecules expressed, or otherwise generated by, a target tissue, such as a tumor, precancerous tissue, site of inflammation or other lesion. Modifications to nucleic acid residues can be naturally occurring or non-naturally occurring, such as modifications generated by chemical synthesis. Oligo- or poly-nucleotide connecting groups include, for example, oligo- or poly-nucleotides comprising 2 to 100 nucleic acid units, optionally for some embodiments 2 to 50 nucleic acid units and, optionally for some embodiments 2 to 20 nucleic acid units, and optionally for some embodiments 2 to 10 nucleic acid units. Polypeptide and oligonucleotide include a polymer of at least two nucleotides joined together by phosphodiester bonds and may consist of either ribonucleotides or deoxyribonucleotides.

The term "aptamer" refers to an oligo- or poly-nucleotide or polypeptide that binds to, or otherwise selectively or preferentially associates with, a specific target molecule.

"Peptidomimetic" refers to a molecule having activity, including biological activity, that resembles that of a polypeptide or is substantially the same as a polypeptide. Morphine, for example, is a peptidomimetic of endorphin peptide. In some embodiments, a peptidomimetic is a small protein-like polymer designed to mimic the functionality of a peptide. Peptidomimetics useful as connecting groups for some compounds of the invention in the present invention include peptoids and β-peptides. The composition and biological activity of peptidomimetics and use of peptidomimetics in targeted diagnostics and therapeutics are further described in the following references: (1) A. Giannis and T. Koiter, *Peptidomimetics for Receptor Ligands—Discovery, Development, and Medical Perspectives,* Angewandte Chemie International Edition In English, vol. 32, 1993, pg. 1244-1267; (3) Peptidomimetics, Accounts of Chemical Research, Vol. 41, No. 10, October 208, 1231-1232, by Wu and Gellman; and (3) Patch, J. A. et al., *Versatile oligo (N-substituted) glycines: The many roles of peptoids in drug discovery,* Pseudo-Peptides in Drug Discovery 2004, 1-31 P. E. Nielsen.

As used herein, an "electron withdrawing group" (abbreviated as "EWG") refers to a chemical group that draws electrons or electron density from a center, such of an aromatic group or heteroaromatic group of an optical dye. In some embodiments, the electron withdrawing group(s) are independently selected from cyano (—CN), carbonyl (—CO), carboxylate (—$CO_2R^a$), halo (—F, —Cl, —Br, —I, —At), carbamate (—$CONR^bR^c$), acyl (—$COR^d$), nitro (—$NO_2$), sulfinyl (—$SOR^e$), sulfonyl (—$SO_2R^f$, —$SO_2OR^g$, and —$PO_3R^hR^i$, wherein in the context of this description, $R^a$-$R^i$ are independently selected to enhance biological and/or physiochemical properties of the optical agents of the invention. In some instances, $R^a$-$R^i$ are independently selected from any one of a hydrogen atom, an anionic functional group (e.g., carboxylate, sulfonate, sulfate, phosphonate or phosphate) and a hydrophilic functional group (e.g., hydroxyl, carboxyl, sulfonyl, sulfonato or phosphonato). In other instances, $R^a$-$R^i$ are independently selected from hydrogen, $C_{1\text{-}10}$ alkyl, $C_{5\text{-}10}$ aryl, $C_{5\text{-}10}$ heteroaryl, —$(CH_2)_nOH$, —$(CH_2)_nCO_2H$, —$(CH_2)_nSO_3H$, —$(CH_2)_nSO_3$—, —$(CH_2)_nOSO_3H$, —$(CH_2)_nOSO_3$—, —$(CH_2)_nNHSO_3H$, —$(CH_2)_nNHSO_3$—, —$(CH_2)_nPO_3H_2$, —$(CH_2)_nPO_3H$—, —$(CH_2)_nPO_3$—, —$(CH_2)_nOPO_3H_2$, —$(CH_2)_nOPO_3H$— and —$(CH_2)_nOPO_3$, wherein n is an integer from 1 to 10. In one example of this embodiment, the EWG(s) are independently selected from is —CN, halo, —$CO_2R^{76}$, —$COR^{77}$, —$NO_2$, —$SO_2R^{78}$, or —$SO_2NR^{79}R^{80}$, wherein each of $R^{76}$-$R^{80}$ is independently H or $C_1$-$C_{10}$ alkyl. In an embodiment, an EWG is located at the terminus of a substituent arm of an aromatic group or heteroaromatic group of an optical dye.

As used herein, an "electron donating group" (abbreviated as "EDG") refers to a chemical group that releases electrons or electron density to a center, such as an aromatic group or heteroaromatic group of an optical dye. In some embodiments, the electron donating group(s) are independently selected from $C_1$-$C_{10}$ alkyl, $C_5$-$C_{10}$ aryl, $(CH_2)_zOH$, —$OR^j$, —$SR^k$, —$NR^lR^m$, —$N(R^n)COR^o$, and —$P(R^p)$, wherein in the context of this description, $R^j$-$R^p$ are independently selected to enhance biological and/or physiochemical properties of the optical agents of the invention and wherein z is selected from the range of 1 to 10. In some instances, $R^j$-$R^p$ are independently selected from any one of a hydrogen atom, an anionic functional group (e.g., carboxylate, sulfonate, sulfate, phosphonate or phosphate) and a hydrophilic functional group (e.g., hydroxyl, carboxyl, sulfonyl, sulfonato or phosphonato). In other instances, $R^j$/$R^p$ are independently selected from hydrogen, $C_{1\text{-}10}$ alkyl, $C_{5\text{-}10}$ aryl, $C_{5\text{-}10}$ heteroaryl, —$(CH_2)_nOH$, —$(CH_2)_zCO_2H$, —$(CH_2)_zSO_3H$, —$(CH_2)_nSO_3^-$, —$(CH_2)_zOSO_3H$, —$(CH_2)_zOSO_3^-$, —$(CH_2)_zNHSO_3H$, —$(CH_2)_zNHSO_3^-$, —$(CH_2)_zPO_3H_2$, —$(CH_2)_zPO_3H^-$, —$(CH_2)_zPO_3^=$, —$(CH_2)_zOPO_3H_2$, —$(CH_2)_zOPO_3H^-$ and —$(CH_2)_zOPO_3^=$ where z is an integer from 1 to 10. In one example of this embodiment, the EDG(s) are independently $C_1$-$C_6$ alkyl, —$OR^{70}$, —$SR^{71}$, —$NR^{72}R^{73}$, or —$NR^{74}COR^{75}$, wherein each of $R^{70}$-$R^{75}$ is independently H or $C_1$-$C_{10}$ alkyl. In an embodiment, an EDG is located at the terminus of a substituent arm of an aromatic group or heteroaromatic group of an optical dye.

In embodiments, two substituents, such as EDG and EWG substituents, on a compound of the invention can act in what is known as a "push-pull" arrangement. In embodiments of the "push-pull" arrangement, the electron density of the compound or a portion thereof, such as an aryl or heteroaryl group, is polarized due in part to the location of an EWG and EDG on the compound. In embodiments of the "push-pull" arrangement, an EWG is positioned at a terminus of a substituent arm of the structure and an EDG is positioned at a terminus of a different substituent arm of the structure. In embodiments of the "push-pull" arrangement, an EWG is positioned at one end of a π bond and an EDG is positioned at the other end of a π bond. In an embodiment, an EWG is positioned para- to an EDG in a six-membered ring structure. In an embodiment, an EWG is positioned trans- to an EDG in an alkylene structure. In some embodiments, compounds having the "push-pull" arrangement exhibit a shift in the optical absorbance and emission spectrum as compared to compounds not having the "push-pull" arrangement.

"Optical agent" generally refers to compounds, compositions, preparations, and/or formulations that absorb, emit, or scatter electromagnetic radiation of wavelength generally in the range of 350-1300 nanometers, within a biologically relevant environment or condition. In some embodiments, optical agents of the invention, when excited by electromagnetic radiation, undergo emission via fluorescence or phosphorescence pathways. These pathways are useful for diagnostic imaging, visualization, or organ function monitoring. Compounds belonging to this class are commonly referred to as "optical imaging agents", "optical visualization agents" or "optical contrast agents." The invention provides tissue sealants and closure devices that function as an optical agent, such as an optical visualization agent.

As used herein, a "chromophore" is a compound or functional group of a compound that results in absorption of electromagnetic radiation, preferably for some applications electromagnetic radiation having wavelengths in the UV (e.g. 200 nm to 350 nm), visible (e.g. 350 nm-750 nm) or near IR (750 nm 1300 nm) of the electromagnetic spectrum.

As used herein, a "fluorophore" is a compound or functional group of a compound that results in absorption of electromagnetic radiation and subsequent fluorescence. Preferably for some applications incorporation of a fluorophore results in compounds of the invention that absorb electromagnetic radiation and generate fluorescence having wavelengths in the LA/ (e.g. 200 nm to 350 nm), visible (e.g. 350 nm to 750 nm) or near IR (750 nm-1300 nm) of the electromagnetic spectrum. In some embodiment, incorporation of a fluorophore results in compounds having an appreciable quantum yield for fluorescence, such as a quantum yield over the range of 0.001 to 1, 0.01 to 1, optionally 0.1 to 1. Optical agents of the present invention can contain fluorophores. Fluorophores can be functional groups in a molecule which absorb electromagnetic radiation of first specific wavelengths and re-emit energy at second specific wavelengths. The amount and wavelengths of the emitted electromagnetic radiation depend on both the fluorophore and the chemical environment of the fluorophore. The term "fluorophore" may be abbreviated throughout the present description as "FL". In aspects of the invention, fluorophores emit energy in the visible (e.g. 350 nm to 750 nm) and NIR regions (e.g., 750-1300 nm) of the electromagnetic spectrum.

As used herein, the term "luminescence" refers to the emission of electromagnetic radiation from excited electronic states of atoms or molecules. Luminescence generally refers to electromagnetic radiation emission, such as photoluminescence, chemiluminescence, and electrochemiluminescence, among others. In photoluminescence, including fluorescence and phosphorescence, the excited electronic state is created by the absorption of electromagnetic radiation. Luminescence detection involves detection of one or more properties of the luminescence or associated luminescence process. These properties can include intensity, excitation and/or emission spectrum, polarization, lifetime, and energy transfer, among others. These properties can also include time-independent (steady-state) and/or time-dependent (time-resolved) properties of the luminescence. Representative luminescence techniques include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others. By way of example, when an optical agent is used in the present invention, it is desirable that the wavelength of radiation be non-ionizing and be such that it excites the optical agent. This excitation can cause a bond of the molecule to break and can lead to creation of one or more appropriate radical(s). This excitation can also cause the molecule to emit part of the absorbed energy at a different wavelength. Such emission can be detected using fluorometric techniques as described above. One skilled in the art can readily determine the most appropriate treatment and optional detection technique based, at least in part, on the specific therapeutic agent(s) administered and/or the particular use (e.g., tissue to be treated).

"Optical condition" includes one or more of the following: the fluorescence quantum yield; fluorescence intensity; fluorescence excitation wavelength, wavelength distribution or spectrum; emission wavelength, wavelength distribution or spectrum; Stokes shift; color; absorption maximum or spectrum; reflectance; phosphorescence; chemiluminescence; scattering; optoacoustic property; and/or other observable and/or measurable spectral property or phenomenon.

Methods of this invention comprise the step of administering an "effective amount" of the present diagnostic and therapeutic compositions, formulations and preparations containing the present compounds or compositions, to diagnose, image, monitor, evaluate, treat, reduce, alleviate, ameliorate or regulate a biological condition and/or disease state in a patient. The term "effective amount," as used herein, refers to the amount of the diagnostic and therapeutic formulation, that, when administered to the individual is effective to diagnose, image, monitor, evaluate, treat, reduce alleviate, ameliorate or regulate a biological condition and/or disease state. As is understood in the art, an effective amount of a given composition or formulation will depend at least in part upon the mode of administration (e.g., intravenous, oral, topical administration), any carrier or vehicle employed, and the specific individual to whom the formulation is to be administered (age, weight, condition, sex, etc.). The dosage requirements needed to achieve the "effective amount" vary with the particular formulations employed, the route of administration, and clinical objectives. Based on the results obtained in standard pharmacological test procedures, projected daily dosages of active compound or composition can be determined as is understood in the art.

In an embodiment, an effective amount of a compound or composition of the invention is a therapeutically effective amount. As used herein, the phrase "therapeutically effective" qualifies the amount of compound or composition administered in the therapy. This amount achieves the goal of ameliorating, suppressing, eradicating, preventing, reducing the risk of, or delaying the onset of a targeted condition. In an embodiment, an effective amount of a compound or composition of the invention is a diagnostically effective amount. As used herein, the phrase "diagnostically effective" qualifies the amount of compound or composition administered in diagnosis, for example of a disease state or other pathological condition. The amount achieves the goal of being detectable while avoiding adverse side effects found with higher doses. In an embodiment, an active ingredient or other component is included in a therapeutically acceptable amount. In an embodiment, an active ingredient or other component is included in a diagnostically acceptable amount.

It is contemplated that the compounds and pharmaceutically acceptable salts of the invention can be used as part of a combination. The term "combination" means the administration of two or more compounds directed to a target condition. The treatments of the combination generally can be co-administered in a simultaneous manner. Two compounds can be co-administered as, for example: (a) a single formulation (e.g., a single capsule) having a fixed ratio of active ingredients; or (b) multiple, separate formulations (e.g., multiple capsules) for each compound. The treatments of the combination can alternatively (or additionally) be administered at different times.

In certain embodiments, the invention encompasses administering optical agents useful in the invention to a patient or subject. A "patient" or "subject", used equivalently herein, refers to an animal. In particular, an animal refers to a mammal, preferably a human. The subject can either: (1) have a condition able to be monitored, diagnosed, prevented and/or treated by administration of an optical agent of the invention; or (2) is susceptible to a condition that is able to be monitored, diagnosed, prevented and/or treated by administering an optical agent of the invention.

When used herein, the terms "diagnosis", "diagnostic" and other root word derivatives are as understood in the art and are further intended to include a general monitoring, characterizing and/or identifying a state of health or disease. The term is meant to encompass the concept of prognosis. For example, the diagnosis of cancer can include an initial determination and/or one or more subsequent assessments regardless of the outcome of a previous finding. The term does not necessarily imply a defined level of certainty regarding the prediction of a particular status or outcome.

As defined herein, "administering" means that a tissue sealant, closure device or a component of a tissue sealant or closure device, is provided to a patient or subject, for example in a therapeutically effective amount. The invention includes methods for a biomedical procedure wherein a therapeutically or diagnostically effective amount of a compound having any one of formulas (FX1)-(FX13) is administered to a patient in need of treatment, for example to a patient undergoing treatment for a wound, puncture, opening or access site in vascular tissue. Administering can be carried out by a range of techniques known in the art including parenteral administration including intravenous, intraperitoneal or subcutaneous injection or infusion, topical or transdermal absorption through the skin, or by inhalation, for example. The chosen route of administration may depend on such factors as solubility of the compound or composition, location of targeted condition, and other factors which are within the knowledge of one having ordinary skill in the relevant art.

"Topical administration" includes the use of transdermal administration, such as transdermal patches or iontophoresis devices.

"Parenteral administration" includes subcutaneous injections, intravenous injections, intraarterial injections, intraorbital injections, intracapsular injections, intraspinal injections, intraperitoneal injections, intramuscular injections, intrasternal injections, and infusion. Dosage forms suitable for parenteral administration include solutions, suspensions, dispersions, emulsions, and any other dosage form that can be administered parenterally.

As used herein, the term "pharmaceutically acceptable" means approved by a regulatory agency of an appropriate federal or state government; or listed in the U.S. Pharmacopoeia or other generally recognized pharmacopoeia for use in animals, and more particularly in humans; or does not impart significant deleterious or undesirable effect on a subject to whom it is administered and in the context in which it is administered.

As will be clear to those of ordinary skill in the art, the groups and structures described herein as portions of the compounds of the invention may be defined as if they are separate valence-satisfied chemical structures. It is intended that when a group is described or shown as being a substituent of another group, that the group be viewed as having a valency to allow this binding to occur.

One aspect of the invention is directed to an optically functional tissue sealant comprising an adhesive material and an optical dye covalently bound to or rioncovalently associated with the adhesive material. The adhesive material is activated to form a seal upon a biological tissue, for example, by being placed into physical contact with the biological tissue or application of an external stimulus (e.g., light, chemical initiator, heat etc.). Typically, the biological tissue is wounded biological tissue and surrounding tissue. Another aspect of the present invention is directed to a composition comprising a vasculature closure device and an optical dye covalently bound to or noncovalently associated with the device. The vasculature closure device is activated to form a seal, clot, plug or structure to close a vasculature opening, by being placed into physical contact with the vascular tissue or application of an external stimulus (e.g., light, chemical initiator, heat etc.). Commonly, for example, the opening is a puncture in a vasculature wall.

In specific embodiments, the optical dye has a detectable optical condition upon or after activation/application of the tissue sealant or closure device that is distinguishable from the optical condition prior to activation/application of the tissue sealant or closure device. In this way, the optical condition of the optical dye changes in response to activation/application of the tissue sealant or closure device and corresponding formation of the seal upon the wounded biological tissue. For instance, the optical dye may not absorb significantly in the visible region of the electromagnetic spectrum prior to activation/application of the tissue sealant or closure device, and upon or after activation/application of the tissue sealant or closure device, the optical dye undergoes a detectable change such that it absorbs appreciably in the visible region of the electromagnetic spectrum, or vice versa. Similarly, the optical dye may not fluoresce significantly upon exposure to visible or infrared light prior to activation/application of the tissue sealant or closure device, and upon or after activation/application of the tissue sealant or closure device, the optical dye undergo a change such that it exhibits measurable fluorescence when excited by light in the visible or infrared regions of the electromagnetic spectrum, or vice versa. Alternatively, the optical dye emits light corresponding to a first wavelength or first wavelength distribution corresponding to a first color prior to activation/application of the tissue sealant or closure device, and upon or after activation/application of the tissue sealant or closure device, the optical dye emits light having a second wavelength or second wavelength distribution corresponding to a second color that is distinguishable from the first color, optionally visually distinguishable. A variety of optical condition changes are contemplated, including changes in absorbance, reflectance, fluorescence, phosphorescence, chemiluminescence, scattering, optoacoustic property, or other detectable spectral properties. Advantageously, the compositions of the invention can be utilized in the treatment and repair of wounded biological tissue, and the efficacy of such treatment may be optically detected and evaluated by monitoring the change in the optical condition of the optical dye to evaluate the therapeutic outcome (e.g., determine the relative success of the treatment), such as evaluating establishment and maintenance of hemostasis.

Tissue Sealants

As noted above, some of the tissue sealants of the invention comprise an adhesive material component. In general, a wide variety of adhesive materials may be employed in this aspect of the invention. Adhesive materials generally refer to materials that are used to decrease or prevent the migration of fluid (e.g., blood) from or into a tissue. Sealants are typically applied to a tissue and then locally activated, for example via initiating cross linking or polymerization reactions, or otherwise processed. In some embodiments, for example, the adhesive material is activated by reaction with substances naturally present in the blood and/or tissue and/or by reaction of the additional tissue sealant components, such as chemical initiators. In some embodiments, for example, the adhesive material is activated by exposure to electromagnetic radiation. Adhesive materials may also cross-link in situ by reacting with the tissue surface. Adhesive material activation generally refers to the initiation of seal or clot formation according to the particular mechanism by which the adhesive material operates to form a seal and/or clot upon the wounded biological tissue. The same adhesive material materials may also be used to adhere structures or tissues together, either when applied between them and activated, or when used to encase junctions of tissue and/or devices. Crosslink and/or cross-linking reactions (including polymerization and gelling reactions) generically refer to the joining of smaller entities to form a structure, such as a polymer network, by physical or chemical processes.

The adhesive material may comprise effective amounts of any of several classes of compounds. Where the adhesive material comprises proteins or other polypeptides, the components of the tissue sealants, such as the adhesive material, may be derived from natural materials, or may be materials produced by molecular techniques, or mutants of natural proteins, or produced by chemical modification of proteins. Combinations of various tissue sealant components are contemplated in the invention. Exemplary classes of tissue sealant components are listed herein, and the particular examples in each class are to be construed as exemplary rather than limiting.

Various biological substances contribute to tissue repair and, as a result, hemostasis. Blood coagulation is a relatively complex cascade of events that result in the repair of damaged tissue (e.g., by way of clotting or the formation of fibrin strands). During the repair of a tissue wound or injury, whether accidental or intentional (e.g., arterial puncture for diagnostic or treatment purposes or traumatic injury), processes that release several substances occur, and these substances may contribute to the mechanisms of tissue repair including hemostasis. Some of these substances are present in plasma under normal conditions and undergo modifications during the tissue repair process. Other substances are present in the blood cells under normal conditions and are released from these cells during the tissue repair process. Additionally or alternatively, these and other substances may be applied to the wounded biological tissue from an exogenous source; that is, these substances can be comprised in the tissue sealant. Several of the various factors contributing to the natural coagulation cascade, their approximate molecular weights, and typical plasma concentrations are illustrated in Table 1:

TABLE 1

Plasma concentrations of blood coagulation factors

| Component | Molecular Weight (Da) | Plasma Concentration (µg/ml) | Plasma Concentration (µM) |
|---|---|---|---|
| Fibrinogen (I) | 330,000 | 3000 | 9.09 |
| Prothrombin (II) | 72,000 | 100 | 1.388 |
| Factor V | 330,000 | 10 | 0.03 |
| Factor VII | 50,000 | 0.5 | 0.01 |
| Factor VIII | 330,000 | 0.1 | 0.0003 |
| Factor IX | 56,000 | 5 | 0.08928 |
| Factor X | 58,800 | 8 | 0.13605 |
| Factor XI | 160,000 | 5 | 0.031 |
| Factor XII | 80,000 | 30 | 0.375 |
| Factor XIII | 320,000 | 10 | 0.03124 |
| Protein C | 62,000 | 4 | 0.0645 |
| Protein S | 69,000 | 10 (free) | 0.1449 |
| Protein Z | 62,000 | 2.2 | 0.0355 |
| Prekallikrein | 86,000 | 50 | 0.5814 |
| High MW Kininogen | 110,000 | 70 | 0.6363 |
| Fibronectin | 450,000 | 300 | 0.6667 |
| Antithrombin III | 58,000 | 290 | 5 |
| Plasminogen | 90,000 | 216 | 2.4 |
| Urokinase | 53,000 | 0.1 | 0.001887 |
| Heparin Cofactor II | 66,000 | 90 | 1.3636 |
| Alpha$_2$-Antiplasmin | 63,000 | 60 | 0.9524 |
| Protein C Inhibitor | 57,000 | 4 | 0.0702 |
| Alpha$_2$-Macroglobulin | 725,000 | 2100 | 2.8966 |

One physiological pathway that is involved in hemostasis and tissue repair, the extrinsic pathway, is initiated by the release of Tissue Factor (also known as thromboplastin or factor III) from injured cells. Upon contact with factor VII in the surrounding plasma, factor X activator is formed. Together with factor V; along with associated phospholipids and calcium, prothrombin is converted into thrombin. The enzymatic activity of thrombin results in the cleavage of fibrinogen to form fibrin monomers, which aggregate and are covalently crosslinked via the activity of factor XIIIa (which is formed via thrombin activation of factor XIII). (See FIG. 1).

Another physiological pathway that is involved in hemostasis and tissue repair, the intrinsic pathway, involves negatively charged surfaces that are exposed to the action of factor XII and prekallikrein in the bloodstream. Factor XII is activated to factor XIIa which activates factor XI to factor XIa. Factor XIa activates factor IX to factor IXa. Factor IXa, factor VIIIa (formed from factor VIII, the antihemophilic factor), phospholipids, and free calcium ions are required for the formation of the tenase complex (Factor IXa-Factor VIIIa complex), which activates factor X. Factor Xa, factor Va, phospholipids, and free calcium ions are generally required for the formation of the prothrombinase complex (Factor Xa-Factor Va complex), which activates prothrombin to thrombin, (See FIG. 1).

Activation of coagulation takes place along the above-described extrinsic and/or intrinsic pathways, which converge to form a common pathway leading to clot formation. In the common pathway, the activated factor Xa (formed from either one or both of the extrinsic and intrinsic pathways) activates prothrombin (factor II) to generate the protease thrombin. Assembly of the plasma prothrombinase complex on the surface of activated platelets in the presence of factor V, another cofactor, enhances the efficiency of prothrombin activation to thrombin on the platelet surface. Thrombin cleaves fibrinogen, which is a large, asymmetric, soluble protein with a molecular weight of about 330 to 340 kilodaltons consisting of three pairs of polypeptide chains: Aα, Bβ, and γ. Thrombin first removes small peptides from the Aα chain of fibrinogen to form Fibrin I, which polymerizes end to end; further thrombin cleavage of small peptides from the Bβ chain leads to formation of Fibrin II molecules, which polymerize side to side and are then cross-linked via the γ subunits by the plasma glutaminase (factor XIII, the fibrin stabilizing factor) to form an insoluble fibrin clot. (See FIG. 1).

Thrombin, in particular, has multiple actions during coagulation in addition to the cleavage of fibrinogen to fibrin. For instance, it activates platelets, exposing their procoagulant activity (e.g., binding sites for the prothrombinase complex) and induces the release of platelet-aggregating substances such as thromboxane, $Ca^{2+}$, adenosine diphosphate (ADP), von Willebrand factor, fibronectin, and thrombospondin. Thrombin cleaves factors VIII and Va, thus augmenting the coagulation cascade, and also cleaves plasma glutaminase (i.e., factor XIII), the enzyme that crass-links fibrin and stabilizes the fibrin clot. Thrombin acts on the endothelium by binding to the surface protein thrombomodulin to activate protein C, which is a potent inactivator of factors Va and VIIIa and also stimulates fibrinolysis. Thrombin also causes endothelial cell contraction. Conversely, endothelium can bind and inactivate thrombin, and in some cases may generate the vasodilatory substance prostacyclin in response to thrombin. Thus, thrombin activation contributes to the limitation as well as the initiation of clotting. (See FIG. 1).

Coagulation factors are substances in the blood that are involved in the clotting process and the maintenance of the hemostasis for tissue repair. As discussed above in connection with FIG. 1, blood coagulation is the sequential process by which the multiple coagulation factors of the blood (and/or the tissue sealant components) interact, ultimately resulting in an insoluble fibrin network. In some embodiments, the tissue sealant component, such as the adhesive material, comprises a coagulation factor. Such factors may be selected to participate in the intrinsic, extrinsic, or common pathways of the coagulation cascade and may comprise, for instance, any one or more of the factors illustrated in FIG. 1. These factors can be derived from a variety of natural sources, such as from human or bovine plasma, or can be recombinantly produced by molecular techniques.

As noted above, a key role of thrombin in the coagulation cascade is its ability to catalyze the conversion of fibrinogen (which may be present at the wounded biological tissue site and/or exogenously supplied as a tissue sealant component) to form fibrin monomers. As noted above, thrombin also plays other roles in coagulation such as, for example, inducing coagulation by activating platelets that trigger the coagulation cascade, and catalyzing the conversion of factor XIII to activated factor XIII (i.e., factor XIIIa) which initiates the covalent crosslinking of the fibrin clot. Once formed, fibrin monomers aggregate together to form a fibrin clot. The clot may then be further stabilized by covalent crosslinking via factor XIIIa. In various embodiments, an effective amount of thrombin is comprised as a component in the tissue sealant, such as the adhesive material. Thrombin can be derived from a variety of natural sources, or can be recombinantly produced by molecular techniques.

Also participating in the coagulation processes, and which may be comprised in effective amounts in the tissue sealant, are the platelet derived factors. This comprises, for example, the so-called platelet factors 1 to 4: platelet factor 1, which accelerates the formation of thrombin; platelet factor 2, which accelerates the thrombin-fibrinogen reaction; platelet factor 3, which acts with plasma thromboplastin factors to convert prothrombin to thrombin; and platelet factor 4, which has antiheparin properties. Other factors that may be comprised in the tissue sealant are the platelet-derived growth factor (PDGF), a potent mitogen, which, for instance, promotes the proliferation of fibroblast cells needed in tissue repair and the epidermal growth factor (EGF), which promotes epithelial growth and is present in the platelets. Another component present in plasma that may be comprised in the tissue sealant, such as the adhesive material, is the protein fibronectin, which plays a role in cell proliferation and in fibrin interaction.

In various embodiments, the tissue sealant, optionally the adhesive material component, comprises effective amounts of one or more components of the natural coagulation cascade; that is, the coagulation factors and/or platelet factors discussed above. This may comprise, but is not limited to, the various factors and components involved in the natural coagulation cascade illustrated in FIG. 1. Such factors and components comprise, among others, fibrin, fibrinogen, thrombin, prothrombin, factors V, VII, VIII, IX, X, XII, and XIII, including their activated forms, platelet factors 1, 2, 3, and 4, prothrombin, and other tissue factors and combinations thereof. These factors and components can be derived from a variety of natural sources, or can be recombinantly produced by molecular techniques.

The tissue sealant, optionally the adhesive material component, may also comprise effective amounts of proteins or other compounds which activate or catalyze the natural pathways of clotting; that is, coagulation activators. These comprise, but are not limited to, bismuth compounds (e.g., bismuth subgallate), a source of calcium ions (for example, calcium salts such as calcium chloride, or calcium glucuronate), collagen, denatured collagen (gelatin), desmopressin and analogs thereof, fibronectin, thrombin, thromboplastin, and combinations thereof. Additionally or alternatively, vitamin K may contribute to activation of coagulation.

In certain embodiments, the presence of an effective amount of collagen in the compositions may enhance the mechanical, chemical and physical properties of the tissue sealant. For instance, collagen can increase the viscosity of the composition, making it easier to apply to the wounded biological tissue and surrounding tissue without substantial run-off. Collagen may also reinforce the resulting seal, and may activate blood platelets which can further contribute to the hemostatic process. Examples of collagenic materials that may be comprised in the compositions comprise nonfibrillar and fibrillar collagen. Nearly thirty different types of collagen are known in the art (e.g., Type I, II, III, IV, V, VI, VII, VIII, IX, X, XI, XII, XIII, XIV, XV, XVI, XVII, XVIII, XIX, XX, XXI, XXII, XVIII, XXIV, XXV, XXVI, XXVII, and XXVIII), each of which and others may be included in the compositions of the invention, individually or in combination. Collagen in the compositions can be derived from a variety of natural sources, or can be recombinantly produced by molecular techniques.

As noted above, the tissue sealant, optionally the adhesive material component, may comprise an effective amount of a calcium ion source. In general, calcium ions are involved in the activation of various clotting factors in the coagulation cascade (see FIG. 1), and can also be used to form microfibrils from fibrillar collagen. The calcium ion source in the composition may be provided, for example, as calcium chloride, calcium glucuronate, or another pharmaceutically acceptable calcium salt. Other pharmaceutically acceptable salts are described below.

As an alternative, a sufficient level of calcium ions may already be present at the wound site, i.e., endogenously from the body, in which case an additional calcium ion source may not be necessary for certain compositions of the invention. Generally, the amount of a component of the present tissue sealants and devices employed in the present compositions is an amount that is effective to promote seal formation or at least partial occlusion of a vasculature opening upon application to the biological tissue. The amount of calcium ions added to the composition in the form of a calcium ion source, or any other component discussed herein, may also depend on the presence and amount, or the absence, of other components in the tissue sealant and/or at the site of application.

The tissue sealant, optionally the adhesive material component, may also comprise effective amounts of various components that act by activating, aggregating, or stimulating platelets; that is, platelet activators. These comprise, for example, atrial naturetic factor (ANF), cycloheximide, ethamsylate, hemoglobin, N-monomethyl L-arginine, platelet activating factor, phorbols and phorbol esters, prostaglandins, small nucleotides (including cAMP, cGMP, and ADP), thromboxanes and analogs thereof (such as U4-6619 by Upjohn), and combinations thereof. Additionally or alternatively, nonabsorbable powders (such as talc), and denatured or surface-absorbed proteins may be comprised to activate platelets.

Additionally or alternatively, the tissue sealant, optionally the adhesive material component, may comprise effective amounts of components that act by local vasoconstriction; that is, vasoconstrictors. Nonlimiting examples comprise adrenochrome, antihistamines (including antazoline), cocaine, epinephrine (adrenaline), oxymetazofine, prostaglandin 2-alpha, tetrahydrozoline, thromboxane A2, vasopressin and analogs and combinations thereof.

The tissue sealant, optionally the adhesive material component, may also comprise an effective amount of one or more inhibitors of plasmin-driven fibrinolytic housekeeping functions, e.g., components that may minimize or prevent destruction or inactivation of clotting reactions such as, for example, fibrinolysis inhibitors. Such inhibitors may increase the residence time of the resulting clot when the tissue sealant is applied to tissues having an inherently high fibrinolytic activity (e.g., lung or prostate tissue) or where fibrinolytic activity is artificially increased (e.g., by the ingestion of certain foods, beverages, or pharmaceuticals). Nonlimiting examples comprise eosinophil major basic protein, aminocaproic acid, tranexamic acid, aprotinin (Trasylol™), plasminogen activator inhibitor, plasmin inhibitor, alpha-2-macroglobulin, alpha-2-antiplasmin, adrenoreceptor blockers, and combinations thereof.

The tissue sealant, optionally the adhesive material component, may also comprise an effective amount of components that strengthen clots when formed; that is, crosslinkers. Nonlimiting examples comprise entactin, transglutaminases, chemical crosslinking agents and bioabsorbable polymers such as, for instance, polyanionic polysaccharides (e.g., glycosaminoglycans such as, for example, hyaluronic acid and salts thereof, chondroitin sulfate (including the 2-, 4-, 6-, and 4,6-sulfated varieties, and varieties with little or no sulfonation) and salts thereof), carboxymethylcellulose, carboxymethylamylose, dermatin sulfate, dermatin-6-sulfate), chitin, chitosan, polyglycolide, polylactide, polycaprolactone, alginic acid, dextran, and copolymers, or combinations thereof.

The tissue sealant, optionally the adhesive material component, may also comprise an effective amount of components containing non-protein polymers that may locally viscosity or gel blood or plasma, by interaction with proteins, by tamponnade, or by other mechanisms; that is, polymeric hemostats. Nonlimiting examples comprise oxidized cellulose, "Vicryl" and other polyhydroxyacids, microfibrillar collagen, crosslinked collagen, collagen sponges, chitosan, alginate, polyacrylic acids, pentosan polysulfate, carrageenan, polyorthoesters (e.g., Alzamer™), and combinations thereof.

The tissue sealant, optionally the adhesive material component, may also comprise an effective amount of various materials that form a barrier to blood leakage by mechanical means not typically directly related to the natural clotting mechanisms; that is, barrier formers. These may comprise collagen (described above), denatured collagen (i.e., gelatin), oxidized cellulose, fibrin, thrombin, ionically or hydrogen-bond crosslinked natural and synthetic polymers including chitin, chitosan, alginate, pectin, carboxymethylcellulose, and poloxamers such as Pluronic™ surfactants, polyethylene glycol (PEG) based tissue sealants such as DuraSeal®, succinimide-derivatized PEG, and thiol-derivatized PEG, polyisocyanate-, polyacrylate-, polyurethane-, and polyamide-based tissue sealants and combinations thereof. These may also comprise one or more polycyanoacrylates known in the art of tissue repair.

In some embodiments, the tissue sealant, optionally the adhesive material component, comprises an effective amount of fibrinogen and thrombin, for example, these components can be readily obtained from a number of commercial sources (e.g., Sigma Chemical Co. (St. Louis, Mo.), EMD Biosciences. Inc. (San Diego, Calif.), and American Diagnostica, Inc. (Stamford, Conn.)). Alternatively, these and other similar proteins and components discussed above can be derived from the plasma of any desirable species, or produced using molecular techniques (see, e.g., Prunkard et al., Nature Biotechnology 14, 867-871, (1996); PCT Patent Application WO 95/22249 to Velander; Karges and Metzner, Seminars in Thrombosis and Hemostasis 22, 427-436, (1996); Lewis et al., Biochemistry 36, 995-1002, (1997); Lai et al, J. Biol. Chem. 269, 24596-24601, (1994); Fischer et al., Thrombosis Res. 81, 157-162, (1996); Lord et al., Blood Coagulation and Fibrinolysis 4, 55-59, (1993); DiBella et al., I Biol. Chem. 270, 163-169, (1995); Roy et al., J. Biol. Chem. 270, 163-169, (1995)).

In some embodiments where the tissue sealant, optionally the adhesive material component, comprises an effective amount of fibrinogen and/or thrombin, the fibrinogen and thrombin used are of bovine or human origin or are produced by molecular techniques.

When the composition is to be used in humans, for certain applications it is preferable that the fibrinogen and thrombin are of human origin or are produced by molecular techniques. Additionally, when the fibrinogen is derived from human plasma it may be subjected to heat inactivation methods, or to solvent detergent methods, well known to those skilled in the art and intended to inactivate any viruses that might be present (see, e.g., Radosevich et al., "Fibrin Sealant: Scientific rationale, production methods, properties, and current clinical use," Vox Sang 72, 133-143, (1997)).

A number of crosslinkable and/or polymerizable materials are also known for tissue sealant materials, such as the adhesive material component, and may be provided in effective amounts as tissue sealant components in the composition described herein. These comprise, for example, crosslinkable materials that may be applied to tissue such as, for example, gels and hydrogels, bioabsorbable polymers, polysaccharides, polyamines, poly(hydroxylic) compounds, or other hydrophilic polymers (such as, for example, polyalkylene oxide or polyglycerol) and combinations thereof. Representative examples of tissue sealants and adhesive material components thereof, are described, for example, in U.S. Pat. No. 4,511,478 to Nowinski et al.; U.S. Pat. No. 4,741,872 to DeLuca et al.; U.S. Pat. No. 4,826,945 to Cohn et al.; U.S. Pat. No. 4,888,413 to Domb; U.S. Pat. No. 4,938,763 to Dunn et al.; U.S. Pat. No. 5,100,992 to Cohn et al.; U.S. Pat. No. 5,160,745 to DeLuca et al.; U.S. Pat. No. 5,527,864 to Suggs et al.; U.S. Pat. No. 6,056,970 to Greenawalt et al.; U.S. Pat. No. 6,162,241 to Coury et al.; U.S. Pat. No. 6,638,917 to Li et al.; U.S. Pat. No. 6,833,408 to Sehl et al.; U.S. Pat. No. 7,009,034 to Pathak et al.; U.S. Published Application No. 2006/0078536 to Kodokian et al.; and U.S. Published Application No. 200610079599 to Arthur.

The tissue sealant, optionally the adhesive material component, may also comprise effective amounts of materials that assist in photocuring or photopolymerizing the tissue sealant, for example, by the application or photons and/or energy to the tissue sealant (described in further detail below). Representative examples of tissue sealants including such materials are described, for example, in U.S. Pat. No. 5,292,362 to Bass et al.; U.S. Pat. No. 5,410,016 to Hubbell et al.; U.S. Pat. No. 5,827,265 to Glinksy et al.; U.S. Pat. No. 6,391,049 to McNally et al.; U.S. Pat. No. 7,073,510 to Redmond et al.; U.S. Pat. No. 7,077,839 to Hamblin et al.; U.S. Pat. No. 7,078,378 to Owen et al.; and PCT Patent Application WO 91/04073 to Oz et al.

In some embodiments, the tissue sealant, optionally the adhesive material component, comprises a component selected from the group consisting of collagen, fibrin, fibrinogen, fibronectin, prothrombin, thrombin, thromboplastin, factor V, factor X, factor XIII, a source of calcium ions, and combinations thereof. In these embodiments, the various tissue sealant components may replicate or augment the final stage of the coagulation cascade; e.g., the cleavage of fibrinogen into fibrin by the action of thrombin, and the covalent crosslinking of the fibrin polymer to produce the fibrin coagulum. Where exogenous fibrinogen is supplied to the wounded biological tissue via the tissue sealant, the concentration of the exogenous fibrinogen in the tissue sealant may be supraphysiologic. Representative examples of tissue sealants including fibrin, fibrinogen, prothrombin, thrombin, factor V, factor X, factor XIII, or a source of calcium ions that may be utilized in the compositions of the invention, and methods of producing such tissue sealants, are described, for example, in U.S. Pat. No. 4,298,598 to Schwarz et al.; U.S. Pat. No. 4,377,572 to Schwarz et al.; U.S. Pat. No. 4,427,650 to Stroetmann; U.S. Pat. No. 4,427,651 to Stroetmann; U.S. Pat. No. 4,627,879 to Rose et al.; U.S. Pat. No. 4,714,457 to Alterbaum; U.S. Pat. No. 4,909,251 to Seelich; U.S. Pat. No. 4,928,603 to Rose at al.; U.S. Pat. No. 5,030,215 to Morse et al.; U.S. Pat. No. 5,318,782 to Weis-Fogh; U.S. Pat. No. 5,585,007 to Antanavich et al.; U.S. Pat. No. 6,492,494 to Cedarholm-Williams; Reissued U.S. Pat. No. 39,192 to MacPhee et al.; Reissued U.S. Pat. No. 39,298 to MacPhee et al.; Reissued U.S. Pat. No. 39,321 to MacPhee et al.; EP 0 592 242 to Edwardson et al.; Australian Patent No. 75097/87; and JP 1-99565.

Currently, several tissue sealant products are commercially available in the United States and abroad, each of which may be provided in the compositions and devices of the invention, particularly as the adhesive material component. The components of these products vary, but each generally comprises effective amounts of one or more of fibrinogen, thrombin, factor XIII, and a source of calcium ions (e.g., calcium chloride). Exemplary commercially available fibrin-type tissue sealants comprise Beriplast® P (ZLB Behring, King of Prussia, Pa.); Bolheal® (Fujisawa Pharmaceuticals, Osaka, Japan); Crosseal® (Omrix Biopharmaceuticals, Ltd., Israel); Hemaseel® (Haemacure, Sarasota, Fla.); Quixil® (Omrix Biopharmaceuticals, Ltd., Israel); and Tisseel® (Baxter HealthCare Corp., Irvine, Calif.); and combinations thereof. Other commercially available tissue sealants that may be used comprise, for example, FloSeal® (gelatin matrix thrombin, Baxter HealthCare Corp., Irvine, Calif.), Thrombin-JMI® (thrombin, King Pharmaceuticals. Inc., Bristol, Tenn.), Gelfoam® (gelatin sponge, Pharmacia & Upjohn Company, Kalamazoo, Mich.), Surgicel® (oxidized cellulose, Ethicon, Somerville, N.J.), Actifoam® (collagen sponge, C.R. Bard, Inc., Murray Hill, N.J.), Avitene® (collagen fleece, C.R. Bard, Inc., Murray Hill, N.J.), NovoSeven® (recombinant factor Vila, Novo Nordisk A/S, Denmark), CoSeal® (polyethylene glycol, Baxter HealthCare Corp., Irvine, Calif.), Dermabond® (cyanoacrylate, Ethicon, Somerville, N.J.), and combinations thereof.

The compositions of the invention may also comprise effective amounts of one or more dendrimers and/or nanoparticles as a tissue sealant component. The use of dendrimers and nanoparticles in biological applications including, for example, wound healing, tissue repair, and preventing scar tissue formation is known in the art. See, e.g., Hartgerink et al., Science 294, 1684-88, (2001); Buxton et al, Circulation 108, 2737-42, (2003); Shaunak et al., Nature Biotechnology 22(8), 977-84, (2004); Lee et al., Nature Biotechnology 23, 1517-26, (2005); Aryal et al., J. Mater. Chem. 16, 4642-48, (2006); Ellis-Behnke et al., PNAS 103(13), 5054-59, (2006); Ellis-Behnke et al., Nanomedicine: Nanotechnology, Biology, and Medicine 2(4), 207-215, (2006); Sontjens et al., Biomacromolecules 7, 310-16, (2006); Tian et al., ChemMedChem 2(1), 129-36, (2006); Egertsdotter et al., Biomed. Eng. 555, (2007); and U.S. Pat. No. 6,685,730 to West et al.

In some embodiments, the amount of adhesive material present in the tissue sealants is, for example, at least sufficient to result in the activation and repair of wounded biological tissue; that is, the formation of a seal upon the wounded biological tissue. Where various tissue sealant components are supplied endogenously by the body, the relative amounts can differ depending on, for example, the age, sex, weight, diet, or general health of the patient, and/or the relative seventy of the wound. As noted above, where the tissue sealant comprises fibrin, fibrinogen, prothrombin, thrombin, factor V, factor X, factor XIII, a source of calcium ions, and combinations thereof, for example, these components may be comprised in the tissue sealant in amounts typically exceeding the normal amount endogenously provided by the body.

The minimum amount of tissue sealant that yields satisfactory results can vary from tissue sealant component(s) to tissue sealant component(s) and/or from patient to patient. Suitable amounts, therefore, may be determined by experimentation within the ambit of one skilled in the art, such as an appropriate medical professional. Where the tissue sealant is a commercially available tissue sealant, for example, it may be used as directed. The amount and type of tissue sealant will preferably comply with Food and Drug Administration (or other regulatory agency) regulations.

Vasculature Closure Devices

As noted above, the compositions and devices of the invention include vasculature closure devices. Vasculature closure devices generally refer to materials (e.g., plugs) that are used to occlude or form a mechanical barrier in a vasculature opening, for example to prevent the migration of fluid (e.g., blood) from or into vasculature tissue. Vasculature closure devices are typically inserted into a vasculature opening and then locally activated and/or crosslinked or otherwise processed (e.g., activated by substances naturally present in the blood and/or by reaction of the components of the vasculature closure devices). Activation generally refers to the initiation of a seal, clot or barrier formed according to the particular mechanism by which the closure device operates to form a seal, clot or barrier upon the vasculature opening. In this context, crosslink and/or crosslinking reactions (including polymerization and gelling reactions) generically refer to the joining of smaller entities to form a structure by any physical or chemical means.

In an embodiment, a vasculature closure device of the present invention comprises an active clotting agent. For example, a vasculature closure device of the present invention may comprise a collagen and/or thrombin plug. Vasculature closure devices of the present invention may also comprise one or more tissue sealants or tissue sealant components as described above. In an embodiment, a vascular closure device of the present invention comprises a plug for occluding an opening in vasculature and an optical dye bound to the plug, wherein the optical dye exhibits a first optical condition when the plug is in a first state and exhibits a second optical condition that is distinguishable from the first optical condition when the plug is in a second state different from the first state.

In another embodiment, a vascular closure device of the present invention comprises a plug for forming a mechanical barrier in a vasculature opening and an optical dye bound to the plug. In an embodiment, the optical dye bound to the plug exhibits a first fluorescence intensity when the vasculature opening is open and exhibits a second fluorescence intensity when the vasculature opening is closed, wherein the second fluorescence intensity is higher than the first fluorescence intensity. In an alternative embodiment, the optical dye bound to the plug exhibits a first color when the vasculature opening is open and a second color when the vasculature opening is closed, wherein the second color is different from the first color. In another embodiment, the optical dye bound to the plug exhibits a first fluorescence intensity when the plug is not incorporated into a clot and exhibits a second fluorescence intensity, higher than the first fluorescence intensity, when the plug is incorporated into a clot. In a preferred embodiment, the optical dye is bound to the plug by a covalent bond; even more preferably for certain applications, the optical dye is bound and/or tethered to the plug by means of a connecting group. In some embodiments, the optical dye is noncovafently associated with the plug.

Examples of vascular closure devices include Perclose™ suture mediated closure devices provided by Abbott Laboratories and Angio-Seal™ vascular closure devices provided by St. Jude Medical.

Optical Dyes

Tissue sealants and closure devices of the invention comprise an optical dye or combination of optical dyes. The optical dye has a detectable optical condition upon or after activation of the adhesive material and/or vasculature closure device that is distinguishable from the optical condition prior to activation of the adhesive material and/or vasculature closure device. For instance, a physical property of the optical dye may change in response to the activation of the adhesive material and/or vasculature closure device, which in turn triggers a change in the optical condition of the optical dye. Alternatively, a change in the environment in which the composition including the adhesive material and/or vasculature closure device and the optical dye is present may occur in response to the activation of the adhesive material and/or vasculature closure device, which in turn triggers a change in the optical condition of the optical dye. The optical dye having an optical condition may exhibit changes, for example, in its fluorescence quantum yield, fluorescence excitation wavelength, wavelength distribution, or spectrum, emission fluorescence excitation wavelength, wavelength distribution, or spectrum, absorbance, reflectance, phosphorescence, chemiluminescence, scattering, optoacoustic or other spectral properties upon and/or after activation of the adhesive material and/or vasculature closure device. The optical dye, therefore, exhibits an optical condition upon and/or after activation of the adhesive material and/or vasculature closure device that is distinguishable from the optical condition prior to activation of the adhesive material and/or vasculature closure device. In some embodiments, the optical condition exhibits a wavelength that changes in response to the activation of the adhesive material and/or vasculature closure device. The above-described property and/or environmental change that can occur in response to adhesive material and/or vasculature closure device activation and seal formation may result in, for example, the optical condition of the optical dye exhibiting an increase or decrease of fluorescence quantum yield at a particular wavelength, a change in the fluorescence spectrum, or a change in same other optical property including, for example, a change in the absorbance spectrum and/or a change in the emission spectrum.

In general, a wide variety of optical dyes may be employed in the compositions of the invention, provided they are responsive to the activation of the adhesive material and/or vasculature closure device (and, for example, corresponding changes in the environment and/or physical properties of the dye noted above) as described herein. It may be preferred that the optical dye is biocompatible and is relatively photostable (e.g., the dye generally withstands photobleaching).

In some embodiments, restriction of rotational movement (i.e., rotational freedom) of the optical dye can result in a change in the optical condition of the dye. In these embodiments, for example, restriction of rotational freedom of the optical dye may result in the optical dye losing or gaining excitation energy by fluorescence emission. Certain cyanine dyes, for example, exhibit little or no fluorescence when undergoing free rotation and molecular motion in solution. When free in solution such compounds can transition from the excited singlet state ($\Sigma_1$) to the ground state ($\Sigma_0$) in a radiationless process involving loss of excitation energy by rotation about the cyanine methine bond. It is believed that seal or clot formation resulting from the activated adhesive material and/or vasculature closure device prevents free rotation about the cyanine methine bond and causes the dye to lose excitation energy at least in part by fluorescence emission. The optical condition of the optical dye changes in response to being held in the rigidified seal or clot. Thus, the mechanism for the change in optical condition may involve the restriction of rotation of (or within) the optical dye molecule upon or after activation of the adhesive material to form a seal or clot. Accordingly, any optical dye having these or similar properties may be employed in the compositions of the invention. See, e.g., Haugland, Handbook of Fluorescent Probes and Research Chemicals, Sixth ed. (1996), Molecular Probes. Inc., Eugene, Oreg.

As noted above, other optical dyes may respond to an environmental change caused by adhesive material and/or vasculature closure device activation and seal or clot formation. Environmental changes that could result from tissue sealant and/or vasculature closure device activation and seal or clot formation comprise, for example, increases or decreases in hydrophobicity or hydrophilicity, pH, the presence or absence of certain components (such as factors in the coagulation cascade). For example, the optical dye molecule may have certain structural features such that their quantum yield and/or absorption maxima and/or emission maxima are sensitive to a more hydrophobic or hydrophilic environment. Dye compounds such as PRODAN (6-propionyl-2-dimethylaminonapthalene) and 2-(dimethylamino)naphthalene-6-sulfonamide, for example, have a large dipole moment in the excited state, as a consequence of charge delocalization between electron donating group(s) and electron accepting group(s). Additional environment-sensitive optical dyes capable of delocalizing electron density by way of conjugated electron donor/electron acceptor groups include, for example, derivatives of 2-dirnethylaminonaphthalene-6-sulfonamides and the isomeric species 5-dimethylaminon-aphthalene-1-sulfonamides, 4-(N-methylamino)-7-nitro-2,1, 3-benzoxadiazole, 6-anilinonaphthalene-2-sulfonamides, derivatives of pyridyloxazoles, 1-anilinonaphthalene-8-sulfonic acid, 2-anilinonaphthalene-6-sulfonic acid, 2-(p-toluidinyl)naphthalene -6-sulfonic acid, N-phenyl-1'-naphthylamine, thiazole orange, oxazole yellow, thiazole blue, thiazole green, 4-(dicyanovinyl)julolidine, 4-dimethylamino-4'-nitrostilbene, Nile Blue, Nile Red, and combinations thereof. See, e.g., Haugland, supra.

In some embodiments, for example, the optical dye is selected from the group consisting of an acridine dye, an anthraquinone dye, an azo dye, a bis-benzimidazole dye, a cyanine dye, a diazo dye, a phenanthridium dye, a phenothiazine dye, a phthalein dye, a pyrazine dye, a styryl dye, a triarylmethane dye, a xanthene dye, and combinations thereof.

Nonlimiting examples of acridine dyes in the compositions of the invention include acridine orange, acridine yellow, 9-aminoacridine, acriflavin, proflavin, and combinations thereof. Nonlimiting examples of anthraquinone dyes in the compositions of the invention include reactive blue and combinations thereof. Nonlimiting examples of azo and/or diazo dyes in the compositions of the invention include Evans blue, trypan blue, trypan red, orange B, polar yellow, orange I, orange II, methyl orange, FD&C Yellow No. 5, FD&C Yellow No. 6, and combinations thereof. Nonlimiting examples of bis-benzimidazole dyes in the compositions of the invention include Hoechst 33258, Hoechst 33342, and combinations thereof. Nonlimiting examples of cyanine dyes in the compositions of the invention include indocyanine green, thiazole orange and derivatives thereof (e.g., PO-PRO, BOPRO, YO-PRO, TO-PRO) as well as dimeric analogues (e.g., POPO, BOBO, YOYO, TOTO, JOJO, and LOLO), thiazole blue, thioflavin, and combinations thereof. In some embodiments, the optical dye is thiazole orange or a derivative thereof. Nonlimiting examples of phenanthridium dyes in the compositions of the invention include ethidium bromide, ethidium chloride, propidium iodide, and combinations thereof. Nonlimiting examples of phenothiazine dyes in the compositions of the invention include methylene blue, toluidine blue, azur (A, B), and combinations thereof. Nonlimiting examples of phthalein dyes in the compositions of the invention include phenolphthalein, phenolsulfophthlalein, and combinations thereof. Nonlimiting examples of triarylmethane dyes in the compositions of the invention include gentian violet, fuchsine, patent blue, patent blue V, isosulfan blue, brilliant blue FCF (i.e., FD&C Blue No. 1), brilliant blue R, brilliant blue G, and combinations thereof. Nonlimiting examples of xanthene dyes in the compositions of the invention include rhodamine, sulforhodamine, fluorescein, eosin B, eosin Y, rose bengal, pyronin G, pyronin J, pyronin Y, and combinations thereof. Carbocyanine dyes are another class of dye useful in the present invention.

A class of dyes particularly useful in the present tissue sealants and closure devices are pyrazine-containing dyes. In some embodiments, the pyrazine dye of a tissue sealant or closure device of the present invention has formula (FX14):

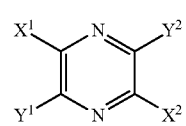

(FX14)

wherein $X^1$, $X^2$, $Y^1$, and $Y^2$ are selected from electron withdrawing groups and electron donating substituents. Electron withdrawing groups and electron donating groups are known in the art. Exemplary electron donating groups comprise, but are not limited to, N or O atoms with an electron pair available for extended localization, such as, for example, RO— or $(R_1)(R_2)N$—, wherein R, $R_1$, and $R_2$ are independently hydrogen or $C_1$-$C_{10}$ alkyl and wherein $R_1$ and $R_2$ can together form a five- or six-membered ring system. Exemplary electron withdrawing groups comprise, but are not limited to, —$NO_2$, —C(=O)—, —C(=S)—, —CN, —N(=O), —S(=O)$_2$—, —C=C(CN)$_2$, and (-)N=C(-)(-) where N and C can be part of a ring system.

Suitable pyrazine-containing dyes are described, for example, in International Patent Publication WO 2007/149478, which is hereby incorporated by reference. Suitable thiadiazole-containing dyes are described, for example, in International Patent Publication WO 2007/103250, which is hereby incorporated by reference.

The amount of optical dye present in the composition is, for example, at least sufficient to result in the effective administration and/or evaluation of the tissue sealant or vascular closure device, for example, for the clinical evaluation of the repair of wounded biological tissue. In general, the relative amounts of optical dye comprised in the compositions can differ depending on, for example, the age, sex, weight, diet, or general health of the patient, and/or the characteristics (e.g., size, severity, location, etc.) of the wound. In an embodiment the ratio of the mass of the optical dye component to the mass of the adhesive material or plug component is selected from the range of 0.0001 to 10000, optionally for some applications selected from the range of 0.001 to 1000, optionally for some applications selected from the range of 0.01 to 100.

The minimum amount of optical dye that enables detection of seal formation can vary from dye to dye and/or from patient to patient. Suitable amounts, therefore, may be determined by experimentation within the ambit of one skilled in the art, such as an appropriate medical professional. Where the optical dye is a commercially available biocompatible contrast or imaging agent, for example, it may be used as directed. The amount and type of optical dye will preferably comply with Food and Drug Administration (or other regulatory agency) regulations.

Connecting Group

In some embodiments, the compositions of the invention further comprise a connecting group. Generally speaking, the connecting group is capable of conjugating (i.e., linking or bonding) the adhesive material or plug to the optical dye. The connecting group may be independently attached to the adhesive material or plug device and the optical dye by way of covalent bonds or by way of a non-covalent interaction such as hydrogen bonding, ionic bonding, Van der Waals forces, hydrophobic interactions, and the like. In an embodiment, the connecting group is attached to the adhesive material or plug and the optical dye by way of covalent bonds. Useful connecting groups include, but are not limited to, natural or synthetic polymers and biopolymers, such as polypetides, polyoligonucleotides, polynucleotides, collagen, synthetic forms of collagen, and polysaccharides. Useful connecting groups also include a range of hydrocarbon and substituted hydrocarbon connecting groups such as unsubstituted or substituted alkylenes, cycloalkylenes, alkenylenes, cycloalkenylenes, and alkynylenes. In various embodiments, the connecting group is a bidentate ligand, a tridentate ligand, a tetradentate ligand, a pentadentate ligand, or a hexadentate ligand; more preferably in these embodiments. Alternatively, combinations of bidentate ligands, tridentate ligands, tetradentate ligands, pentadentate ligands, and hexadentate ligands may be employed. Multifunctional (e.g., tridentate, tetradentate, etc.) moieties may be linked by more than one functionality at either the adhesive material or plug or a component thereof and the optical dye, provided at least one functionality is attached to the adhesive material or plug or a component thereof and another functionality is attached to an optical dye molecule.

In some embodiments, connecting groups comprise those derived from polymers such as, for instance, polyalkylene glycol, a poly(ethylene glycol), a polyurethane, a polyamine, a succinimide-derivatized poly(ethylene glycol), a thiol-derivatized poly(ethylene glycol), an polyisocyanate, a polycyanoacrylate, a polyacrylate, a polyamine, a polyalkylene oxide, a polyglycerol, or a polyamide, combinations thereof, and the like.

Other connecting groups comprise, but are not limited to, for instance, nitrogen-containing compounds, such as diamines (e.g., dimethylaminoethylamine (DMAEA), ethylaminoethylamine (EAEA), diethylaminoethylamine (DEAEA), N,N-diisopropylaminoethylamine (DIPAEA), tetramethylethylenediamine (TMEDA), 1,2-diaminopropane (12DAP), 1,3-diaminopropane (13DAP), methylaminopropylamine (MAPA), diemethylaminopropylamine (DMAPA), diethylaminopropylamine (DEAPA), dibutylaminopropylamine (DBAPA), tetramethyl-1,3-diaminopropane (TMDAP), 2-hydroxyethylaminopropylamine (HEAPA), 1,4-diaminobutane (14DAB), N,N,N',N'-tetramethythexamethylenediamine (TMHMDA), N,N'-di-tert-butylethylenediamine (DTBEDA), N-aminopropylmorpholine (NAPM), N-methylmorpholine (NMMOL)), polyamines (e.g., imino-bis-propylamine (1BPA), methylamino-bis-propylamine (MIBPA), pentamethyldiethylenetriamine (PMDETA), amino acids (e.g., a peptide comprising the sequence -(-Pro-Hyp-Gly-)$_x$- wherein X is one or greater), and combinations thereof. In some embodiments, the connecting group is a collagen mimetic peptide (CMP). Collagen mimetic peptides are peptides, typically of less than 30 amino acids, composed of multimers of known helicogenic peptide trimers.

Additional Components

In addition to the adhesive material, plug, the optical dye, and the connecting group (if present), the compositions of the invention may further comprise one or more growth factors known to assist in wound healing. Representative growth factors that may be present in the compositions comprise, for example, angiogenin(s); bone morphogenic proteins (BMPs) (e.g., BMP-1, BMP-2); endothelin(s); epidermal growth factors (EGFs); fibroblast growth factors (FGFs) (e.g., FGF-1, FGF-2, FGF-3, FGF-4, and so on); Granulocyte-Monocyte Colony Stimulating Factor (GM-CSF); heparin-binding growth factor-1 (HBGF-1); heparin-binding growth factor-2 (HBGF-2); hepatocyte growth factors; insulin-binding growth factors (IGFs) (e.g., IGF-1, IGF-2); interferons (e.g., INF-$\alpha$, INF-$\beta$, and INF-$\Delta$); interleukins (e.g., IL-1, IL-2, IL-6, and IL-8); Keratinocyte Growth Factor-2 (KGF-2); osteoid inducing factor (IOF); osteogenic protein 1 (OP-1); cartilage-inducing factors (CIFs) (e.g., CIF-A, CIF-B); platelet-derived growth factors (PDGFs) (e.g., PDGF-bb); platelet factor-4 (PF-4); transforming growth factor-$\alpha$; transforming growth factor-$\beta$; transforming growth factor-$\gamma$; tumor necrosis factor (TNF); and combinations thereof. See, e.g., Growth Factors and Other Aspects of Wound Healing: Biological and Clinical Applications, Alan R. Liss, Inc. New York, N.Y., 303-29 (1988). The growth factor(s) may be supplied endogenously from body fluids, such as those in wounded biological tissue, prepared using molecular techniques and comprised in the compositions, or purchased from a variety of commercial sources and comprised in the compositions. Where the growth factor(s) is supplied exogenously (e.g., by way of a recombinant polypeptide growth factor added to the composition), the selection of the particular growth factor(s) may depend on the desired application and can be readily determined by those skilled in the art.

The concentration(s) of the above-noted additional pharmaceutically active components or agents comprised in the compositions of the invention can vary depending on the desired objective, and should be sufficient to accomplish the particular purpose for which they are used. In addition, more than one pharmaceutically active component or agent may be comprised in the composition to be released simultaneously or substantially simultaneously, or released in a predetermined time-released manner. The amount of each component can be readily determined by those skilled in the art, for example, by empirically testing various concentrations and selecting that which is effective for the intended purpose and the site of application, or by consulting dosage information provided with commercially available forms of such drugs.

In general, the relative amounts of additional pharmaceutically active components or agents comprised in the compositions can differ depending on, for example, activity of the specific component(s) employed; the age, weight, sex, diet, or general health of the patient; and/or the relative severity of the wound or other disease, pathological disorder, and medical condition to be treated or prevented. The minimum concentration of additional pharmaceutically active components having a desired degree of efficacy can vary from drug to drug and/or from patient to patient. Suitable concentrations, therefore, may be determined by experimentation within the ambit of one skilled in the art, such as an appropriate medical professional. The amount and type of additional pharmaceutically active components that may be comprised in the compositions of the invention will preferably comply with Food and Drug Administration (or other regulatory agency) regulations.

In addition to the components discussed above, the compositions of the invention may comprise any number of other inhibiting agents (e.g., agents that can inhibit the activities of the tissue sealant and components thereof and/or the optical dye that may interfere with any of the biological activities of the other components, such as the growth factor(s) and the pharmaceutically active agent(s), or vice versa), potentiating agents (e.g., agents that can potentiate, mediate, or enhance any of the biological activities of the tissue sealant and components thereof, the optical dye, the growth factor(s), and/or the additional pharmaceutically active agent(s)), agents that inhibit the breakdown of the resulting seal or clot (e.g., antifibrinolysis agents such as aprotinin, epsilon-aminocaproic acid (EACA), tranexamic acid (TXA, AMCA), and the like), and combinations thereof.

Synthesis of Compositions for Tissue Sealants and Closure Device

As will be understood by those of skill in the art, a range of approaches may be used for making the present tissue sealants and vascular closure devices. Linking of the optical dye and adhesive material components and the optical dye and vascular plug components can be achieve using a variety of connecting groups and synthetic pathways. Linking or otherwise incorporating the optical dye with an adhesive material or vascular plug may be achieved using a polymer connecting group, for example using a branched block copolymer having a cationic polymer block that bonds with the optical dye. For example, similar methods for preparing bioconjugates using cationic branched polymers, such a 1,2,4,5-tetrakis(N,N-diethyldithiocarbamyl(poly(N-[3-(dimethylamino)propyl]acrlamide-block-poly(N-isopropylacrylamide))benzene copolymers, are known in the art. [See, e.g., Yasuhide Nakayama et al., Langmuir 2007, 23, 8206-8211]. Other synthetic strategies for linking or otherwise incorporating the optical dye with an adhesive material or vascular plug include conjugation using a dendrimer tether or use of an organosilane linker, carbonyldiimidazole linker, glycidoxypropyltrimethoxysilane linker, or aminopropyltrimethoxysilane linker. For example, similar methods for conjugating DNA onto silicon substrates are well developed. [See, e.g., Goddard and Erikson, Anal Bioanal Chem, 2009; DOI 10.1007/s00216-009-2731-γ]. Other synthetic strategies for linking or otherwise incorporating the optical dye with an adhesive material or vascular plug include polymerization and cross linking reactions, such as heterogeneous free radical and controlled/living radical polymerization reactions. Such polymerization reactions may link the optical dye at terminus sites of polymer components of the sealant or vascular plug or may incorporate the optical dye within cross linking sites of a polymer network component of a sealant or vascular plug. For example, similar methods for making and functionalizing hydrogels via polymerization and cross linking reactions, such as carbodiimide coupling, Michael addition and free radical polymerization reactions, are well known. [See, e.g., Oh et al., Prog. Polym. Sci., 33, (2008) 448-477].

Linking may be achieved in some embodiments using an optical dye, adhesive materials or vascular plug having an amine group, for example, may be achieved by techniques involving succinimido active esters. In an embodiment, for example, a carboxyl group of a dye is activated by making a mixed anhydride in situ with isobutylchloroformate, and the activated dye compound is subsequently reacted with an adhesive material or a plug having a pendant an amino group, to achieve linking of the dye and adhesive or plug components. Alternatively, a carboxyl group of the dye may be first esterified with N-hydroxysuccinimide, and subsequently reacted with the amino group of an adhesive material or plug, to form an amide bond linking the of the dye and adhesive or plug components. Alternatively, a carboxyl group of an adhesive material or plug is activated by making a mixed anhydride in situ with isobutylchloroformate, and the activated dye compound is subsequently reacted with an optical dye having a pendant an amino group, to achieve finking of the dye and adhesive or plug components. Alternatively, a carboxyl group of the adhesive or plug may be first esterified with N-hydroxysuccinimide, and subsequently reacted with the amino group of the optical dye, to form an amide bond linking the of the dye and adhesive or plug components.

The invention includes tissue sealants wherein the optical dye is non-covalently associated with the adhesive material or vascular plug. As used herein, "noncovalently associated" refers to a mixture of one or more optical dyes that are provided with, but not covalently bonded to, the adhesive material or closure device. In some embodiments, for example, noncovalently associated optical dye(s) and an adhesive material or closure device participate in stabilizing interactions, such as associative interactions. In some embodiments, for example, noncovalently associated optical dye(s) and/or adhesive material or closure device participate in stabilizing electrostatic interactions, hydrogen bonding, dipole-dipole interactions and/or van der Waals interactions. In some embodiments, for example, the optical dye is mixed with, dispersed into, or otherwise physically integrated with the adhesive material or vascular plug. Mixtures of optical agents and adhesive materials or vascular plugs include heterogeneous and homogeneous mixtures, colloids, emulsions including micro- and nano-emulsions, sols, gels, and other dispersions. Tissue sealants of this aspect may further include one or more stabilizing agents such as a surfactant, to facilitate mixing, dispersion and/or integration the optical dye with the adhesive material or vascular plug.

Salts and Prodrugs

As noted above, the pharmaceutically active agents and components may be in their salt form. Where particular salt forms are already described for a particular pharmaceutically active agent, other salt forms are also contemplated. Typically, the salt will be a pharmaceutically acceptable salt; that is, a salt prepared from pharmaceutically acceptable non-toxic acids, including inorganic acids and organic acids. Suitable non-toxic acids comprise inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric , p-toluenesulfonic acid, and combinations thereof; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N"-dibenzylethylenediamine, chloroprocaine, diethanolamine, procaine, n-benzylphenethylamine, diethylamine, piperazine, tris(hydroxymethyl)-aminomethane, tetramethylammonium hydroxide, and combinations thereof. Pharmaceutically acceptable salts of any of the components described herein may be prepared by reacting the free acid or base forms of these components with a stoichiometric amount of the appropriate base or acid in water or in an organic solvent, or in a mixture of the two. Some may prefer to use nonaqueous media like ether, ethyl acetate, ethanol, isopropanol, or acetonitrile. Examples of other salts are found in Remington's Pharmaceutical Sciences (A. Gennaro, ed., 19th ed.) (Mack Publishing, Easton, Pa., 1995).

Since prodrugs are known to enhance the solubility, bioavailability or manufacturing of pharmaceuticals, the pharmaceutically active component(s) may be delivered in prodrug form. Prodrugs generally comprise any covalently bonded carriers that release an active parent drug in vivo when such prodrug is administered to a mammalian subject. Prodrugs may be prepared by modifying functional groups present in the compound in such a way that the modifications are cleaved, either in routine manipulation or in vivo, from the parent compound. Prodrugs comprise pharmaceutically active component(s) described above wherein a hydroxyl or amino group is bonded to any group that, when the prodrug is administered to a mammalian subject, cleaves to form a free hydroxyl or free amino group, respectively. Examples of prodrugs comprise, but are not limited to, acetate, formate, and benzoate derivatives of alcohol and amine functional groups in the pharmaceutically active components) described above. Prodrugs may refer to compounds that are rapidly transformed in vivo to yield the drugs, for example by hydrolysis in blood. A thorough discussion of prodrugs is provided in the following: Design of Prodrugs, H. Bundgaard, ed., Elsevier, 1985; Methods in Enzymology, K. Widder et al., eds., Academic Press, 42, p. 309-396, 25 1985; A Textbook of Drug Design and Development, Krogsgaard-Larsen and H. Bundgaard, eds., Chapter 5; "Design and Applications of Prodrugs" p. 113-191, 1991; Advanced Drug Delivery Reviews, H. Bundgaard, 8, p. 1-38, 1992; Journal of Pharmaceutical Sciences, 77, p. 285, 30 1988; Chem. Pharm. Bull., N. Nakeya et al., 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987.

Pharmaceutical Compositions

The compositions of the invention may be formulated in a medium that may optionally comprise one or more antioxidants, buffers, carriers, osmotic agents, pH modifiers, preservatives, surfactants, viscosifiers, and other substances that may be desired or advantageous to assure biocompatibility, efficacy or other desirable characteristics, or to prepare a particular dosage form.

For instance, the compositions may comprise a pharmaceutically acceptable carrier. The carrier, also known in the art as an excipient, vehicle, auxiliary, adjuvant, or diluent, may be a substance that is pharmaceutically inert, confers a desirable consistency or form to the composition, and does not diminish the efficacy of the composition. The carrier is generally considered to be pharmaceutically or pharmacologically acceptable if it does not produce an unacceptably adverse, allergic, or other untoward reaction when administered to a mammal, especially a human.

Pharmaceutically acceptable carriers for use in combination with the compositions of the invention are well known to those of ordinary skill in the art and may be selected based upon a number of factors: the particular tissue sealant, closure device, adhesive material, plug, optical dye, or other components used, and their concentration; stability or intended bioavailability; the subject, its age, size and general condition; and the route of administration. Nonaqueous, pharmaceutically-acceptable polar solvents comprise, but are not limited to, alcohols (e.g., α-glycerol formal, β-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, ooly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$ to $C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, nadecane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; sorbitan monooleate; and combinations thereof.

Other pharmaceutically acceptable solvents for use in the invention are well known to those of ordinary skill in the art, and are identified in The Chemotherapy Source Book (Williams & Wilkens Publishing); The Handbook of Pharmaceutical Excipients, (American Pharmaceutical Association, Washington, D.C., and The Pharmaceutical Society of Great Britain, London, England, 1968); Modern Pharmaceutics, (G. Banker et al., eds., 3d ed.) (Marcel Dekker. Inc., New York, N.Y., 1995); The Pharmacological Basis of Therapeutics, (Goodman & Gilman, McGraw Hill Publishing); Pharmaceutical Dosage Forms, (H. Lieberman et al., eds.) (Marcel Dekker, Inc., New York, N.Y., 1980); Remington's Pharmaceutical Sciences (A. Gennaro, ed., 19th ed.) (Mack Publishing, Easton, Pa., 1995); The United States Pharmacopeia 24, The National Formulary 19, (National Publishing, Philadelphia, Pa., 2000), A. J. Spiegel et al.; and Use of Nonaqueous Solvents in Parenteral Products, Journal of Pharmaceutical Sciences, Vol. 52, No, 10, 917-927, (1963).

It will be understood that with the inclusion of these and other excipients, formulations containing the compositions of the invention may take the form of solid, semi-solid, lyophilized powder, or liquid dosage forms such as, for instance, aerosols, bandages, creams, dressings, emulsions, foams, gels/jellies, lotions, ointments, pastes, patches, powders, soaps, solutions, sprays, suppositories, suspensions, sustained-release formulations, tinctures, and the like, for example, in unit dosage forms suitable for simple administration.

As noted above, the compositions of the invention may also be formulated in a medium including one or more antioxidants, osmotic agents, pH modifiers, preservatives, or surfactants. Examples of antioxidants comprise, but are not limited to, ascorbic acid, BHA (butylated hydroxyanisole), BHT (butylated hydroxytoluene), vitamin E, vitamin E PEG 1000 succinate, and combinations thereof. Examples of osmotic agents comprise, but are not limited to, glucose, glycerol, sodium chloride, and combinations thereof. Examples of pH modifiers comprise, but are not limited to, acetic acid, boric acid, hydrochloric acid, sodium acetate, sodium bisulfate, sodium borate, sodium carbonate, sodium citrate, sodium hydroxide, sodium nitrate, sodium phosphate, sodium sulfite, sulfuric acid, and combinations thereof. Examples of preservatives comprise, but are not limited to, benzalkonium chloride, chlorobutanol, ethylenediamine tetraacetic acid (EDTA) and salts thereof, methylparaben, polyquad, propylparaben, sorbate, thimerosal, and combinations thereof. Examples of surfactants comprise pharmaceutically acceptable anionic, cationic, nonionic, and zwitterionic surfactants including, but not limited to, benzalkonium chloride, phospholipids, polyoxyethylated castor oil, sorbitan esters (such as polysorbate 80 (e.g., Tween™ 80 or Crillet 4 HP™), polysorbate 60, polysorbate 40 and polysorbate 20), tocopherol PEG succinate, and combinations thereof.

Uses of the Compositions of the Invention

The compositions and methods described herein may be used in a variety of applications, such as in vitro laboratory applications, ex vivo tissue treatments, and in vivo tissue treatments, including in vivo surgical and post-operative procedures and non-surgical procedures on living organisms (e.g., humans and other mammals).

Another aspect of the invention is directed to methods for the treatment of wounded biological tissue and clinical evaluation of such treatment. The methods generally involve applying a composition to a wounded biological tissue of a subject in need of such treatment, forming a seal upon the wounded biological tissue upon or after activation of the adhesive material or at least partial occlusion of a vasculature opening by the plug, and detecting formation of the seal when an optical condition of the optical dye changes in response to the activation of the adhesive material or at least partial occlusion of a vasculature opening by the plug. The compositions for use in the methods of the invention may comprise a tissue sealant or closure device as described in detail throughout the present description.

Generally, the compositions of the invention may be used in the treatment of wounded biological tissue, for instance, as a treatment to inhibit or stop the bleeding or fluid loss from wounds or damage due to trauma or surgery. Wounded biological tissue may comprise any damaged tissue in a living organism and may also comprise the tissue surrounding the damaged tissue. The compositions may be used in relatively large surface area applications, in relatively small surface area applications (e.g., where precise hemostatic treatment is desired), and/or where other methods of achieving hemostasis such as sutures, staples, or manual compression is inconvenient or undesirable. Alternatively, the compositions and methods of the invention may be used in combination with conventional methods of achieving hemostasis such as sutures, staples or manual compression.

The damage or wound to the biological tissue may have been caused by any agent including, but not limited to, traumatic injury, infection, or surgical intervention. For instance, the compositions described herein may be used to inhibit or stop bleeding or fluid loss during or after surgery including abdominal surgery, brain surgery, cardiovascular surgery, dental surgery, gastrointestinal surgery, gynecological surgery, neurosurgery, orthopedic surgery, plastic surgery, prosthetic surgery, reconstructive surgery, tissue transplant surgery, thyroidal surgery, urological surgery, and vascular surgery. Additionally or alternatively, the compositions described herein may be used to inhibit or stop bleeding or fluid loss resulting from minor and major topical wounds such as abrasions, burns, contusions, cuts, drying, irritations, lacerations, scrapes, and sores, as well as broken bones, trauma to the dura mater (including, for example, leakage of cerebrospinal fluid), and ulcers.

in addition to accidental or purposeful traumatic injury, the wounded tissue may result from surgical procedures such as anastamosis (including, for example, stenosis or the treatment of blocked or narrowed blood vessels by anastamosis), surgical or other incisions including internal and epidermal incisions, biopsies, penetrations, catheterizations, angiograms, endoscopic procedures, laproscopic procedures, excisions, manipulations, suturing, percutaneous arterial puncture, skin or tissue grafting, curettage, combinations thereof, and the like.

The biological tissue may be of any type where wound closure and hemostasis is desirable, including, for example, cardiovascular tissue, connective tissue, dermatological tissue, gastrointestinal tissue, genital tissue, gynecological tissue, musculoskeletal tissue, neurological tissue, ocular tissue, oral tissue, otolaryngological tissue, renal tissue, respiratory tissue, urological tissue, and tubular tissues including arteries, veins, capillaries, lymphatics, vessels, microvessels, any anatomical tubes such as the ducts (e.g., pancreatic, liver, cystic, tear, prostatic, bile, etc.) and the ureters, urethra, epididymis, vas deferens, fallopian tubes, bowel, and bronchi and other gastrointestinal, respiratory, body, and brain ducts and tubes. Combinations of the above tissue types are also contemplated. Thus, for example, the wounded biological tissue may comprise normal, infected, or cancerous arterial, axonal, blood vessel, bone, brain, cartilaginous, cervix, colonic, corneal, embryonic, endometrial, esophageal, fascia, heart, intestinal (including small and large intestine), kidney, liver, lung, muscular, neuronal, ovarian, pancreatic, prostatic, skin (including the epidermal, dermal, and subcutaneous fat layers), splenic, stomach, testicular tissues, and combinations thereof, as well as relatively healthy tissue surrounding such wounded biological tissue.

Application of the Composition

In general, the above-described compositions are applied directly on the wounded biological tissue and, as noted above, may also be applied to the surrounding tissue. Typically, for external wounds the composition can be applied directly by any method including brushing, injecting, painting, pouring, or spraying the composition on the wound. Alternatively, the composition may be contained in a bandage or other dressing that is applied to the wounded biological tissue, provided that the bandage or dressing material does not affect the optical condition of the optical dye and the detection thereof. For internal wounds, such as during or after surgical procedures, similar methods may be used in the application of the composition. Alternatively, the compositions of the present invention may be provided in a plug form or vasculature closure device form, for example for use in occluding a vasculature opening.

Additionally or alternatively, any one of several known devices for applying tissue sealant or closure device materials to punctures or incisions in biological tissue (e.g., arterial tissue) may be employed. Selection of a particular device may depend on the severity or location of the wounded biological tissue, and is within the knowledge of skilled medical professionals. A variety of devices for the application of tissue sealant materials are known, some of which are described, for example, in U.S. Pat. Nos. 4,852,568 and 4,890,612 to Kensey; U.S. Pat. No. 5,342,393 to Stack; U.S. Pat. No. 5,370,660 to Weinstein et al; U.S. Pat. No. 5,411,520 to Nash et al.; and U.S. Pat. No. 6,325,789 to Janzen et al.

Where known tissue sealant or closure device materials are employed (e.g., commercially available tissue sealants) and combined with the optical dye(s) described above, they may be applied as directed.

The amount of the composition that is applied to the wounded biological tissue and the physical form (including size) of the resulting seal upon the wounded biological tissue may vary depending on the particular treatment for which the composition is employed. Among the various factors contributing to the amount of the composition initially applied to the wounded biological tissue and the form and size of the resulting seal are the severity of the wounded biological tissue, the location of the wound, and/or direct and indirect interaction(s) of other medications present in the circulatory system of the patient (e.g., anticoagulants (such as heparin, warfarin, etc.) and vasodilators (such as hydralazine, isosorbide dinitrate, minoxidil, nesiritide, nitrates, etc.)). For instance, for deeper external wounds and/or wounds having a larger surface area, a greater amount of the composition will typically be employed as compared to relatively minor or superficial wounds or wounds having a relatively small surface area such as wounds to arterial tissue. Generally, a sufficient amount of the composition is applied to the wounded biological tissue to withstand pressurized blood flow before, during, and after seal formation.

Activation and Seal Formation

The speed at which the seal or clot forms may be to some degree dictated by the particular application for which the composition is employed. For example, relatively rapid setting may occur for arterial wound or hemorrhaging tissue damage, while slower setting may occur for wounds to bony tissue or relatively superficial wounds. In some embodiments, it may be preferred that the tissue sealant or vascular closure device activates and the seal at least partially forms and may be detected within seconds, minutes or hours after application. For example, the formation and detection may occur within about 0 to about 90 minutes, within about 0 to about 60 minutes, within about 0 to about 20 minutes, or within about 0 to about 1 minute.

As noted above, the tissue sealant or vascular closure device may be activated by the natural blood coagulation cascade and the components thereof, by reaction between the various components of the tissue sealant, and/or by reaction with other agents in the subject being treated. In some embodiments, the tissue sealant or vascular closure device may be activated by the interaction of its components with the endogenous substances present in the bodily fluids of the patient; that is, the tissue sealant or vascular closure device is activated by the coagulation cascade and the various factors and components involved therewith. Generally, this activation occurs spontaneously or substantially spontaneously upon application, forming the seal in a relatively short period of time.

For instance, in some embodiments, the tissue sealant or vascular closure device may be activated by one or more coagulation activators comprised in the composition or endogenously provided by the subject being treated including, for instance, those selected to activate the intrinsic, extrinsic or common pathways of the coagulation cascade. See FIG. 1. Thus, for example, activation through the intrinsic system may be accomplished with an APTT reagent containing a suitable contact activator, or with the separate addition of a contact activator. Suitable activators of the intrinsic pathway comprise, for example, phospholipids and contact activators. As contact activators, ellagic acid, collagen or collagen related substances, or various forms of silica (kaolin, micronized silica, colloidal silica) may be used. Alternatively, rather than using a contact activator, factor XIIa, factor XIa, or factor IXa may be used in combination with phospholipids as activators of the intrinsic pathway, each of which may be obtained or derived from human or non-human sources, produced by molecular techniques, or endogenously provided by the subject being treated. Optionally, components such as prothrombin, factor VIII/factor VIIIa and factor X may be used to activate the tissue sealant, each of which may be obtained or derived from human or non-human sources, produced by molecular techniques, or endogenously provided by the subject being treated. Photometric substrates selective for factor Xa or thrombin may also be used. See FIG. 1.

Activation by way of the extrinsic system may be accomplished by various tissue factors, with or without the addition of factor VII/factor VIIa. The tissue factor may be obtained or derived from human or non-human sources, produced by molecular techniques, or endogenously provided by the subject being treated. Alternatively, activation may be accomplished by factor VIIa in combination with phospholipids. Optionally, reagents such as prothrombin, factor V/Va, factor IX, and factor X may be used to activate the tissue sealant, each of which may be obtained or derived from human or non-human sources, produced by molecular techniques, or endogenously provided by the subject being treated. Photometric substrates selective for factor Xa or thrombin may also be used. See FIG. 1.

Activation by way of the common pathway may be accomplished by factor Xa, or factor X in combination with an endogenous or exogenous activator of factor X, such as a snake venom enzyme (e.g., snake venom enzyme from Russelli Viperii). For instance, the exogenous activator of factor X may be comprised in the composition for activation of endogenous factor X. Additionally or alternatively, prothrombin and/or factor VNa may be used to activate the tissue sealant, each of which may be obtained or derived from human or non-human sources, produced by molecular techniques, or endogenously provided by the subject being treated. Photometric substrates selective for thrombin may also be used. See FIG. 1.

In some cases the tissue sealant and/or vasculature closure device may be activated with energy, such as thermal energy and/or photons. In these cases, activation with thermal energy or photons may initiate or accelerate the curing and seal formation of the tissue sealant and/or vasculature closure device. The thermal energy or photons may be capable of activating the tissue sealant and/or vasculature closure device and components thereof in such a manner that produces the desired sealing characteristics, including the ability to detect seal formation as described herein.

Where thermal energy or photons are employed in the activation of the tissue sealant and/or vasculature closure device, the energy typically has a wavelength in the electromagnetic spectrum, and may be selected from X-rays, ultraviolet light, visible light, infrared light, and radiowaves. Thermal energy delivered through direct contact, for example, with a probe heated through electricity such as an electrocautery, or a probe heated through gas compression in the tip, or the passage of heated gas or liquid through the tip, may be used. Sound energy in the ultrasonic frequency or radiowaves in the microwave range may be additionally or alternatively employed. The energy can be delivered in a continuous or non-continuous fashion, and in a narrow or broad band of electromagnetic wavelengths. Examples of photon sources comprise monochromatic and polychromatic light, coherent or noncoherent light, delivered in a continuous or noncontinuous fashion. Examples of noncontinuous energy and/or photon delivery comprise single and/or multiple pulse train delivery. Photons may be delivered in a polarized or nonpolarized fashion, direct or reflected, with or without internal interference.

For instance, lasers may be employed in the activation of the tissue sealant and/or vasculature closure device including, but not limited to, those in the ultraviolet, visible, or infrared ranges such as the THC:YAG (2150 µm), Nd:YAG (1064 1320 nm), KTP (532 µm), Dye (577, 590, 610 nm), Krypton (647 nm), Argon (488 and 514 nm), carbon dioxide (10,600 nm), diode (810 nm), and excimer (192, 222, 249, 308, 351 nm) lasers.

Generally speaking, very little if any pressure needs to be applied to the wounded biological tissue following application of a composition of the invention. Activation of the various tissue sealant and/or vasculature closure device components in the composition and/or the endogenous substances present in the bodily fluids of the patient and the particular formulation conditions are generally sufficient to hold the composition against the wounded biological tissue and surrounding tissue. Other conventional methods for achieving hemostasis (such as sutures, staples, or manual compression), however, may be used in combination with the compositions and methods of the invention if desired.

Defection

As noted above, the optical condition of the optical dye changes in response to the activation or state of the tissue sealant and/or vasculature closure device and corresponding seal and/or clot formation. Accordingly, the change in optical condition may correlate to the formation and/or maintenance of a tissue seal or occlusion. Thus, detection of the formation of the seal involves observation of the optical condition change.

The detectable optical condition may be, for example, an observable change in absorbance, reflectance, phosphorescence, chemiluminescence, scattering, optoacoustic property or other spectral property. Depending on the particular optical dye, adhesive material and components thereof, connecting group, and/or other components present in the composition, the detectable optical condition change may occur, e.g., instantaneously or substantially instantaneously upon initial adhesive material activation, instantaneously or substantially instantaneously upon achieving hemostasis (i.e., substantial seal formation), or may gradually change from initial activation of the adhesive material throughout seal formation until hemostasis is achieved. In the latter situation, for example, the presence of the seal upon the wounded biological tissue (e.g., 10%, 20%, 30%, 40%, 50%, 60%, 70%, 80%, 90%, 95%, 99.99%, or more, by area) can be correlated to a particular wavelength or other spectral property as seal formation occurs. Alternatively, a relatively immediate or instantaneous optical condition change can indicate adhesive material activation and/or substantial seal formation in an "on/off" fashion. Thus, through the use of the above-described compositions, medical professionals can accurately detect and monitor seal or clot formation in real-time and determine when hemostasis of wounded biological tissue has been achieved in a patient.

By way of example, the optical condition of the optical dye can be a particular wavelength corresponding to a color (e.g., blue) prior to tissue sealant and/or vasculature closure device activation and a different wavelength corresponding to a color (e.g., yellow) upon or after activation of the tissue sealant and/or vasculature closure device. Thus, the color change indicates that tissue activation and seal formation is occurring or has occurred. Alternatively, the optical condition may be non-colored or non-fluorescent prior to activation and colored or fluorescent upon or after activation of the tissue sealant and/or vasculature closure device, and vice versa. Thus, the presence (or absence) of color or fluorescence indicates that seal formation is occurring or has occurred. Although wavelengths corresponding to any color may be employed, red is generally less preferred due to the typical color of the field (i.e., the wounded biological tissue).

In general, conventional methods may be used to detect the optical condition change, including instrumental methods and visual readings or observation (i.e., simple visual examination without instrumentation) For some applications it may be preferred that the optical condition change is detectable by the human visual system (e.g., by a human observer, such as a medical professional); that is, the optical change resulting from the activation of the tissue sealant and/or vasculature closure device and the partial or substantial formation of a seal or clot upon the wounded biological tissue is readily and easily observable visually by the eye. Additionally or alternatively, the detection of the optical condition change may be carried out instrumentally using, for example, magnetic resonance imaging, CCD cameras, film, or through the use of other scanning devices, fluorometers, photodiodes, quantum counters, optical microscopes (e.g., a confocal microscope), epifluorescence microscopes, scanning microscopes, spectrometers (e.g., a luminescence spectrometer), spectrophotometers, spectrocolorimeters, Raman spectrometer, single-photon-counting detectors (e.g., PMT or APD), or other light sensitive sensor, or by signal amplifying devices such as photomultiplier tubes. Although instrumental methods may provide better quantitation, such methods may lack convenience in the field or may be expensive in terms of the equipment and materials needed to carry out the detection. Accordingly, simple visual examination may be preferred in some applications of the invention.

Additionally, the detection method may be combined with one or more optical filters or filter sets in order to improve signal to noise ratio (e.g., where detection is performed by a fluorescence signal emission). Background light may be minimized using cut off filters or bandpass filters between the field and the visual or instrumental detection means and/or by using opaque shielding to remove any ambient light from the field.

Regardless of the detection method employed (e.g., by a human observer or instrumentally), readings or observations may be taken continuously or approximately once every 5, 10, 15, 20, 25, 30, 35, 40, 45, 50, 55, or 60 seconds; once every few minutes (e.g., 2, 3, 4, 5, 6, 7, 8, 9, 10, 15, or 20 minutes); once every half hour, once every hour, once every two hours, once every three hours, or longer; to determine whether or not a seal has formed upon the wounded biological tissue and hemostasis achieved. Further monitoring of the sealed tissue may also take place following hemostasis to ensure that the seal remains substantially in place for the desired period of time.

To visually assess, quantitatively or semi-quantitatively, the activation of the tissue sealant and the absence, partial presence, or presence of a seal upon the wounded biological tissue, the optical condition of the optical dye before or upon or after activation of the tissue sealant and/or vasculature closure device may be compared with predetermined standard reference data that corresponds to the degree of tissue sealant and/or vasculature closure device activation and seal formation. The standard reference data may be stored in an instrument against which the instrument compares readings taken from the optical condition of the optical dye, or the standard reference data may be presented as a standard reference chart that may be used by a human observer (described in further detail below).

Kits

In an aspect, the invention is directed to a medical treatment kit. This kit comprises an optical dye and an adhesive material that is capable of forming a seal at least when contacted with biological tissue. In a specific embodiment, the kit further comprises instructions directing a user to apply the adhesive material and the optical dye to biological tissue of a patient The instructions also direct a user to monitor an optical condition of the optical dye, because a change in the optical condition dye tends to be indicative of a change in a state of the tissue sealant. In an embodiment, a medical treatment kit of the present invention further comprises other items useful to assist in monitoring of the tissue sealant, for example a color chart or graph, sealant application devices or compositions, sealant preparation devices or compositions, and excitation and/or emission optical filters. In an embodiment, a kit of the present invention comprises a chart for visual comparison of an optical condition to one or more known reference standards. In a specific embodiment, at least one of the known reference standards corresponds to the optical condition of the optical dye prior to activation of the tissue sealant or the optical condition of the optical dye upon or after activation of the tissue sealant.

Such kits can be used in both laboratory and clinical applications. The kits comprise one or more of the tissue sealants and/or vasculature closure device described above, one or more of the optical dyes described above, and may optionally comprise one or more of the additional components discussed above (e.g., growth factors, pharmaceutically active agents, etc.). Each kit component (e.g., the tissue sealant and/or vasculature closure device and the optical dye) may be provided in a separate, waterproof, sterile package, and mixed prior to use to form the above-described compositions, or the kits may comprise a single, ready-to-use container including the composition. The kits may also comprise instructions for the use of the kit, for example, in one or more of the methods for the treatment of wounded biological tissue and the detection of such treatment described herein.

Additionally, a kit designed for military, emergency, or even general clinical use may also comprise one or more instruments (e.g., disposable or re-usable, pre-sterilized or sterilizable instruments) such as scissors, scalpels, clamps, syringes, tourniquets, elastic or inelastic bandages or dressings, combinations thereof, and the like.

The kits may also comprise one or more devices or means for applying the compositions to the wounded biological tissue such as, for example, a syringe or syringe-like device, a dropper, a powder, an aerosol container, a spray bottle, a sponge applicator, or bandage material. The kit may also comprise one or more of the known devices for applying tissue sealant materials and/or vasculature closure devices to punctures or incisions in biological tissue discussed above.

In addition, the kit may comprise a chart for visual comparison of the optical condition of the optical dye to one or more known reference standards. As noted above, predetermined standard reference data can be employed in various detection methods to determine the degree of tissue sealant activation and/or seal formation, and such standard reference data may be presented on a standard reference chart. Additionally or alternatively, the kit may comprise the standard reference data complied on a disk or other media for use in an instrument for detection.

Typically, such charts comprise one or more reference areas (e.g., circles, squares, or other shapes) having an optical condition (e.g., a wavelength) that corresponds to a different or substantially different degree of tissue sealant and/or vasculature closure device activation and/or seal formation. The reference areas may be set against, and surrounded by, a white background or other colored background that enables users to more easily distinguish between relatively small differences in the optical condition of the optical dye and the reference areas on the chart.

The chart may be in the form of a piece of paper or other suitable substrate material (including, for example, the instructions and the inner and outer packaging of the kit) that is typically coated or printed with colored or fluorescent inks using conventional techniques such as silk screening or lithography, or other suitable substances can be used to form the background and the reference areas that are displayed or set against it. The chart may also be provided with an adhesive backing so that it may be adhered to a bottle or vial comprised in the kit or other container or packaging of the kit, or on some other surface.

The number and optical signals of the various reference areas comprised on the chart can vary considerably depending on the particular optical dye employed in the composition. Generally, the optical signals of the various reference areas will correlate with the known optical signals of the optical dye prior to and/or upon tissue sealant and/or vasculature closure device activation, or may correlate with the known optical signals of the optical dye during the gradual formation of the seal upon the wounded biological tissue. For example, the chart may comprise two reference areas, one reference area (e.g., color block) having an optical condition that generally matches the optical condition of the optical dye prior to activation of the tissue sealant, and the other reference area (e.g., color block) having a different optical condition that generally matches the optical condition of the optical dye upon or after activation of the tissue sealant and/or vasculature closure device. Alternatively, the chart may comprise three or more reference areas that form a scale, each reference area having a slightly different optical condition than the previous one, which matches the optical signals of the optical dye during the gradual activation and/or formation of the seal upon the wounded biological tissue.

Methods of Using

In another aspect, the present invention provides a method for treating biological tissue, the method comprising: (i) administering a therapeutically effective amount of a tissue sealant or vascular closure device to the biological tissue; and (ii) exposing the administered tissue sealant or vascular closure device to electromagnetic radiation. As will be understood by those of skill in the art, any of the tissue sealants or vascular closure devices described herein may be used in the present methods. In an embodiment, the method comprises contacting a biological tissue, such as vasculature tissue, with a therapeutically effective amount of a tissue sealant or vascular closure device. In an embodiment, the method comprises contacting a vasculature puncture, with a therapeutically effective amount of a tissue sealant or vascular closure device. In an embodiment, the method further comprises activating the tissue sealant or vascular closure device. In an embodiment, the method further comprises detecting a change in an optical property of an optical dye component of the administered tissue sealant or vascular closure device, for example, visually (e.g., using the eye) or via an optical imaging technique or optical detection technique. In an embodiment, the administered tissue sealant or vascular closure device is exposed to a diagnostically effective amount of electromagnetic radiation, preferably for some embodiments having wavelengths selected over the range of 350 to 1400. In some embodiments, the method comprises exposing the tissue sealant or vasculature closure device to electromagnetic radiation continuously for a period of time or at several time intervals, so as to detect and/or quantify the change in optical condition of the dye. In an embodiment, the administered tissue sealant or vasculature closure device is exposed to electromagnetic radiation having a first wavelength distribution; and the emitted radiation has a second wavelength distribution different from the first wavelength distribution; preferably, the emitted radiation is fluorescence. In an embodiment, a method of this aspect further comprises the step of monitoring the intensity or wavelength distribution of radiation emitted from the optical dye. Preferably, the emitted radiation has a first intensity when the vasculature opening is open and a second intensity that is higher than the first intensity when the vasculature opening is closed, or hemostasis is achieved, or when the plug or sealant is incorporated into a clot. In this way, it is possible to identify when the vasculature opening is closed by observation and/or monitoring the emitted radiation. In a specific embodiment, the fluorescence yield of the optical dye increases when the optical dye is immobilized, for example by 100 times or more. In another embodiment, the optical dye is immobilized when hemostasis is achieved. It may be preferred that the optical dye is bound to the plug, for example by a covalent bond or by means of a covalent linker. In a specific embodiment, the adhesive material or plug comprises an active clotting agent; preferably, the active clotting agent comprises collagen or thrombin.

Formulations

In an embodiment, the invention provides a pharmaceutical formulation comprising a composition of the invention. In an embodiment, the invention provides a method of synthesizing a composition of the invention or a pharmaceutical formulation thereof. In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention; 2007; and 2008, and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the present invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopelas (e.g. DAB, Ph. Eur., BP, NF, USP), as well as other excipients whose properties do not impair a physiological use.

In an embodiment, an effective amount of a composition of the invention can be a therapeutically effective amount. In an embodiment, an effective amount of a composition of the invention can be a diagnostically effective amount. In an embodiment, an active ingredient or other component is included in a therapeutically acceptable amount. In an embodiment, an active ingredient or other component is included in a diagnostically acceptable amount.

Variations on compositions including salts and ester forms of compounds: Compounds of this invention and compounds useful in the methods of this invention include those of the compounds and formula(s) described herein and pharmaceutically-acceptable salts and esters of those compounds. In embodiments, salts include any salts derived from the acids of the formulas herein which acceptable for use in human or veterinary applications. In embodiments, the term esters refers to hydrolyzable esters of compounds of the names and structural formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

In an embodiment, the invention provides a method for treating a medical condition comprising administering to a subject in need thereof, a therapeutically effective amount of a composition of the invention. In an embodiment, the invention provides a method for diagnosing or aiding in the diagnosis of a medical condition comprising administering to a subject in need thereof, a diagnostically effective amount of a composition of the invention.

In an embodiment, the invention provides a medicament which comprises a therapeutically effective amount of one or more compositions of the invention, such as one or more tissue sealant and/or closure device described herein. In an embodiment, the invention provides a medicament which comprises a diagnostically effective amount of one or more compositions of the invention. In an embodiment, the invention provides a method for making a medicament for treatment of a condition described herein, such as for facilitating homostasis (e.g., stopping bleeding), controlling bleeding, repairing wounded tissue, treatment of a vasculature opening, treatment of a vascular access site, and treatment of a vascular puncture. In an embodiment, the invention provides a method for making a medicament for diagnosis or aiding in the diagnosis of a condition described herein, such as for facilitating homostasis (e.g., stopping bleeding), controlling bleeding, repairing wounded tissue, treatment of a vasculature opening, treatment of a vascular access site, and treatment of a vascular puncture. In an embodiment, the invention provides the use of one or more compositions set forth herein for the making of a medicament.

Compounds of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds set forth herein.

In an embodiment, a composition of the invention is isolated or purified. In an embodiment, an isolated or purified compound may be at least partially isolated or purified as would be understood in the art.

The invention is further detailed in the following Examples, which are offered by way of illustration and are not intended to limit the scope of the invention in any manner.

EXAMPLE 1

Optically Functional Tissue Sealants and Vascular Closure Devices

Aspects of the present invention relate to the incorporation of optical dyes with vascular closure devices and tissue sealants, such as adhesive materials, collagen and thrombin plugs, etc., such that an increase or decrease in fluorescence or change in visual color or emission wavelength is achieved during, upon, or after hemostasis.

Over 7 million coronary angiograms and percutaneous coronary interventions (PCTs) are performed annually worldwide for diagnostic and therapeutic purposes. Femoral artery puncture provides vascular access for the majority of patients. Following removal of the catheter device, hemostasis is usually achieved by a period of manual compression and prolonged immobilization. This requires specialized nursing units and is a considerable strain on the resources of the hospital, and also is a source of inconvenience and discomfort for the patient.

A number of studies have shown that simple manual compression (sandbag or other external compression device) is associated with approximately a 5-10% complication rate at the groin. These are mostly trivial (i.e. small hematoma) but a number of more serious complications can ensue, most notably arterial pseudoaneurysms (with rupture), aterio-venous fistulae, acute aterial occlusion and infection. For these reasons, a number of devices have been designed to increase the efficiency of arterial hemostasis. Arterial closure devices can be categorized into two different types: suture-mediated and nonsuture-mediated. A number of non-suture devices (some FDA approved and some pending FDA clearance) are in use or in clinical trials in the United States. All of these devices use some form of mechanical barrier or "plug" to close the vessel puncture site. Collagen plugs are a common component of these devices and are positioned and held in place by a variety of different mechanisms. Failures and complications occur generally by misplacement of the plug. A purpose of the present invention is to provide a new, accurate, and real-time way for hospital personnel and medical professionals to evaluate, determine and monitor when hemostasis has been achieved in a patient who has undergone arterial puncture and closure.

In an embodiment, the present invention comprises a new device or tissue sealant for closing arterial puncture sites that comprises a collagen and/or thrombin (active clotting) plug that is covalently conjugated or integrated with an optical dye-system designed to be "off" (e.g., non-fluorescent from a pre-quenched state, low fluorescence or non-colored) while the puncture site is open (and still requiring manual compression) and "on" (e.g., highly fluorescent, exhibiting an easily identifiable color in the visible spectrum or exhibiting measureable fluorescence) when hemostasis has been achieved. As known in the art, certain dyes exhibit little to no fluorescence when undergoing free rotation and molecular motion in solution. In some of these dyes, for example, upon excitation, non-radiative energy transfer dominate energy loss processes through solvent-solute-dye interactions. However, when some of these types of dyes are held in a rigidified environment, for example bound to a receptor, surface or another molecule such as DNA, non-radiative energy transfer processes are reduced, thereby resulting in an observed increase in the fluorescence quantum yield. These dyes can be of great use for probing molecular interactions in vivo.

Figure 2A:
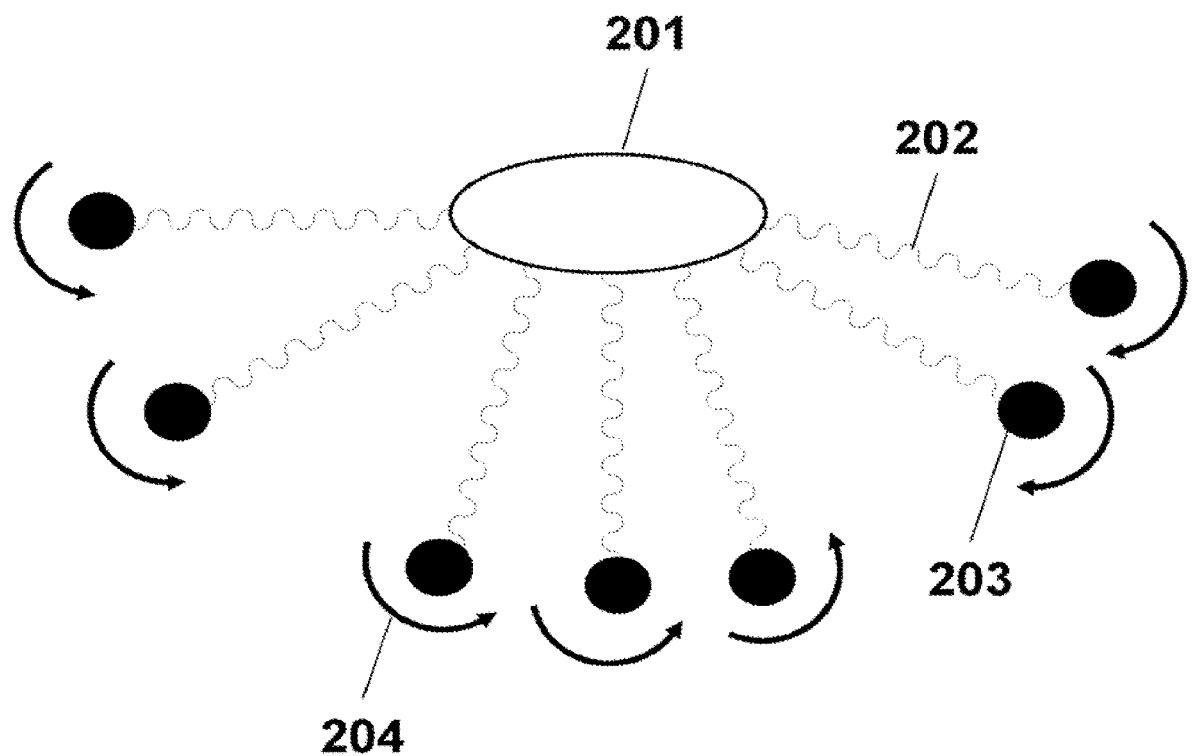
FIG. 2A illustrates an embodiment of a vasculature closure device of the present invention wherein a plurality of optical dyes are covalently linked to a plug.
Figure 2B:
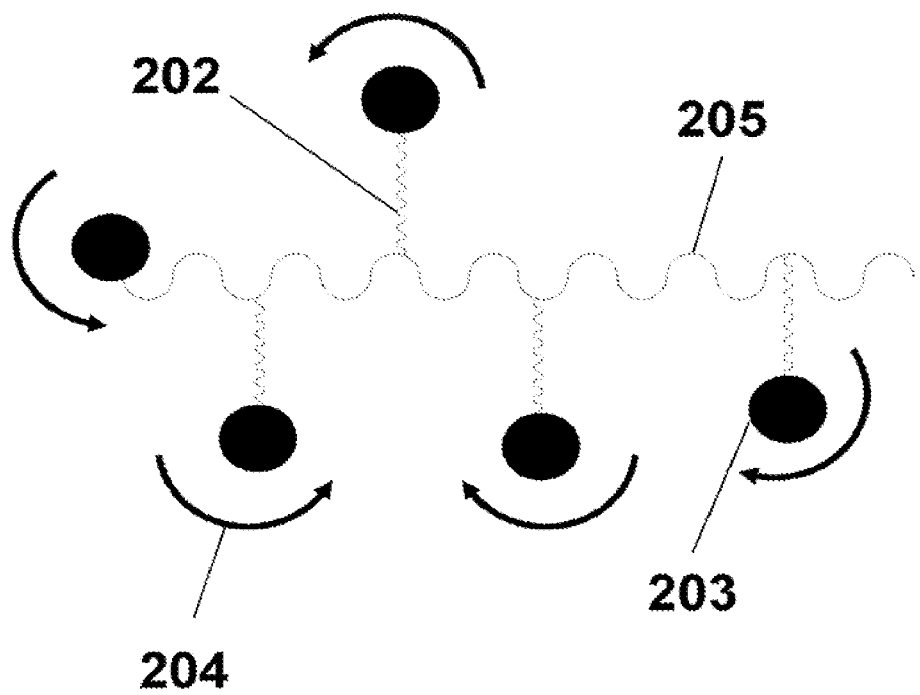
FIG. 2B illustrates an embodiment of a tissue sealant of the present invention wherein a plurality of optical dyes are covalently linked to an adhesive material

FIG. 2A provides a schematic illustration of an embodiment of a vasculature closure device comprising a plug 201 and optical dyes 203 covalently bonded to the plug by connecting groups 202. FIG. 2B provides a schematic illustration of an embodiment of a tissue sealant comprising an adhesive material 205 and optical dye 203 covalently bonded to the sealant by connecting groups 202. As shown in these Figures, a plurality of optical dyes 203 are covalently bonded to a single plug 201 (see FIG. 2A) or a single adhesive material 205 (see FIG. 2B) in these embodiments. The closure device and sealant shown in FIGS. 2A and 2B are in a state prior to activation of the adhesive material or administration of the closure device. The curved arrows 204 in FIGS. 2A and 2B schematically illustrate that the optical dyes bound to adhesive materials or closure devices in this state can undergo substantially free molecular motion, such free rotation and/or vibration, prior to activation of the adhesive material or administration of the closure device. In some embodiments, when the optical dye molecules are excited by exposure to electromagnetic radiation, this free motion results in efficient non-radiative energy transfer processes that reduce or entirely eliminate radiative energy loss processes, such as fluorescence. The reduction of radiative loss process due to solvent interactions commonly involves fluorescence quenching processes. In addition, the availability of substantially free molecular motion, such free rotation and/or vibration, prior to activation of the adhesive material or administration of the closure device, impacts the energy states available for electronic transitions. For some optical dyes, therefore, free molecular motion may significantly impact the wavelengths for excitation of the optical dye and subsequent emission (e.g., fluorescence) wavelength.

Figure 3A:
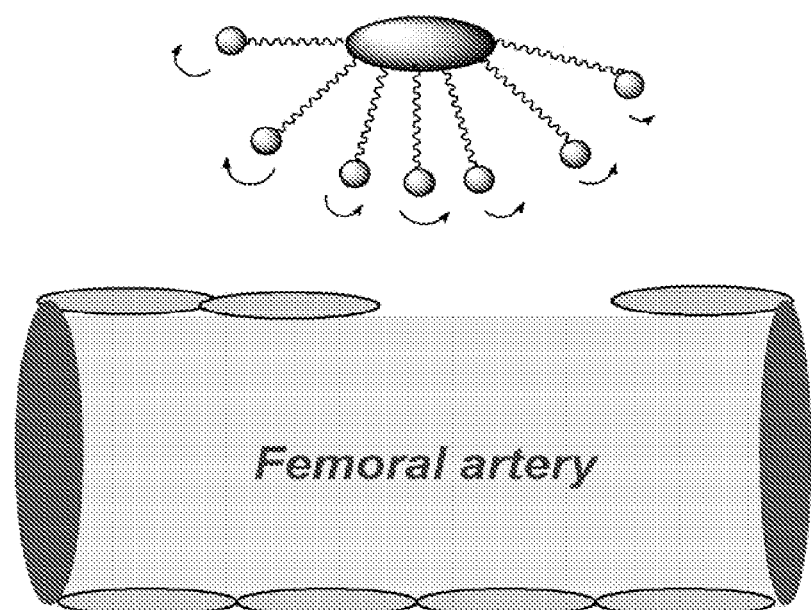
FIGS. 3A and 3B illustrate an embodiment of a vasculature closure device having dye-closure indication functionality.
Figure 3B:
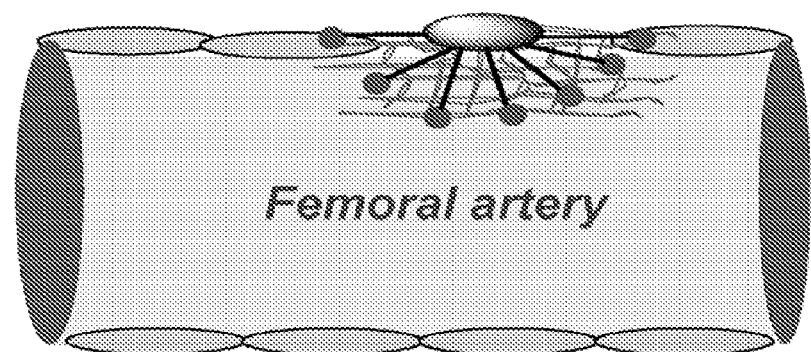
Figure 4:
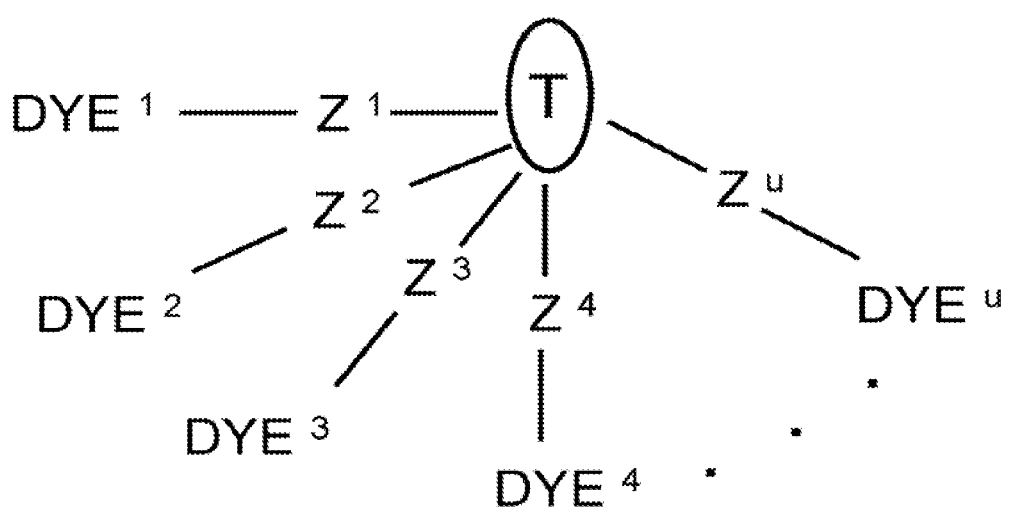
FIG. 4 shows a tissue sealant or closure device configuration wherein a plurality of optical dyes ($DYE^1$, $DYE^2$, $DYE^3$ ... $DYE^n$) are independently linked to the adhesive material or plug (T) component via a plurality of connecting groups ($Z^1$, $Z^2$, $Z^3$ ... $Z^n$). The number of independent DYE-Z groups coordinated to T in tissue sealants and closure devices is selected on the basis of therapeutic application, the composition of the DYE, adhesive material and/or closure device components and the synthetic pathway used for linking DYE and T components.

FIGS. 3A and 3B illustrate an embodiment of a vasculature closure device having a dye-closure indication functionality. FIG. 3A shows the vasculature closure device prior to administration to a vasculature opening and FIG. 3B shows the vasculature closure device upon administration to a vasculature opening, for example upon contacting a vasculature opening generated upon removal of a catheter. Also shown in FIGS. 3A and 3B is vasculature tissue, specifically a femoral artery having a vasculature opening. As shown in FIG. 3A, prior to administration the optical dye components of the closure device are capable of undergoing substantially free molecular motion, as schematically illustrated by the curved arrows. In some embodiments, this molecular motion results in a suppression (e.g., quenching) of fluorescence processes of the optical dye components. As shown in FIG. 3B, upon contacting the closure device with the arterial tissue, for example by application to the vasculature opening and/or surrounding vasculature tissue, the closure device is incorporated into a tissue seal, fibrin network, synthetic polymer network or clot, thereby immobilizing the optical dyes components of the device. In some embodiments, immobilization of optical dyes of the closure device reduces the available molecular motion, thereby resulting in an enhancement of fluorescence from the dyes, for example by decreasing fluorescence quenching. In some embodiments, incorporation of the closure device into a tissue seal, fibrin network, synthetic polymer network or clot provides a measurable, optionally visually observable, shift in the emission intensity, wavelength or wavelength distribution of fluorescence from the dyes.

FIG. 3B schematically illustrates administration of an exemplary vasculature closure device to biological tissue. As shown in this figure, a femoral artery opening is contacted with the closure device resulting in formation of a seal or barrier, optionally provided by the formation of a clot, fibrin network, synthetic polymer network or other tissue seal. As shown in FIG. 3B, the tissue seal formed functions to anchor the device into place and also fixes or otherwise constrains the connecting groups and optical dye components in a rigidified mesh environment. When the seal begins to close though the formation of a fibrin-driven clot, anchoring the plug into place, the linker-dye arms become fixed in a rigidified mesh environment. This enhancement in rigidity and shielding from the circulation provides a measureable enhancement in fluorescence intensity. This change in conformation immobilizes or otherwise holds the optical dye components into place and/or rigidifies the optical dye components, thereby reducing the availability and/or effectiveness of non-radiative energy transfer processes. In this embodiment, fluorescence from the optical dye molecules is enhanced, thereby providing a detectable change in optical conditions upon tissue seal formation. In some embodiments, integration of the dye into a tissue seal of administration of the closure device results in a measurable change in emission (e.g., fluorescence) wavelength, distribution of wavelengths, or intensity or a measurable change in the color or absorption spectrum (e.g., absorption maximum) of the dye component.

The dye molecule can be tethered through a number of potentially useful linkage systems to the plug through a range of connecting groups. The linkage composition can be varied for enhancing photophysical properties of the dye upon seal closure as well as for enhancing the actual seal strength and reduction of time to hemostasis. In some embodiment, for example, this is accomplished by the use of collagen mimetic peptide linkers for connecting groups covalently linking the optical dye and the adhesive material or plug components.

A variety of dye systems are useful for the present tissue sealants and closure devices. One notable and tetherable "light-up" probe that has been used in the DNA binding arena is thiazole orange (FX15). Dye systems useful in the methods, devices, and compositions of the present invention may be further modified, for example, to attach to the connecting groups or plug, to tune the absorption or fluorescence emission spectrum of dye molecules, or to alter other physical properties of the dyes.

(FX15)

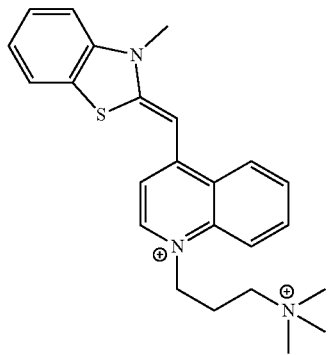

(FX16)

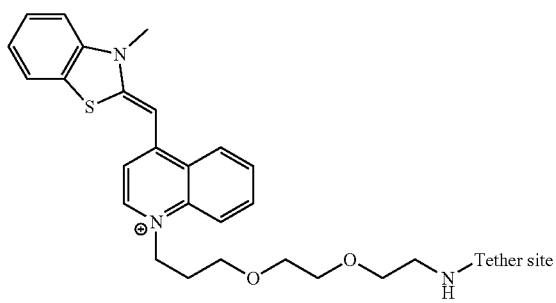

Pyrazine dyes are also useful for the present tissue sealants and closure devices. These dyes include, but are not limited to, the aminopyrazine carboxylates (FX17), carboxyamides (FX18), and carbonitriles (FX19) and their extended π-system variants. These compounds are very small, highly fluorescent (having large Stokes shifts), and possess excellent synthetic and molecular recognition characteristics for designing in "light-up" properties. By way of example, pyrazine dyes may comprise the aminopyrazine carboxylates (FX17), aminopyrazine carboxyamides (FX18), and aminopyrazine carbonitriles (FX19) shown below:

(FX17)

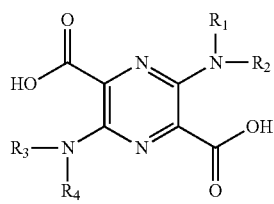

(FX18)

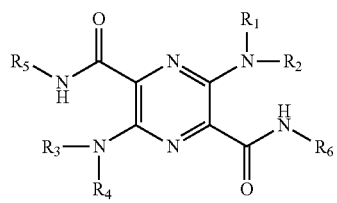

(FX19)

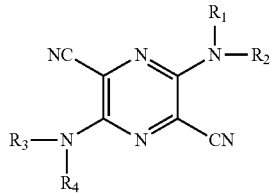

wherein each of $R^1$-$R^6$ is independently hydrogen, $C_1$-$C_{20}$ alkyl, $C_5$-$C_{20}$ aryl, $C_5$-$C_{20}$ heteroaryl, $C_1$-$C_{20}$ cycloalkyl, $C_1$-$C_{20}$ acyl, $C_2$-$C_{20}$ alkenyl, $C_2$-$C_{20}$ alkynyl, $C_5$-$C_{20}$ alkylaryl, halo, halomethyl, dihalomethyl, trihalomethyl, amino, hydroxyl, carboxyl, $C_1$-$C_6$ alkoxycarbonyl, cyano, $NO_2$, phosphate, sulfide, $CO_2R^{38}$, —$COR^{39}$, —$CONR^{40}R^{41}$, —$SOR^{42}$, —$SO_2R^{43}$, —$SO_2OR^{44}$, or —$OSR^{45}$. In an embodiment, each of $R^1$-$R^6$ is independently hydrogen, $C_1$-$C_{10}$ alkyl, $C_5$-$C_{10}$ aryl, $C_5$-$C_{10}$ heteroaryl, $C_1$-$C_{10}$ cylcoalkyl, $C_1$-$C_{10}$ acyl, optionally for some applications wherein each of $R^1$-$R^6$ is independently hydrogen and $C_1$-$C_{10}$ alkyl, and optionally for some applications wherein each of $R^1$-$R^6$ is hydrogen.

EXAMPLE 2

Tissue Sealants Having Collagen, PEG and Thionin Dye Components

A tissue sealant of the invention was prepared, activated and characterized so as to demonstrate useful properties for visualizing formation of a polymer network and/or tissue seal. The tissue sealant included collagen, polyethylene glycol (PEG) and optical dye components. The optical dye is a thionin dye having the formula:

(FX20)

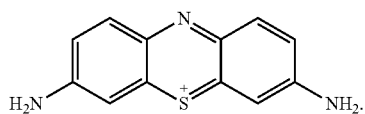

The PEG component has N-succinimido active ester groups as shown in formula (FX21) and an average molecular weight of about 20,000 Daltons.

$$SuO_2C(CH_2)_p—(CH_2CH_2O)_n—(CH_2)_pCO_2Su \quad (FX21);$$

wherein Su are the N-succinimido active ester groups. The collagen (or gelatin) has a molecular weight of about 100,000 Daltons. The ratio of thionin dye to polymer components is approximately 100 to 1.

To a collagen kit (Covidien, North Haven, Conn.) containing 6% collagen by weight, was added the collagen buffer (5 mL) and was stirred vigorously using a vortex for 1 minute. The thick, gelatinous material was then kept at 37° C. water bath for about 10 minutes (or until the gelatinous material became mobile, homogenous solution). Thereafter, 0.5 mL of thionin dye stock solution (2.8 mg of thionin in 5 mL of water) was added to the collagen solution and the entire mixture was stirred vigorously with a vortex for about 30 seconds. To a polyethylene glycol (PEG) kit (Covidien, North Haven, Conn.) containing 5% PEG by weight, was added PEG buffer (2 mL) and was stirred vigorously for about 1 minute. A mixture of the collagen-dye solution (2.5 mL) and the PEG solution (1 mL) was placed in a petri dish (4 cm diameter) in such a manner as to cover the entire area of the dish, and was allowed to polymerize at ambient temperature for 30 min. As a control sample, in another petri dish (4 cm diameter) a mixture of the collagen-dye solution (2.5 mL) and the PEG buffer (without the PEG) (1 mL) was placed in such a manner as to cover the entire area of the dish, and was allowed to solidify at ambient temperature for 30 minutes.

Figure 5:
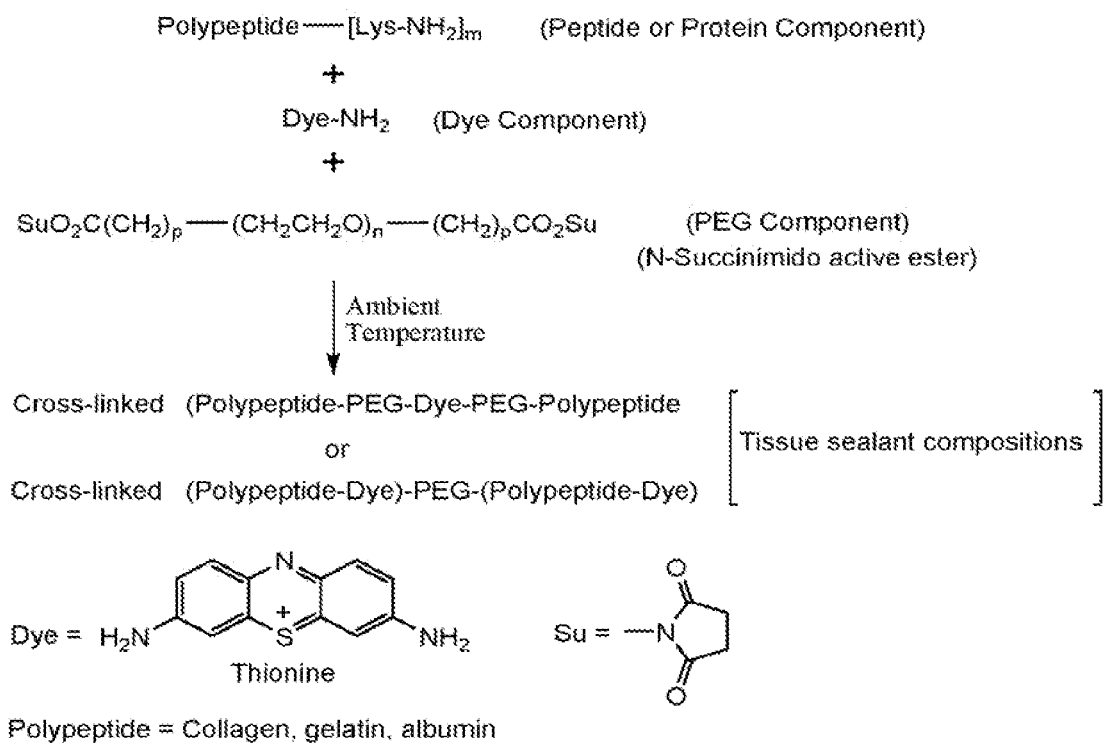
FIG. 5 provides a scheme showing reactions for linking the dye, collagen and PEG components.

FIG. 5 provides a scheme showing reactions for linking the dye, collagen and PEG components, for example, upon activation and formation of a polymer network. As illustrated in FIG. 5, the N-succinimido active ester groups of the PEG component react with free amino groups of the collagen, thereby resulting in activation of the tissue sealant via initiation of cross linking reactions. As also shown in FIG. 5, the N-succinimido active ester groups of the PEG component also react with thionin dye, so as to covalently bond to the thionin dye to the polymer, for example via cross linking reactions. Accordingly, reactions initiated by the PEG component activate the tissue sealant and function to incorporate the dye into the polymer network formed upon activation.

Figure 6A:
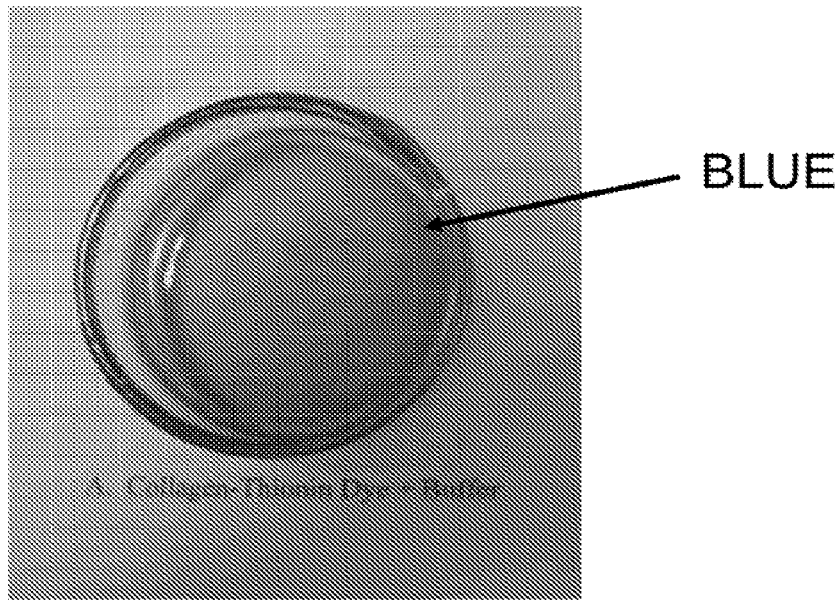
FIGS. 6A and 6B provide photographs of the control sample and the activated tissue sealant sample that demonstrate the changes in optical properties observed upon activation of the tissue sealant.
Figure 6B:
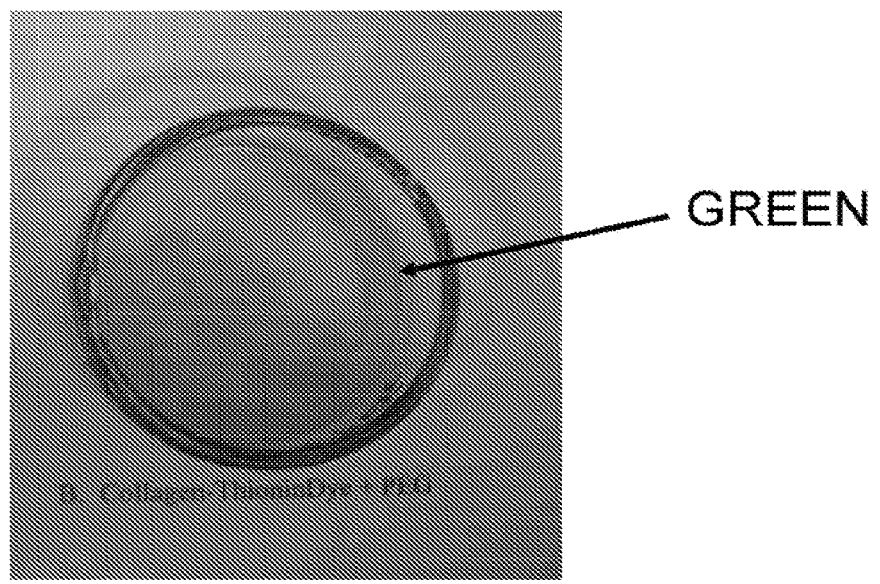

FIGS. 6A and 6B provide photographs of the control sample and the activated tissue sealant sample that demonstrate the changes in optical properties observed upon activation of the tissue sealant. FIG. 6A corresponds to the control sample including collagen, thionin dye and PEG buffer (without PEG) components. As shown in FIG. 6A, the control sample appears blue in color. FIG. 6B corresponds to the activated tissue sealant sample including collagen, thionin dye, PEG and PEG buffer components. As shown in FIG. 6B, the activated tissue sealant sample appears green in color. The control sample and activated tissue sealant sample were visually distinguishable indicating that the two samples absorb and scatter electromagnetic radiation having measurably different wavelengths in the visible region of the electromagnetic spectrum spectrum. Given these clear differences in absorption properties and spectrum, a corresponding measurable difference in the fluorescence emission wavelength and wavelength distribution is also expected between the control sample and activated tissue sealant sample.

REFERENCES

Ruygrok, P. et al, Catheterization and Cardiovascular Interventions, 66:185-191, (2005).

Gerkens, U. et al, Am. J. Cardiol., 1999 Jun. 15; 83(12): 1658-63.

Nygaard, W. et al, Catheterization and Cardiovascular Interventions, 52:3-7, (2001).

Svanvik, N. et al, Anal. Biochem. 2000, 281, 26-35.

Yu, M. et al, J. Am. Chem. Soc. 2005, 127, 4130-4131.

Dervan, P. et al, J. Am. Chem. Soc. 2005, 127, 16685-16691.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, methods steps set forth in the present description. As will be apparent to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

What is claimed is:

1. A method of forming a seal in a biological tissue, the method comprising:
    administering to a subject an effective amount of a tissue sealant to the biological tissue; and
    activating an adhesive material in the tissue sealant, thereby forming the seal in the biological tissue;
    wherein the tissue sealant comprises:
        an adhesive material that is activated to form a seal when contacted with the biological tissue; and
        an optical dye covalently bonded to, or noncovalently associated with, the adhesive material;
    wherein the optical dye exhibits a first optical condition prior to activation of the adhesive material and exhibits a second optical condition distinguishable from the first optical condition after activation of the adhesive material.

2. The method according to claim 1, the method further comprising:
    exposing the tissue sealant to electromagnetic radiation.

3. The method according to claim 1, the method further comprising:
    detecting the first optical condition and the second optical condition and determining a change between the first optical condition and the second optical condition.

4. The method according to claim 3, wherein the change between the first optical condition and the second optical condition is a change in at least one property selected from the group consisting of color, absorbance, reflectance, phosphorescence, chemiluminescence, scattering, fluorescence quantum yield, fluorescence excitation wavelength, fluorescence wavelength distribution, fluorescence wavelength spectrum, emission fluorescence excitation wavelength, emission fluorescence wavelength distribution, emission fluorescence spectrum, optoacoustic properties, and combinations thereof.

5. The method according to claim 1, wherein the optical dye is selected from the group consisting of an anthraquinone dye, a bis-benzimidazole dye, a cyanine, a diazo dye, a phenoselenazine, a phenothiazine, a phenylxanthene, a pyrazine, a thiazole, a xanthene dye, an indocyanine, a squaraine, a dipyrrolo pyrimidone, an anthraquinone, a tetracene, a quinoline, an acridine, an acridone, a phenanthridine, an azo dye, a rhodamine, a phenoxazine, an azulene, an azaazulene, a triphenyl methane dye, an indole, a benzoindole, an indocarbocyanine, a Nile Red dye, a thionin dye, an isosulfan blue dye, a benzoindocarbocyanine, a phenanthridium dye, a phenothiazine dye, a phthalein dye, a styryl dye, a triarylmethane dye, and combinations thereof.

6. The method according to claim 1, wherein the first optical condition is a first fluorescence quantum yield and the second optical condition is a second fluorescence quantum yield; and
    wherein the second fluorescence quantum yield is different from the first fluorescence quantum yield.

7. The method according to claim 6, wherein the first fluorescence quantum yield is substantially equal to 0 and the second fluorescence quantum yield is greater than or equal to 0.01; or
    wherein the second fluorescence quantum yield is greater than the first fluorescence quantum yield by at least a factor of 1.5 or is less than the first fluorescence quantum yield by at least a factor of 1.5.

8. The method according to claim 6, wherein activation of the adhesive material incorporates the optical dye into the tissue seal, fibrin network, or clot and immobilizes the optical dye in the tissue seal, fibrin network, or clot, or rigidifies the optical dye, thereby providing a change from the first optical condition to the second optical condition; and
    wherein activation of the adhesive material initiates a coagulation cascade in the subject.

9. The method according to claim 1, wherein the first optical condition is presence of a color and the second optical condition is absence of a color.

10. The method according to claim 1, wherein the first optical condition is absence of color and the second optical condition is presence of a color.

11. The method according to claim 1, wherein a change between the first optical condition and the second optical condition is a change in wavelength of an emission maximum, a change in wavelength of an absorption maximum or both for the optical dye.

12. The method according to claim 11, wherein the change in wavelength of the emission maximum, the change in wavelength of the absorption maximum or both is at least 20 nm.

13. The method according to claim 11, wherein the change in wavelength of the emission maximum, the change in wavelength of the absorption maximum or both is at least 40 nm.

14. The method according to claim 1, wherein the optical dye is a compound of Formula FX1, or a pharmaceutically acceptable formulation or salt thereof, $$R^1-W^1-(L^1)_a\phantom{xxx}(L^3)_c-W^3-R^3$$
$$R^2-W^2-(L^2)_b\phantom{xxx}(L^4)_d-W^4-R^4$$
(FX1)

wherein
each of $L^1$, $L^2$, $L^3$, and $L^4$, if present, is independently selected from the group consisting of $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, and phenylene;
each of $W^1$, $W^2$, $W^3$, and $W^4$ is independently selected from the group consisting of a single bond, —$(CH_2)_n$mm of growth for BOTRCI pathogens, respectively. The Colby calculation of 114.8 and 502.5 indicated that the benzoxaborole treatment with 0.0044 mg/L or 0.0088 mg/L Compound A, respectively, combined with $CO_2$ was synergistic over the other treatments to inhibit BOTRCI growth in vivo. —$(HCCH)_n$—, —$(CH_2CH_2O)_r$—, —$(CHOH)_s$—, —O—, —S—, —SO—, —$SO_3$—, —$OSO_2$—, —$NR^{13}$—, —CO—, —COO—, —OCO—, —OCOO—, —$CONR^{14}$—, —$NR^{15}CO$—, —$OCONR^{16}$—, —$NR^{17}COO$—, —$NR^{18}CONR^{19}$—, —$NR^{20}CSNR^{21}$—, —$(CH_2)_mO(CH_2)_n$—, —$(CH_2)_mS(CH_2)_n$—, —$(CH_2)_mSO(CH_2)_n$—, —$(CH_2)_mSO_2(CH_2)_n$—, —$(CH_2)_mSO_3(CH_2)_n$—, —$(CH_2)_mOSO_2(CH_2)_n$—, —$(CH_2)_mNR^{22}(CH_2)_n$—, —$(CH_2)_mCO(CH_2)_n$—, —$(CH_2)_mCOO(CH_2)_n$—, —$(CH_2)_mOCO(CH_2)_n$—, —$(CH_2)_mOCOO(CH_2)_n$—, —$(CH_2)_mCONR^{23}(CH_2)_n$—, —$(CH_2)_mNR^{24}CO(CH_2)_n$—, —$(CH_2)_mOCONR^{25}(CH_2)_n$—, —$(CH_2)mNR^{26}COO(CH_2)_n$—, —$(CH_2)_mNR^{27}CONR^{28}(CH_2)_n$—, —$(CH_2)_mNR^{29}CSNR^{30}(CH_2)_n$—, —$(CH_2)_mO(CH_4)_nNR^{31}CO(CH_2)_n$—, —$(CH_2)_mCO(CH_2)_n(CH_2OCH_2)_q(CH_2)_nNR^{32}(CH_2)_nNR^{33}CO(CH_2)_n$—, and —$(CH_2)_mCO(CH_2)_nNR^{34}CO(CH_2)_n$—;
each of $R^1$, $R^2$, $R^3$, and $R^4$ is independently selected from the group consisting of a hydrogen, —$OCF_3$, $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, —$CO_2R^{40}$, $SOR^{41}$, —$OSR^{42}$, —$SO_2OR^{43}$, —$CH_2(CH_2OCH_2)_rCH_2OH$, —$PO_3R^{44}R^{45}$, —$OR^{46}$, —$SR^{47}$, —$NR^{48}R^{49}$, —$NR^{50}COR^{51}$, —CN, —$CONR^{52}R^{53}$, —$COR^{54}$, —NO2, —$SO_2R^{55}$, —$PO_3R^{56}R^{57}$, —$SO_2NR^{58}R^{59}$, —$CH_2(CHOH)_rR^{60}$, and —$(CH_2CH_2)_s R^{61}$;
each of r and s is independently an integer selected from the range of 1 to 100;
each of n, m and q is independently an integer selected from the range of 0 to 10;
each of a, b, c and d is independently 0 or 1;
each of $R^{13}$-$R^{34}$ is independently selected from the group consisting of hydrogen, $C_1$-$C_{20}$ alkyl, $C_1$-$C_{20}$ cycloalkyl, $C_5$-$C_{20}$ aryl, $C_5$-$C_{20}$ heteroaryl, and $C_1$-$C_{20}$ acyl; and
each of $R^{40}$-$R^{61}$ is independently selected from the group consisting of hydrogen and $C_1$-$C_{10}$ alkyl.

15. The method according to claim 1, wherein the optical dye is a compound of Formula FX14, or a pharmaceutically acceptable formulation or salt thereof, $$X^1\phantom{xx}N\phantom{xx}Y^2$$
$$Y^1\phantom{xx}N\phantom{xx}X^2$$
(FX14)

wherein
each of $X^1$, $X^2$, $Y^1$, and $Y^2$ are independently selected from the group consisting of electron withdrawing groups and electron donating groups.

16. The method according to claim 1, wherein the optical dye is a compound of Formula FX11, or a pharmaceutically acceptable formulation or salt thereof, $$T-(L^5)_p-W^5-X-W^1-(L^1)_a\phantom{xxx}N\phantom{xxx}(L^3)_c-W^3-R^3$$
$$R^2-W^2-(L^2)_b\phantom{xxx}N\phantom{xxx}(L^4)_d-W^4-R^4$$
(FX11)

wherein
T is the adhesive material;
X is a synthetic polymer, biopolymer, or —$(CH_2)_2$—, wherein one or more $CH_2$ groups of X may be replaced by NH, O, S, a carbonyl (C=O), or a sulfonyl (S=O or O=S=O); two adjacent $CH_2$ groups may be replaced by —CH=CH— and —C≡C—,
each of $L^1$, $L^2$, $L^3$, $L^4$ and $L^5$, if present, is independently selected from the group consisting of $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, and phenylene;
each of $W^1$, $W^2$, $W^3$, $W^4$ and $W^5$ is independently selected from the group consisting of a single bond, —$(CH_2)_n$—, —$(HCCH)_n$—, —$(CH_2CH_2O)_r$—, —$(CHOH)_s$—, —O—, —S—, —SO—, —$SO_2$—, —$SO_3$—, —$OSO_2$—, —$NR^{13}$—, —CO—, —COO—, —OCO—, —OCOO—, —$CONR^{14}$-, —$NR^{15}CO$—, —$OCONR^{16}$—, —$NR^{17}COO$—, $NR^{18}CONR^{19}$-—, —$NR^{20}CSNR^{21}$—, —$(CH_2)_mO(CH_2)_n$—, —$(CH_2)_mS(CH_2)_n$—, —$(CH_2)_mSO(CH_2)_n$—, —$(CH_2)_mSO_2(CH_2)_n$—, —$(CH_2)_mSO_3(CH_2)_n$—, —$(CH_2)_mOSO_2(CH_2)_n$—, —$(CH_2)_mNR^{22}(CH_2)_n$—, —$(CH_2)_mCO(CH_2)_n$—, —$(CH_2)_mCOO(CH_2)_n$—, —$(CH_2)_mOCO$ $-(CH_2)_n-$, $-(CH_2)_mOCOO(CH_2)_n-$, $-(CH_2)_mCONR^{23}(CH_2)_n-$, $-(CH_2)_mNR^{24}CO(CH_2)_n-$, $-(CH_2)_mOCONR^{25}(CH_2)_n-$, $-(CH_2)_mNR^{26}COO(CH_2)_n-$, $-(CH_2)_mNR^{27}CONR^{28}(CH_2)_n-$, $-(CH_2)_mNR^{29}CSNR^{30}(CH_2)_n-$, $-(CH_2)_mO(CH_2)_nNR^{31}CO(CH_2)_n-$, $-(CH_2)_mCO(CH_2)_n(CH_2OCH_2)_q(CH_2)_nNR^{32}(CH_2)_nNR^{33}CO(CH_2)_n-$, and $-(CH_2)_mCO(CH_2)_nNR^{34}CO(CH_2)_n-$ each of $R^2$, $R^3$, and $R^4$ is independently selected from the group consisting of a hydrogen, $-OCF_3$, $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_3$-$C_{20}$ cycloalkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, $-CO_2R^{40}$, $-SOR^{41}$, $-OSR^{42}$, $-SO_2OR^{43}$, $-CH_2(CH_2OCH_2)_bCH_2OH$, $-PO_3R^{44}R^{45}$, $-OR^{46}$, $-SR^{47}$, $-NR^{48}R^{49}$, $-NR^{50}COR^{51}$, $-CN$, $-CONR^{52}R^{53}$, $-COR^{54}$, $-NO_2$, $-SO_2R^{55}$, $-PO_3R^{56}R^{57}$, $-SO_2NR^{58}R^{59}$, $-CH_2(CHOH)_rR^{60}$, and $-(CH_2CH_2O)_sR^{61}$;

each of r and s is independently an integer selected from the range of 1 to 100;

each of n, m and q is independently an integer selected from the range of 0 to 10;

each of a, b, c, d and p is independently 0 or 1;

each of $R^{13}$-$R^{34}$ is independently selected from the group consisting of hydrogen, $C_1$-$C_{20}$ alkyl, $C_1$-$C_{20}$ cycloalkyl, $C_5$-$C_{20}$ aryl, $C_5$-$C_{20}$ heteroaryl, and $C_1$-$C_{20}$ acyl; and each of $R^{40}$-$R^{61}$ is independently selected from the group consisting of hydrogen and $C_1$-$C_{10}$ alkyl.

17. The method according to claim 1, wherein the optical dye is isosulfan blue or indocyanine green.

18. The method according to claim 1, wherein the adhesive material comprises collagen, fibrin, fibrinogen, fibronectin, prothrombin, thrombin, thromboplastin, factor V, factor X, factor XIII, a coagulation factor, a platelet factor, a coagulation activator, a platelet activator, a vasoconstrictor, a fibrinolysis inhibitor, a crosslinker, a glycosaminoglycan, a polysaccharide, a biopolymer, a synthetic polymer, a growth factor or a combination thereof.

19. The method according to claim 1, wherein the adhesive material comprises a polycyanoacrylate or monomers thereof, a polyethylene glycol or monomers thereof, a succinimide-derivatized polyethylene glycol or monomers thereof, a thiol-derivatized polyethylene glycol or monomers thereof, a polyisocyanate or monomers thereof, a polyacrylate or monomers thereof, a polyamine or monomers thereof, a polyamide or monomers thereof, a polyurethane or monomers thereof, or combinations thereof.

20. The method according to claim 1, wherein activation of the adhesive material in the tissue sealant initiates a coagulation cascade in the subject.

* * * * *